United States Patent
Stiernet et al.

(10) Patent No.: US 6,916,797 B2
(45) Date of Patent: Jul. 12, 2005

(54) α-ARYLETHYLPIPERAZINE DERIVATIVES AS NEUROKININ ANTAGONISTS

(75) Inventors: Françoise Stiernet, Sautin (BE); Christophe Genicot, Court-Saint-Etienne (BE); Marie-Agnes Lassoie, Braine-le-Château (BE); Florence Moureau, Wauthier-Braine (BE); Thomas Ryckmans, Brussels (BE); Thierry Taverne, Loos (FR); Jean-Pierre Henichart, Lille (FR); Michel Neuwels, Waterloo (BE); Solo Goldstein, Suresnes (FR)

(73) Assignee: UCB, S.A., Brussels (BE)

( * ) Notice: Subject to any disclaimer, the term of this patent is extended or adjusted under 35 U.S.C. 154(b) by 382 days.

(21) Appl. No.: 10/168,331

(22) PCT Filed: Dec. 14, 2000

(86) PCT No.: PCT/EP00/12667
§ 371 (c)(1),
(2), (4) Date: Aug. 30, 2002

(87) PCT Pub. No.: WO01/46167
PCT Pub. Date: Jun. 28, 2001

(65) Prior Publication Data
US 2003/0220323 A1 Nov. 27, 2003

(30) Foreign Application Priority Data
Dec. 20, 2000 (EP) ............................................. 99125359

(51) Int. Cl.[7] .................. A61K 31/495; A61K 31/496; C07F 9/6509; C07D 295/15; C07D 295/155

(52) U.S. Cl. ............... 514/85; 514/252.12; 514/254.05; 514/227.8; 514/235.8; 514/218; 514/252.13; 514/254.1; 540/575; 544/337; 544/367; 544/376; 544/379; 544/398; 544/399; 544/58.2; 544/60; 544/121

(58) Field of Search ................................ 544/337, 398, 544/399, 367; 514/85, 252.12, 254.05

(56) References Cited

U.S. PATENT DOCUMENTS 5,624,947 A * 4/1997 Keown et al. ............... 514/392
5,696,123 A * 12/1997 Dollinger et al. ......... 514/252.12
5,885,958 A * 3/1999 Zadina et al. .................. 514/9
5,925,638 A * 7/1999 Chambers et al. ........ 514/254.02

FOREIGN PATENT DOCUMENTS

| DE | 195 20 499 | 3/1996 |
| WO | 94/14767 | 7/1994 |
| WO | 94/24115 | * 10/1994 |
| WO | 96/32386 | 10/1996 |

OTHER PUBLICATIONS

Kawashima et al. Chemical Abstracts, vol. 122, No. 239718, Abstract for WO 94/24115 (1995).*

Ohnmact et al. Annual Reports in Medicinal Chemistry, vol. 33, p. 71–80 (1998).*

* cited by examiner

*Primary Examiner*—Emily Bernhardt
(74) *Attorney, Agent, or Firm*—Wenderoth, Lind & Ponack, L.L.P.

(57) ABSTRACT

The invention relates to new α-arylethylpiperazine of the formula

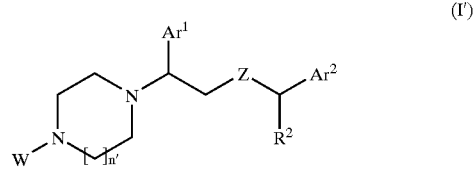

(I')

wherein
 Z represents 0 or S;
 n' represents 1 or 2;
 $R^2$ represents a hydrogen atom or a methyl group;
 W, $Ar^1$ and $Ar^2$ represent various substituents as defined herein;

or non-toxic pharmaceutically acceptable salt, individual optical isomer, or individual diastereoisomer thereof, which are useful as neurokinin receptor antagonists ($NK_1$ antagonists). It also relates to processes for their preparation and use in methods for treatment of asthma and/or allergic rhinitis.

6 Claims, No Drawings

α-ARYLETHYLPIPERAZINE DERIVATIVES AS NEUROKININ ANTAGONISTS

The present invention relates to new α-arylethylpiperazine derivatives, which are useful as neurokinin receptor antagonists ($NK_1$ antagonists). It also relates to processes for the preparation of said α-arylethylpiperazine derivatives, to their use for the prevention and/or treatment of a condition associated with pathogical levels of substance P in a patient and to pharmaceutical compositions containing them.

Neurokinins (also called NKs or tachykinins) are a family of small peptides which are released from neuronal sensory afferents and which share a common carboxy-terminal region Phe-X-Gly-Leu-Met-$NH_2$; in mammals, the main members are substance P (SP), neurokinin A (NKA, also known as substance K) and neurokinin B (NKB, also known as neuromedin K), which act as neurotransmitters and neuromodulators (C. A. Maggi, R. Patacchini, P. Rovero, A. Giachetti, J. Auton. Pharmacol. (1993) 13, 23–93). These three types of neurokinins possess different degrees of potency; their endogenous agonist effect occurs via specific receptors. Three types of neurokinin receptors have been identified: $NK_1$ (SP-preferring), $NK_2$ (NKA-preferring) and $NK_3$ (NKB-preferring), which are widely distributed throughout the central nervous system (CNS) and peripheral nervous system (E. Burcher, C. J. Mussap, J. A. Stephenson, Tachykinin Receptors, Ed. Buck S H, Humana Press, Totowa, N.J. (1994), 125–163; J. E. Maggio, P. W. Mantyh, L. L. Iversen, ibid, 1–38).

Neurokinins have been described to be implicated in numerous physiological and pathological processes such as neuronal modulation, plasma protein extravasation, mast cell degranulation and mitogenic effects (C. A. Maggi, R. Patacchini, P. Rovero, A. Giachetti, J. Auton. Pharmacol. (1993) 13, 23–93). In the peripheral nervous system, evidence suggests that neurokinins released from peripheral endings of sensory nerves are responsible for the phenomenon of neurogenic inflammation. Within the CNS, SP may serve as a neuromodulator of inputs from unmyelinated C-fibers involved in nociception to the central terminals of primary sensory neurones in the brainstem and spinal cord dorsal horn, suggesting a clinical utility for $NK_1$ receptor antagonists in the treatment of pain, particularly migraine (S. M. Moussaoui et al., Eur. J. Pharmacol. (1993) 238, 421–4; F. M. Curtler et al., Neuroscience (1995) 64, 741–50). SP-containing afferent nerve fibers also inervate the brain region of the nucleus tractus solitarius, an area involved in the control of emesis, suggesting the use of $NK_1$ receptor antagonists as antiemetics (F. D. Tattersall, W. Rycroft, R. G. Hill, R. J. Hargreaves, Neuropharmacology (1994) 33, 259–60; J. W. Watson, S. F. Gonsalves, A. A. Fossa et al., Br. J. Pharmacol. (1995) 115, 84–94). In the lung, neurokinins are released as a consequence of inflammatory processes and cause plasma protein extravasation, oedema formation, increased blood flow and mucus hypersecretion via $NK_1$ receptors (J. A. Lowe, Emerging Drugs (1996) 1–18). Thus selective $NK_1$ antagonists may have a potential therapeutic indication in the treatment of pulmonary diseases, in particular asthma and bronchitis.

There is also evidence supporting a role for SP in allergic rhinitis. First, in patients with allergic rhinitis, nasal SP content significantly increases immediately after nasal allergen challenge. Moreover, at the clinical peak of the late allergic reaction, SP levels are also raised (B. L. Mosimann et al., J. Allergy Clin. Immunol. (1993) 92, 95–104). Second, in allergic rhinitis, intranasal SP challenges induce vasodilatation, plasma leakage and recruitment of inflammatory cells (I. Fajac et al., Allergy (1995) 50, 970–5; A. Konn et al., Ann. Otol. Rhino. Laryngol. (1996) 105, 648–53) and the reduction of SP content in nasal secretions (after chronic capcaisin treatment) is related to the reduction of the clinical symptoms of allergic rhinitis (R. Zhang et al., Chung Hua Erh Pi Yen Hou Ko Tsa Chih (1995) 30, 163–5). Third, SP enhances antigen-evoked mediator release from human nasal mucosa by interaction with mast cells (C. R. Baumgarten C. R. et al, Peptides (1996) 17, 25–30).

The first potent non-peptide $NK_1$ receptor antagonists, i.e. CP-96,345 (R. M. Snider, S. J. W. Constantine, J. A. Lowe et al. Science (1991) 251, 435–7) and RP-67,580 (J. F. Peyronel, A. Truchon, C. Moutonnier, C. Garret, Bioorg. & Med. Chem. Lett. (1992) 2, 37–40) were discovered in 1991–1992. While CP-96,345 exhibited good selectivity for $NK_1$ receptors with respect to $NK_2$ and $NK_3$ receptors, it showed significant affinity for a number of ion channels, notably the verapamil-sensitive L-type $Ca^{2+}$ binding site (M. Caeser, G. R. Seabrook, J. A. Kemp, Br. J. Pharmacol. (1993) 109, 918–24). Such properties are undesirable from a therapeutic point of view because they are indicative of potential cardiovascular side-effects. This finding led to the discontinuation of further preclinical and clinical investigation of the compounds. Structure-activity relationship (SAR) modifications based on CP-96,345 provided other clinical candidates. For example CP-99,994 was determined to have good $NK_1$ selectivity and lower interaction with the verapamil-sensitive L-type $Ca^{2+}$ binding site than CP-96, 345 (T. Rosen, T. F. Seegar, S. McLean et al., J. Med. Chem. (1993) 36, 3197–3201). It was evaluated in phase II clinical trials for asthma but first trials were reported unsuccessful, possibly due to its poor bioavailability (J. A. Lowe, Emerging Drugs (1996) 1–18; J. V. Fahy, H. F. Wong, P. Gepetti et al., Am. J. Respir. Crit. Care Med. (1995) 152, 879–884).

As to RP-67,580, it exhibited some $NK_1$ affinity. Molecular modifications by SAR led to improved candidates, such as RP-100,893, for example. It has been evaluated in clinical trials for the treatment of migraine; however, activity after oral administration was reported to be no better than placebo activity, possibly due to poor brain penetration (C. J. Swain, R. J. Hargraves, Annual Reports in Medicinal Chemistry, Vol. 31, Bristol, J. A. (Ed.) Academic Press: San Diego (1996) 111–120).

In view of the undesirable side-properties of these first non-peptide neurokinin antagonists, intensive work has been carried out by various teams in order to find other non-peptide $NK_1$ antagonists.

In particular, patent application WO 94/14767 and U.S. Pat. No. 5,624,947 disclose aromatic compounds presented as valuable in the treatment of a wide variety of clinical conditions which are characterised by the presence of an excess of tachykinins, in particular substance P, one of these compounds being the hydrochloride salt of (±)-1-[(3,5-bistrifluoromethylphenyl)methyloxy]-2-N-morpholino-2-phenylethane. Patent application DE 19520499 discloses disubstituted piperazines and piperidines presented for their neurokinin receptor antagonist properties. Amongst the most promising candidates, this document discloses 3,5-bistrifluoromethylbenzyl-[2-(2-methoxyphenyl)-2-(4-(2-phenylethyl)-piperazin-1-yl)-ethyl]-amine, 3,5-bistrifluoromethylbenzyl-[2-(2-methoxyphenyl)-2-(4-cycloheptylpiperazin-1-yl)-ethyl]-amine and 3,5-bistrifluormethylbenzyl-[2-(2-methoxyphenyl)-2-(4piperidin-1-yl)-piperidin-1-yl)-ethyl]-amine.

We have now found other non-peptide selective $NK_1$ receptor antagonists with no or low affinity for $Ca^{2+}$ ion channels and which exhibit good oral bioavailability and duration of action, these compounds exhibiting useful properties for the prevention and/or treatment of a condition associated with pathological levels of substance P in a patient.

Accordingly, the present invention relates to new α-arylethylpiperazine derivatives of formula I

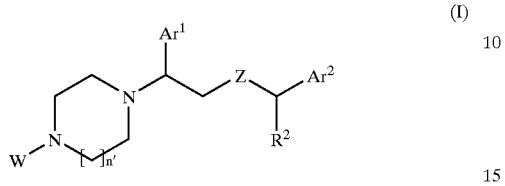

wherein

Z represents O or S;

n' represents 1 or 2;

$R^2$ represents a hydrogen atom or a methyl group;

W represents (i) a cyclohexyl group substituted by a COOH, 2-phenylacetic acid or alkyl 2-phenylacetate group, (ii) a group of formula

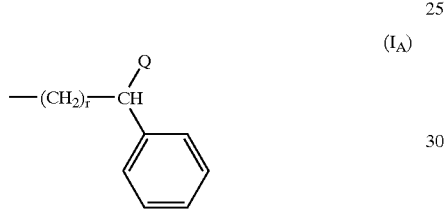

wherein r represents 1, 2 or 3 and Q represents OH or —NH—CO—$CH_3$, or (iii) a group of formula $R^1$—$(CH_2)_n$—X—$(CH_2)_m$— in which $R^1$ represents a CN, $CONR^iR^{ii}$, CONHOH, $CONHCH_2CO_2H$, $CONHCH_2CO_2alkyl$, $CONHSO_2alkyl$, $CONHSO_2phenyl$, $CONHSO_2tolyl$, COOH, COOalkyl, OH, $SO_3H$, $PO(OR^{iii})(OR^{iv})$ group, a mono-, di- or tri-substituted phenyl group in which the substituent is selected from COOH, COOalkyl or $OCH_3$, a heteroaryl, a tetrazole, a morpholine, a thiomorpholine, a thiomorpholine S,S-dioxide, a phthalimide group or a triazolone of formula

wherein $R^i$, $R^{ii}$, $R^{iii}$ and $R^{iv}$ independently represent a hydrogen atom or an alkyl group;

X represents a single bond, an oxygen atom or a methylene group;

m represents 1 or 2, provided that m is not 1 when X is O;

n represents 0, 1 or 2, provided that N is not 0 or 1 when X represents O and R1 represents OH;

$Ar^1$ represents a phenyl, aryl, heteroaryl, or mono-, di- or tri-substituted phenyl group in which the substituents are selected from a halogen atom, an alkyl, trifluoromethyl, hydroxy, alkoxy, $SCH_3$, CN, $NO_2$, $CONH_2$, COOH, COOalkyl or amino group, or mono-substituted heteroaryl group in which substituent is a halogen atom;

$Ar^2$ represents a substituted phenyl group of formula

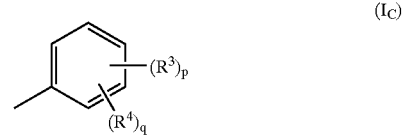

in which $R^3$ represents a halogen atom, an alkyl, alkoxy, trifluoromethyl, COOH, CN, COOalkyl or $CONH_2$ group;

$R^4$ represents a halogen atom, a trifluoromethyl or alkyl group;

p and q independently represent 0, 1, 2 or 3;

or a group of formula

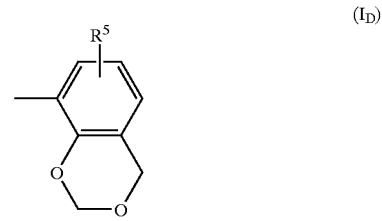

in which $R^5$ represents a halogen atom;

all alkyl and alkoxy groups being linear or branched and having from 1 to 4 atoms of carbon, as well as non-toxic pharmaceutically acceptable salts, individual optical isomers, individual diastereoisomers or prodrugs thereof.

The present invention also relates to new α-arylethylpiperazine derivatives of formula II

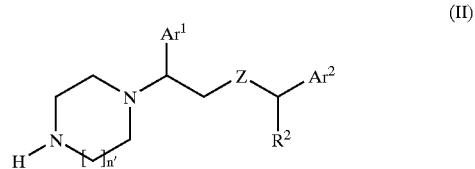

wherein

Z represents O or S;

n' represents 1 or 2;

$R^2$ represents a hydrogen atom or a methyl group;

$Ar^1$ represents a phenyl, aryl, heteroaryl, or mono-, di- or tri-substituted phenyl group in which the substituents are selected from a halogen atom, an alkyl, trifluoromethyl, hydroxy, alkoxy, $SCH_3$, CN, $NO_2$, $CONH_2$, COOH, COOalkyl or amino group, or a mono-substituted heteroaryl group in which substituent is a halogen atom;

Ar² represents a substituted phenyl group of formula (II_A)

in which
R³ represents a halogen atom, an alkyl, alkoxy, trifluoromethyl, COOH, CN, COOalkyl or CONH₂ group;
R⁴ represents a halogen atom, a trifluoromethyl or alkyl group;
p and q independently represent 0, 1, 2 or 3, provided that p is not 0 and q is not 0 when Ar¹ is a phenyl para-substituted by a fluorine atom;
or a group of formula (II_D)

in which R⁵ represents a halogen atom;
all alkyl and alkoxy groups being linear or branched and having 1 to 4 atoms of carbon;
as well as non-toxic pharmaceutically acceptable salts, individual optical isomers or individual diastereoisomers thereof.

The expression halogen atom as used herein includes fluorine, chlorine, bromine and iodine atoms.

The expression aryl as used herein includes 1-naphtyl or 2-naphtyl groups.

The expression heteroaryl as used herein includes pyridine, quinoline, isoquinoline, furan, thiophen, benzofuran, benzothiofuran or indole.

Preferred compounds according to the present invention are α-arylethylpiperazine derivatives of formula I'

(I')

wherein
Z represents an oxygen atom;
n' represents 1;
R² represents a hydrogen atom or a methyl group;
W represents
  (i) a cyclohexyl group substituted by COOH, or
  (ii) a group of formula R¹—(CH₂)ₙ—X—(CH₂)ₘ— in which
    R¹ represents CN, CONHSO₂alkyl, COOH, COOalkyl, SO₃H, PO(OH)₂, a phenyl group mono-substituted by COOH, a tetrazole group or a triazolone of formula (I'_A)

X represents a single bond, an oxygen atom or a methylene group
m represents 1 or 2, provided that m is not 1 when X is an oxygen atom;
n represents 0, 1 or 2, provided that n is not 0 or 1 when X represents an oxygen atom and R¹ represents OH;
Ar¹ represents phenyl, a mono-, di- or tri-substituted phenyl group in which the substituents are selected from a halogen atom, an alkyl group, CN or NO₂;
Ar² represents a substituted aryl group of formula (I'_B)

in which
R³ represents a halogen atom or a trifluoromethyl group;
p represents 0, 1, 2 or 3;
the alkyl groups being linear or branched and having 1 to 4 atoms of carbon, as well as non-toxic pharmaceutically acceptable salts, individual optical isomers, individual diastereoisomers or prodrugs thereof.

Particularly preferred compounds according to the invention include
[2-(4-{2-[1-(3,5-Bis-trifluoromethyl-phenyl)-ethoxy]-1-phenyl-ethyl}-piperazin-1-yl)-ethoxy]-acetic acid;
(4-{2-[1-(3,5-Bis-trifluoromethyl-phenyl)-ethoxy]-1-phenyl-ethyl}-piperazin-1-yl)-acetic acid;
4-{4-[2-(3,5-Bis-trifluoromethyl-benzyloxy)-1-phenyl-ethyl]-piperazin-1-yl}-cyclohexanecarboxylic acid;
6-{4-[2-(3,5-Bis-trifluoromethyl-benzyloxy)-1-phenyl-ethyl]-piperazin-1-yl}-hexanoic acid;
{4-[2-(3,5-Bis-trifluoromethyl-benzyloxy)-1-phenyl-ethyl]-piperazin-1-yl}-acetonitrile;
3-{4-[2-(3,5-Bis-trifluoromethyl-benzyloxy)-1-phenyl-ethyl]-piperazin-1-yl}-propane-1-sulfonic acid;
5-{4-[2-(3,5-Bis-trifluoromethyl-benzyloxy)-1-phenyl-ethyl]-piperazin-1-yl}-pentanoic acid;
(2-{4-[2-(3,5-Bis-trifluoromethyl-benzyloxy)-1-phenyl-ethyl]-piperazin-1-yl}-ethoxy)-acetic acid;
{4-[2-(3,5-Bis-trifluoromethyl-benzyloxy)-1-phenyl-ethyl]-piperazin-1-yl}-acetic acid;
{4-[2-(3,5-Bis-trifluoromethyl-benzyloxy)-1-(3,4,5-trifluoro-phenyl)-ethyl]-piperazin-1-yl}-acetic acid;
4-{4-[2-(3,5-Bis-trifluoromethyl-benzyloxy)-1-phenyl-ethyl]-piperazin-1-ylmethyl}-benzoic acid;
{4-[2-(3,5-Dibromo-benzyloxy)-1-phenyl-ethyl]-piperazin-1-yl}-acetic acid;
{4-[2-(3,5-Bis-trifluoromethyl-benzyloxy)-1-para-tolyl-ethyl]-piperazin-1-yl}-acetic acid;
(2-{4-[2-(3,5-Bis-trifluoromethyl-benzyloxy)-1-phenyl-ethyl]-piperazin-1-yl}-ethyl)-phosphonic acid;
{4-[2-(3,5-Bis-trifluoromethyl-benzyloxy)-1-(2,3-difluoro-phenyl)-ethyl]-piperazin-1-yl}acetic acid;
{4-[2-(3,5-Bis-trifluoromethyl-benzyloxy)-1-(2-nitro-phenyl)-ethyl]-piperazin-1-yl}-acetic acid;

N-[(2-{4-[2-(3,5-Bis-trifluoromethyl-benzyloxy)-1-phenyl-ethyl]-piperazin-1-yl}-ethoxy)-acetyl]-methanesulfonamide;
{4-[2-(3,5-Dichloro-benzyloxy)-1-phenyl-ethyl]-piperazin-1-yl}-acetic acid;
{4-[2-(3,5-Bis-trifluoromethyl-benzyloxy)-1-(4-cyano-phenyl)-ethyl]-piperazin-1-yl}-acetic acid;
5-{4-[2-(3,5-Bis-trifluoromethyl-benzyloxy)-1-phenyl-ethyl]-piperazin-1-ylmethyl}-2,4-dihydro-[1,2,4]triazol-3-one;
1-[2-(3,5-Bis-trifluoromethyl-benzyloxy)-1-phenyl-ethyl]-4-[4-(1H-tetrazol-5-yl)-butyl]-piperazine;
1-[2-(3,5-Bis-trifluoromethyl-benzyloxy)-1-phenyl-ethyl]-4-[2-(1H-tetrazol-5-ylmethoxy)-ethyl]-piperazine;
1-[2-(3,5-Bis-trifluoromethyl-benzyloxy)-1-(4-fluoro-phenyl)-ethyl]-4-[4-(1H-tetrazol-5-yl)-butyl]-piperazine;
1-{2-[1-(3,5-Bis-trifluoromethyl-phenyl)-ethoxy]-1-phenyl-ethyl}-4-[4-(1H-tetrazol-5-yl)-butyl]-piperazine;
1-{2-[1-(3,5-Bis-trifluoromethyl-phenyl)-ethoxy]-1-phenyl-ethyl}-4-[5-(1H-tetrazol-5-yl)-pentyl]-piperazine;
(2-{4-[2-(3,5-Bis-trifluoromethyl-benzyloxy)-1-phenyl-ethyl]-piperazin-1-yl}-ethoxy)-acetic acid isobutyl ester;
3-{4-[2-(3,5-Bis-trifluoromethyl-benzyloxy)-1-phenyl-ethyl]-piperazin-1-ylmethyl}-benzoic acid;
4-{4-[2-(3,5-Bis-trifluoromethyl-benzyloxy)-1-phenyl-ethyl]-piperazin-1-yl}-butyric acid;

as well as non-toxic pharmaceutically acceptable salts, individual optical isomers or individual diastereoisomers thereof.

The present invention also relates to non-toxic pharmaceutically acceptable salts of α-arylethylpiperazine derivatives of formula I. Such pharmaceutically acceptable salts include non-toxic pharmaceutically acceptable acid addition salts of α-arylethylpiperazine derivatives of formula I. As examples there may be mentioned salts of mineral acids, such as hydrochloric, hydrobromic, sulfuric, nitric and phosphoric acids and salts of organic acids, such as acetic, citric, tartaric, benzoic, salicylic and maleic acids. Anhydrous and hydrated forms of such salts are also encompassed by the present invention.

When the compound of formula I carries an acid moiety, pharmaceutically acceptable salts of compounds of formula I also include metal salts such as alkaline metal salts (such as sodium, potassium) or alkaline earth metal salts (such as calcium or magnesium salts).

When the molecule contains one or several asymmetric carbon atoms, the compound of formula I may either be in the form of a racemic mixture, in the form of one of its individual enantiomers or in the form of one of its individual diastereoisomers. It is to be understood that all such individual enantiomers and diastereoisomers and mixtures thereof in any proportion are encompassed within the scope of the present invention.

The term prodrugs as used herein refers to compounds which are rapidly transformed in vivo into the compounds of general formula I (see T. Higuchi and V. Stella, "Pro-drugs as Novel Delivery Systems", Vol 14 of the A.C.S. Symposium Series, and Bioreversible Carriers in Drug Design, ed. Edward B. Roche, American Pharmaceutical Association and Pergamon Press, 1987 for a detailed discussion).

The α-arylethylpiperazine derivatives of formula I may be prepared by one of the following processes:

(a) when, in formula I, $Ar^1$ represents a phenyl, aryl or heteroaryl group, a mono-, di- or trisubstituted phenyl group in which the substituents are selected from a halogen atom, an alkyl, trifluoromethyl, alkoxy, $SCH_3$ or $NO_2$ group, or a mono-substituted heteroaryl group in which substituent is a halogen atom, $Ar^2$, Z, $R^2$ and n' having the same meanings as given above in general formula I, and, furthermore, (a.1) when, in formula I, W represents
(i) an alkyl 2-phenylacetate group,
(ii) a group of formula

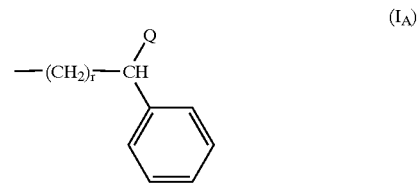

wherein r represents 1, 2 or 3 and Q represents OH, or
(iii) a group of formula $R^1$—$(CH_2)_n$—X—$(CH_2)_m$— in which $R^1$ represents a CN, $CONR^iR^{ii}$, COOalkyl, OH, $SO_3H$ or $PO(OR^{iii})(OR^{iv})$ group, a mono-, di- or trisubstituted phenyl group in which the substituent is COOalkyl or $OCH_3$, a pyridine, morpholine, thiomorpholine, thiomorpholine-(S,S)-dioxide or phthalimide group, wherein $R^i$ and $R^{ii}$ represent a hydrogen atom or an alkyl group and $R^{iii}$ and $R^{iv}$ represent an alkyl group, n, m and X having the same meanings as given above in general formula I, an α-arylethylpiperazine of formula II is reacted with a compound of formula III according to the equation

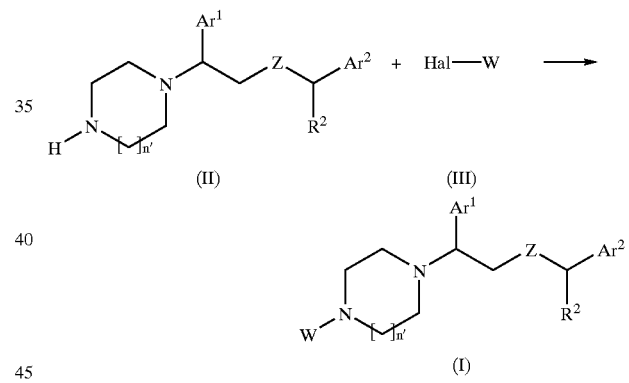

wherein $Ar^1$, $Ar^2$, Z, $R^2$, n' and W have the same meanings as stated above and Hal represents a halogen atom, preferably a chlorine, bromine or iodine atom.

This reaction is known per se and is generally carried out in an inert solvent, for example toluene, dimethylformamide, an alcohol or dichloroethane, in the presence of an acid acceptor, such as a tertiary organic base, for example triethylamine, or an inorganic base, for example sodium carbonate, sodium hydrogenocarbonate, potassium carbonate or potassium hydrogenocarbonate.

(a.2) when, in formula I, W represents
(i) 2-phenylacetic acid, or
(ii) a group of formula $R^1$—$(CH_2)_n$—X—$(CH_2)_m$—, in which $R^1$ represents $CONHCH_2CO_2H$, COOH, PO(OH)(OEt), $PO(OH)_2$ or a mono-, di- or trisubstituted phenyl group in which the substituents are COOH, n, m and X having the same meanings as given above in general formula I, the corresponding compound of formula I wherein W is (i) an alkyl 2-phenylacetate or
(ii) a group of formula $R^1$—$(CH_2)_n$—X—$(CH_2)_m$— in which $R^1$ represents CN, $CONH_2$, $CONHCH_2CO_2$alkyl, COOalkyl, $PO(OEt)_2$ or a mono-, di- or tri-substituted phenyl group in which the substituent is COOalkyl, n, m and X having the same meanings as given above in general formula I, is hydrolysed in an aqueous, alcoholic or aqueous-alcoholic medium by an acid or a base.

(a.3) when, in formula I, W is a group of formula $R^1$—$(CH_2)_n$—X—$(CH_2)_m$— wherein n, m and X have the same meaning as given above in general formula I, and a.3.1. $R^1$ is CN, the corresponding compound of formula I in which $R^1$ is $CONH_2$ is dehydrated;

a.3.2. $R^1$ is $CONH_2$, the corresponding compound of formula I in which $R^1$ is COOalkyl is ammonolyzed;

a.3.3. $R^1$ is COOalkyl or $CONHCH_2$COOalkyl, the corresponding compound of formula I in which $R^1$ is COOH or $CONHCH_2$COOH is esterified;

a.3.4. $R^1$ is $CONR^iR^{ii}$, $R^i$ and $R^{ii}$ independently representing a hydrogen atom or an alkyl group, at least one of $R^i$ or $R^{ii}$ being an alkyl group, the corresponding compound of formula I in which $R^1$ is COOH or COOalkyl is aminolyzed.

These transformations may be performed under any appropriate conditions known to the person skilled in the art.

(a.4) when, in formula I, W is a group of formula $R^1$—$(CH_2)_n$—X—$(CH_2)_m$— wherein $R^1$ represents a triazolone of formula

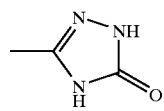

(I$_B$)

and n, m and X have the same meanings as in general formula I, an α-arylethylpiperazine of formula II

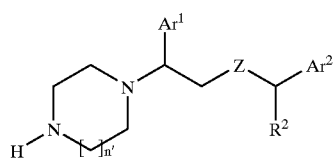

(II)

wherein $Ar^1$, $Ar^2$, Z, $R^2$ and n' have the same meanings as stated above is reacted under heating with a (chloromethyl)amidrazone of formula XIX

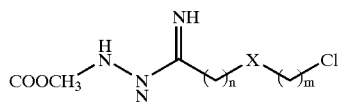

(XIX)

wherein n, m and X have the same meanings as stated above.

This reaction may be carried out following the method described in Ladduwahetty T. et al., J. Med. Chem. (1996), 39, 2907–2914.

(a.5) when, in formula I, W is a group of formula $R^1$—$(CH_2)_n$—X—$(CH_2)_m$— wherein $R^1$ is a tetrazole, n, m and X having the same meanings as given above in general formula I, the corresponding compound of formula I wherein $R^1$ is CN is reacted with azidotrimethylsilane in the presence of dibutyltin oxide.

This transformation may be performed according to the procedure disclosed in Wittenberger S. et al., J. Org. Chem. (1993), 58, 4139–4141 or Owens A. P. et al., Bioorg. Med. Chem. Letters (1998), 8, 51–56.

(a.6) when, in formula I, W is a group of formula $R^1$—$(CH_2)_n$—X—$(CH_2)_m$— wherein $R^1$ represents $CONHSO_2$alkyl, $CONHSO_2$phenyl or $CONHSO_2$tolyl, n, m and X having the same meanings as given above in general formula I, the corresponding compound of formula I in which $R^1$ is COOH is reacted with a sulfonamide of formula $R^v$—$SO_2$—$NH_2$ in which $R^v$ represents an alkyl, phenyl or 4-methylphenyl group. This reaction may be performed under conventional peptide synthesis conditions such as, for example, those described in "Principles of Organic Synthesis" Volume 16, M. Bodansky, Springer-Verlag Berlin Heidelberg New York Tokyo 1984.

(a.7) when, in formula I, W is a group of formula $R^1$—$(CH_2)_n$—X—$(CH_2)_m$, wherein $R^1$ represents $CONHSO_2$alkyl, $CONHSO_2$phenyl or $CONHSO_2$tolyl, n=0, X=O and m=2, the corresponding α-arylethylpiperazine of formula I wherein $R^1$ is HO—$(CH_2)_m$ is reacted with the compound of formula R—$SO_2$—N=C=O in which R represents alkyl, phenyl or 4-methylphenyl.

This reaction may, for example, be carried out under the conditions described in Friesen R. W. and Phipps L. G., Synlett (1991), 420–422.

(a.8) when, in formula I, W is a group of formula

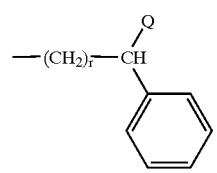

(I$_A$)

wherein Q=NH(CO)CH$_3$, the corresponding compound of formula I in which Q is OH is reacted with acetonitrile in the presence of acid. The conditions used for this reaction are for example those disclosed in European Patent application 474,561 (page 37).

The starting compound of formula I in which Q=OH may be obtained by method a.1 described above.

(a.9) when, in formula I, W is a cyclohexyl group substituted by COOH, the corresponding compound of formula I in which W is a cyclohexyl group substituted by COOalkyl is hydrolysed in an aqueous, alcoholic or aqueous-alcoholic medium in presence of an acid or a base. The starting compound of formula I in which W is a cyclohexyl group substituted by COOalkyl may be obtained by reductive amination of a cyclohexanone of formula XXVII with a piperazine of formula II according to the equation

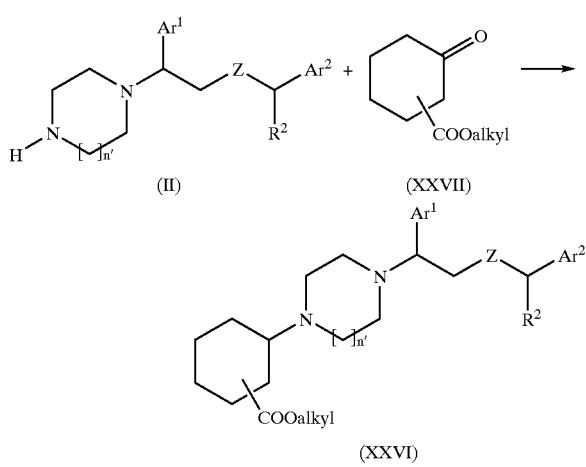

In these formulae, $Ar^1$, $Ar^2$, Z, $R^2$ and n' have the same meanings as stated above. This reaction may for example be carried out according to the procedure disclosed in Maryanoff B. E. et al., J. Med Chem. (1981), 24 (1), 79–88.

(a.10) when, in formula I, W is a group of formula $R^1$—$(CH_2)_n$—X—$(CH_2)_m$ wherein $R^1$ represents CONHOH, n, m and X having the same meanings as given above in general formula I, a corresponding compound of formula I wherein $R^1$ represents COOH is coupled with the compound of formula XXIX

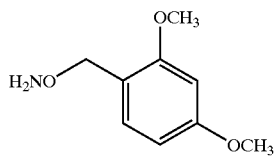

(XXIX)

followed by treatment with trifluoroacetic acid.

This reaction may be carried out according to the procedure disclosed in Barlaam B. et al., Tetrahedron Lett. (1998), 39, 7865–7868.

(b) when, in formula I, Ar1 is a mono-, di- or tri-substituted phenyl group in which the substituents are $COOCH_3$, $Ar^2$, Z, $R^2$ and n' have the same meanings as given above in general formula I and W is a group of formula $R^1$—$(CH_2)_n$—X—$(CH_2)_m$— wherein $R^1$ represents COOalkyl, n, m and X having the same meanings as given above in general formula I, the corresponding compound of formula I in which $Ar^1$ is a mono-, di- or tri-substituted phenyl group in which the substituents are bromine atoms is submitted to methoxycarbonylation by carbon monoxide treatment in the presence of palladium(II) acetate, 1,3-bis(diphenylphosphino)propane and triethylamine in methanol (see Lin C. H. et al., J. Med. Chem. (1993), 36, 2208–2218 for detailed conditions).

c) when, in formula I, $Ar^1$ is a mono-, di- or tri-substituted phenyl group in which the substituents are CN, $Ar^2$, Z, $R^2$ and n' have the same meanings as given above in general formula I and W is a group of formula $R^1$—$(CH_2)_n$—X—$(CH_2)_m$ wherein $R^1$ represents COOalkyl, n, m and X having the same meanings as in general formula I, a corresponding compound of formula I $Ar^1$ is a mono-, di- or tri-substituted phenyl group in which the substituents are Bromine atoms is reacted with zinc cyanide (see Tschaen D. M. et al., J. Org. Chem. (1995), 60, 4324–4330 for detailed conditions).

(d) when in formula I, $Ar^1$ is a mono-, di- or tri-substituted phenyl group in which the substituents are COOH or $CONH_2$, $Ar^2$, Z, $R^2$ and n' have the same meanings as given above in general formula I, the corresponding compound of formula I in which $Ar^1$ is a mono-, di- or tri-substituted phenyl group in which the substituents are COOalkyl is hydrolysed or ammonolyzed; optionally, this transformation may take place simultaneously with hydrolysis or ammonolysis of another COOalkyl group of the compound of formula I;

(e) when in formula I, $Ar^1$ is a mono-, di- or tri-substituted phenyl group in which the substituents are COOH, $Ar^2$, Z, $R^2$ and n' have the same meanings as given above in general formula I, the corresponding compound of formula I in which $Ar^1$ is a mono-, di- or tri-substituted phenyl group in which the substituents are CN is hydrolysed; optionally, this transformation may take place simultaneously with the hydrolysis of another CN group of the compound of formula I:

(f) when in formula I, $Ar^1$ is a mono-, di- or tri-substituted phenyl group in which the substituents are CN, $Ar^2$, Z, $R^2$ and n' have the same meanings as given above in general formula I and W is a group of formula $R^1$—$(CH_2)_n$—X—$(CH_2)_m$— wherein $R^1$ represents COOH and n, m and X have the same meaning as stated above for general formula I, the corresponding compound of formula I in which $R^1$ is COOalkyl is hydrolysed, as described in (a2).

(g) when, in formula I, $Ar^1$ is a mono-, di- or tri-substituted phenyl group in which the substituents are $NH_2$ and W is a group of formula $R^1$—$(CH_2)_n$—X—$(CH_2)_m$— wherein $R^1$ represents COOH or COOalkyl, $Ar^2$, Z, $R^2$, n', n, m and X having the same meanings as given above in general formula I, the corresponding compound of formula I in which $Ar^1$ is a mono-, di- or tri-substituted phenyl group in which the substituents are $NO_2$ is reduced. Any conditions known for the reduction of nitro groups into amino groups may be used for this transformation.

(h) when, in formula I, $Ar^1$ is a mono-, di- or tri-substituted phenyl group in which the substituents are OH, W, $Ar^2$, Z, $R^2$ and n' having the same meaning as given above in general formula I, the corresponding compound of formula I in which $Ar^1$ is a mono-, di- or tri-substituted phenyl group in which the substituents are OP', wherein P' is a protecting group, is deprotected. The protecting group P' may be any suitable alcohol protecting group such as, for example, a methoxyethoxymethyl (MEM), a tetrahydropyranyl (THP), an allyl or a benzyl group. For more details concerning deprotection methods, see "Protective Groups in Organic Chemistry", J. F. W. Omie, Plenum Press, London and New York, 1973 and "Protective Groups in Organic Synthesis", Th. W. Greene, John Wiley & Sons, 1981.

(i) optionally, the α-arylethylpiperazine derivative of formula I so-obtained is converted into one of its non-toxic pharmaceutically acceptable salts. The non-toxic pharmaceutically acceptable salts can be prepared from α-arylethylpiperazine derivatives of formula I by methods which are known per se.

The compounds of formula I which are in the form of a mixture of individual optical isomers are either obtained from optically pure starting materials or by separation of a mixture of optical isomers of the compound of general formula I by conventional resolution methods, including chromatographical methods.

The present invention also encompasses compounds of formula II which are useful intermediates for the preparation or compounds of formula I.

The present invention also relates to processes for the manufacture of compounds of formula II.

Compounds of formula II may be prepared by one of the following processes:

(i) Compounds of formula II wherein $Ar^1$ is different from a mono-, di- or tri-substituted phenyl group in which the substituent is $NO_2$, $Ar^2$, Z, $R^2$ and n' having the same meanings as in general formula II, may be obtained by classical deprotection methods of compounds of formula IV

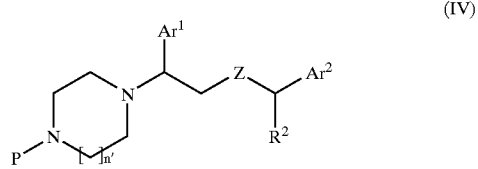

(IV)

in which P represents a protecting group, such as COOEt, tert-butoxycarbonyl or tosyl, or any other known protecting group suitable for a piperazine, $Ar^1$, $Ar^2$, Z, $R^2$ and n' having the same meanings as in formula II. For more details concerning deprotection methods, see "Protective Groups in Organic Chemistry", J. F. W. Omie, Plenum Press, London and New York, 1973 and "Protective Groups in Organic Synthesis, Th. W. Greene, John Wiley & Sons, 1981.

(ii) Compounds of formula II in which Ar1 is a mono-, di- or tri-substituted phenyl group in which the substituent is $NO_2$, $Ar^2$, Z, $R^2$ and n' having the same meanings as in general formula II, may be obtained by nitration of compounds of formula II in which Ar1 is a phenyl group, according to the method described in Lynch B. M., Poon L., Can. J. Chem. (1967), 45, 1431.

Compound of formula IV used for the preparation of compound of formula II may be obtained by the following methods:

when, in formula IV, Z represents O, $Ar^1$, $Ar^2$, Z, n' and P having the same meanings as stated above, a compound of formula V is reacted with an alkylating agent of formula VI according to the equation

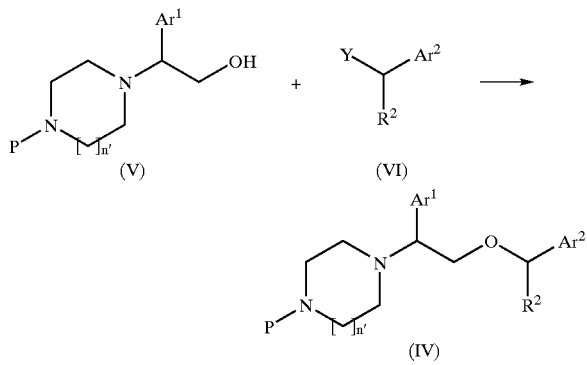

wherein Y represents a leaving group such as a halogen atom, preferably a Chlorine, a Bromine or a Iodine atom, a mesyl, a tosyl or a trichloroacetamidate group, $Ar^1$, $Ar^2$, $R^2$, n' and P having the same meanings as in formula IV. When Y represents a halogen atom, a mesyl or a tosyl group, this reaction is known per se and is generally carried out in an inert organic solvent, for example dimethylformamide or tetrahydrofuran, in the presence of a strong base, such as NaH and in the presence of a catalyst when Y represents a Chlorine or a Bromine atom, for example sodium iodide or potassium iodide. More exactly, the anion of compound of formula V is preformed between 0° C. and room temperature; after addition of compound of formula VI, the mixture is stirred between room temperature and 50° C. When Y represents a trichloroacetamidate group, the O-alkylation of compound of formula V may be carried out in the presence of a strong acid such as trifluoromethane-sulfonic acid as described in patent application WO 97/14671.

when in formula IV Z represents S, $Ar^1$, $Ar^2$, Z, n' and P having the same meanings as in general formula IV, a compound of formula XV is reacted with an alkylating agent of formula XV according to the equation

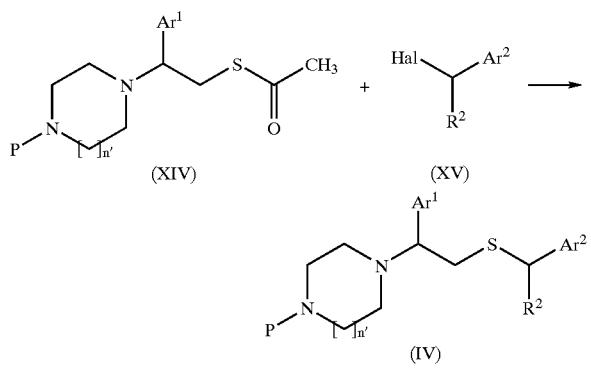

wherein Hal represents a halogen atom, preferably a Bromine atom, $Ar^1$, $Ar^2$, n' and P having the same meanings as stated above. This reaction is generally carried out in an inert solvent, for example toluene, dimethylformamide, an alcohol or an ether, in the presence of an organic base, for example diethylamine or pyrrolidine, or in the presence of an inorganic base, for example NaH, $NaBH_4$, sodium hydroxide, sodium methoxide or potassium hydroxide, between −10 and 50° C.

The starting materials used for the preparation of compounds of formula IV may be prepared according to the following procedures:

compounds of formula V may be obtained according to four differents methods:

1. the reaction of a piperazine of formula VII with an epoxide derivative of formula VIII according to the equation

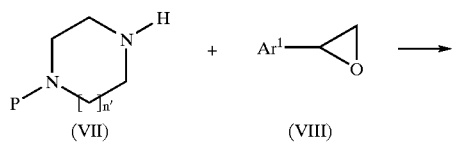

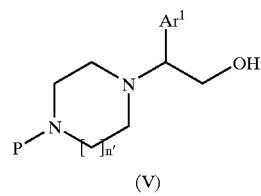

in these formulae, Ar¹, n' and P have the same meanings as stated above.

2. the reduction of compound of formula IX according to the equation

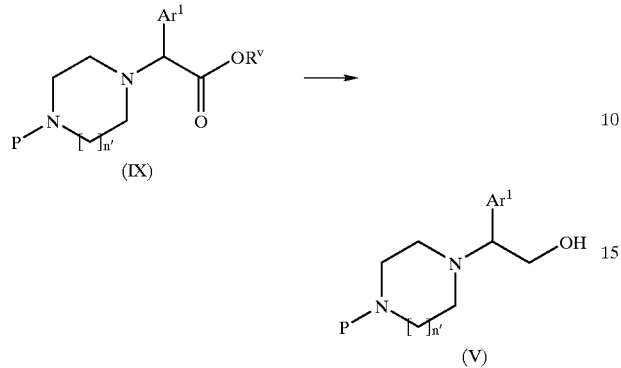

wherein Rv represents a hydrogen atom or an alkyl group, Ar¹, n' and P having the same meanings as stated above.

Compound IX may be obtained by reaction of compounds of formula VII with an α-bromo ester of formula X according to the equation

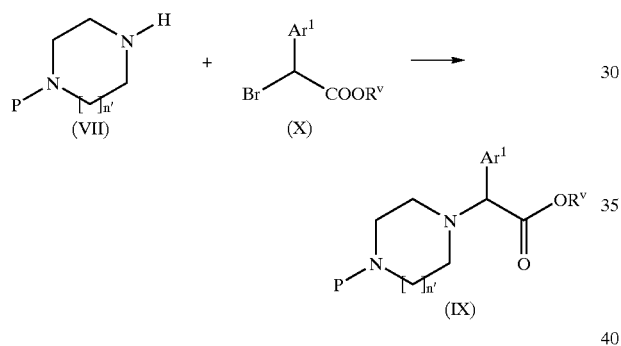

wherein $R^v$ represents a hydrogen atom or an alkyl group, Ar¹, n' and P having the same meanings as stated above.

3. the reaction of a piperazine of formula VII with a heteroaryl boronic acid of formula XI in presence of glyoxylic acid according to the equation

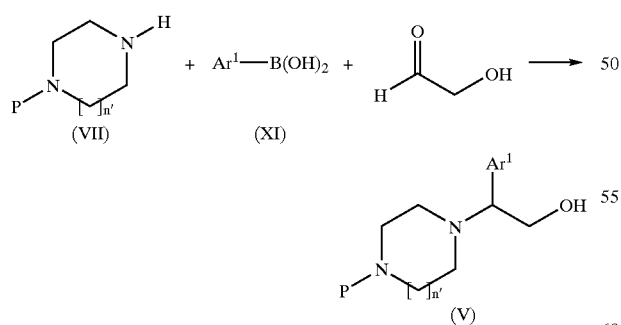

wherein Ar¹, n' and P have the same meanings as stated in formula V (see Petasis N. A. et al., Tetrahedron (1997), 53, 16463–16470).

4. when in formula V P is a tosyl group, Ar¹ and n' having the same meanings as stated above the reaction of the amine of formula XII with a disubstituted N,N-diethyl-4-methylbenzenesulfonamide according to the equation

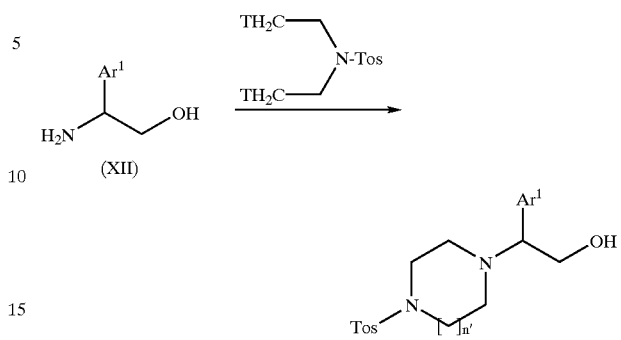

wherein Ar¹ and n' have the same meanings as stated above and T is a Chlorine, Bromine or Iodine atom or (4-methylphenyl)sulfonyloxy or methylsulfonyloxy group. This reaction may be carried out under the conditions disclosed in European Patent Application 617 028 A1. Compounds of formula XII may be obtained by conventional reduction of the corresponding carboxylic acid.

compounds of formula XIV may be obtained by reaction of a compound of formula XVI with a thioacetate salt, for example potassium thioacetate, according to the equation

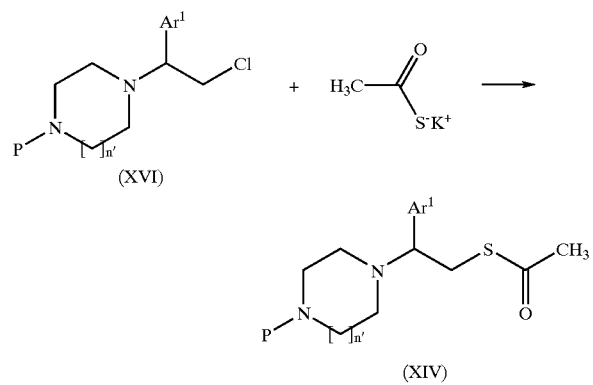

wherein Ar¹, n' and P have the same meanings as stated above. This reaction is carried out in an inert solvent, for example toluene, dimethylformamide, an alcohol, ethyl acetate or dichloromethane between −10° C. and 40° C.

Compounds of formula XVI may be obtained by halogenation of a compound of formula V in presence of thionyl chloride according to the equation

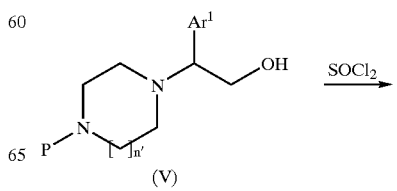

-continued

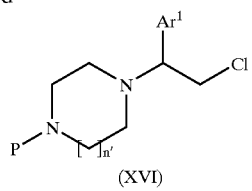

(XVI)

wherein Ar¹, n' and P have the same meanings as stated above.

The following examples illustrate the present invention without limiting it.

Unless specified otherwise in the examples, characterization of the compounds was performed according to the following methods:

NMR spectra were recorded on a BRUKER AC 250 Fourier Transform NMR Spectrometer fitted with an Aspect 3000 computer and with a 5 mm 1H/13C dual probehead. The compound was studied in DMSO (or CDCl3) solution at the probe temperature of 313 K and at a concentration of 20 mg/ml. The instrument was locked on the deuterium signal of DMSO (or CDCl3). Chemical shifts are given in ppm downfield from TMS taken as internal standard.

Mass spectrometric measurements in LC/MS mode were performed as follows:

HPLC Conditions

Analyses were performed using a WATERS Alliance HPLC system mounted with an INERTSIL CHROMPACK 3 ODS, DP 5 μm, 250×4.6 mm column.

The gradient ran from 100% solvent A (acetonitril, water, TFA (10/90/0.1, v/v/v)) to 100% solvent B (acetonitrile, water, TFA (90/10/0.1, v/v/v)) in 7 min with a hold at 100% B of 4 min. The flow rate was set at 2.5 ml/min and a split of 1/10 was used just before API source. The chromatography was carried out at 30° C.

MS Conditions

Samples were dissolved in acetonitrile/water, 70/30, v/v at the concentration of about 250 μgr/ml. API spectra (+ or −) were performed using a FINNIGAN (San Jose, Calif., USA) LCQ ion trap mass spectrometer. APCI source operated at 450° C. and the capillary heater at 160° C. ESI source operated at 3.5 kV and the capillary heater at 210° C.

Mass spectrometric measurements in EI/DIP mode were performed as follows: samples were vaporized by heating the probe from 50° C. to 250° C. in 5 min. EI (Electron Impact) spectra were recorded using a FINNIGAN (San Jose, Calif., USA) TSQ 700 tandem quadrupole mass spectrometer. The source temperature was set at 150° C.

Specific rotation was recorded on a Perlin-Elmer MC241 polarimeter. The angle of rotation was recorded at 25° C. on 1% solutions in MeOH. For some molecules, the solvent was CH2Cl2 or DMSO, due to solubility problems.

Water content is determined using a Metrohm microcoulometric Karl Fischer titrator.

Chromatographic separations are performed on silicagel 60 Merck, particle size 15–40 μm, reference 1.15111.9025.

Unless specified otherwise in the examples, the compounds are obtained as the free bases. The conversion of these free bases into non-toxic pharmaceutically acceptable salts may proceed according to conventional methods known to those skilled in the art. The following general method are given by way of illustration.

For the formation of hydrochlorides or dihydrochlorides of α-arylethylpiperazine derivatives of formula I, free bases were dissolved in an inert solvent, for example CH₂Cl₂, diisopropylether, and a solution of 1,2 or 3 equivalents of HCl in diethylether was added. The volatile substances were removed and the product was recrystallized, usually, from CH₃CN. The salts could also be obtained directly from acidic hydrolysis in the last step and the solid products might be obtained by lyophilisation. The exact salt composition of the product was determined by elemental analysis. The exact quantity of water was determined by Karl Fischer method.

For the formation of the maleates or dimaleate of α-arylethylpiperazine derivatives of formula I, free bases were dissolved in 2-butanone and 1 or 2 equivalents of maleic acid were added. The solids were filtered and the products recrystallized from CH₃CN. The exact salt composition of the product was determined by elemental analysis. The exact quantity of water was determined by Karl Fischer method.

In the following examples, when the molecule contains one asymetric center, NSA and NSB are individual optical isomers for which absolute configuration has not been determined;

when the molecule contains two asymmetric centers, NSA and NSB refer to couple of enantiomers of which the absolute configuration has not been determined; when the absolute configuration has been determined for one or for the two asymmetric centers, the first R, S or rac. symbol refers to the absolute configuration of the Carbon atom which bears Ar1, and the second R, S or rac. symbol refers to the absolute configuration of the other asymmetric center.

EXAMPLE 1

Preparation of Compounds of Formula I According to Process (a)

1.1. Preparation of Compounds of Formula V

Method 1.

In a round-bottomed flask fitted with a reflux condenser and a thermometer, 15 g (125 mmoles) of (R)-phenyloxirane, 19.75 g (125 mmoles, 18.3 ml) of ethyl-N-piperazine carboxylate, and 80 ml of ethyl alcohol were introduced. The mixture was heated at reflux for 3 hours. Volatile substances were removed under reduced pressure and the resulting mixture was purified by chromatography on silica gel (eluent: CH₂Cl₂/MeOH/aqueous ammonia 98.5/1.5/0.5 (v/v/v)), affording 8.8 g of (S)-4-(2-Hydroxy-1-phenyl-ethyl)-piperazine-1-carboxylic acid ethyl ester (compound 2) as a colorless oil. Yield: 25%.

The compounds of formula V presented in Table I were prepared according to this method.

TABLE I

Compounds of formula V obtained by Method 1.

| Cpd No. | P | n' | Ar¹ | stereochemistry |
|---|---|---|---|---|
| 1 | COOEt | 1 | phenyl | racemic |
| 3 | COOEt | 1 | phenyl | R |
| 4 | COOEt | 1 | 4-methylphenyl | racemic |
| 5 | COOEt | 1 | 4-fluorophenyl | racemic |
| 6 | COOEt | 1 | 1-naphthyl | racemic |
| 7 | COOEt | 1 | 2-naphthyl | racemic |

The starting oxiranes used for the preparation of compounds 4 to 7 may be obtained by the method disclosed in Bouha H. et al., Synthetic Communications (1987), 17(5), 503–513.

Method 2.

In a round-bottomed flask fitted with a reflux condenser and a thermometer 62.8 g (397 mmoles) of ethyl N-piperazinecarboxylate, 60.3 g (596 mmoles) of triethylamine, and 1980 ml of methyl alcohol were introduced; 109.3 g (477 mmoles) of methyl-1-bromo-1-phenylacetate were added dropwise to this mixture. The solution was heated at reflux for 24 hours. The volatile substances were removed under reduced pressure; 700 ml of methylene chloride were added to the residue; the mixture was filtered and the organic phase was washed with water and then with brine, dried over magnesium sulfate, and concentrated under reduced pressure, affording 114 g of 4-(Methoxycarbonyl-phenyl-methyl)-piperazine-1-carboxylic acid ethyl ester as an oil. Yield: 94%.

In a round-bottomed flask fitted in a reflux condenser and a thermometer 57.0 g (186 mmoles) of 4-(Methoxycarbonyl-phenyl-methyl)-piperazine-1-carboxylic acid ethyl ester obtained above and 660 ml of THF were introduced under nitrogen. The solution was cooled to −20° C., and 7.0 g (185 mmoles) of lithium aluminium hydride were added portionwise. The reaction mixture was stirred at −15° C. for 45 min, cooled to −35° C.; 7 ml of a 15% (w/w) solution of sodium hydroxide in water and 21 ml of water were successively added to the reaction mixture. The mixture was filtered, the precipitate was washed with THF, and the combined organic phases were concentrated under reduced pressure. The residue was dissolved in methylene chloride (1 l) and the solution was washed with water and then brine. The organic phase was dried over magnesium sulfate and concentrated under reduced pressure, affording 47.2 g of an oil. This oil was purified by chromatography on silica gel (eluent: methylene chloride-aqueous ammonia 98.5/1.5/0.15 (v/v/v)) affording 34.6 g of 4-(2-hydroxy-1-phenyl-ethyl)-piperazine-1-carboxylic acid ethyl ester (compound 1) as a yellow oil. Yield: 67%.

The compounds of formula V identified in Table II were prepared according to this method.

TABLE II

Compounds of formula V obtained by Method 2.

| Cpd No. | P | n' | Ar$^1$ | stereo-chemistry |
|---|---|---|---|---|
| 8 | Boc | 1 | phenyl | racemic |
| 9 | COOEt | 1 | 3,5-(bistrifluoromethyl)-phenyl | racemic |
| 10 | COOEt | 1 | 4-bromophenyl | racemic |
| 11 | COOEt | 1 | 3-chlorophenyl | racemic |
| 12 | COOEt | 1 | 3,4-dichlorophenyl | racemic |
| 15 | COOEt | 1 | 2,3-difluorophenyl | racemic |
| 16 | COOEt | 1 | 3,4,5-trifluorophenyl | racemic |
| 17 | Boc | 2 | phenyl | racemic |

The starting alkylating agents used for the preparation of compounds 9 to 12 and 16 may be obtained by the method described in Carini D. J. et al., J. Med. Chem. (1990), 33, 1330–1336.

The enantiomers of compound 12, compound 13 (NSA) and compound 14 (NSB), were obtained by resolution by chiral chromatography (Chiralcel OD, 226 nm, 23° C. Eluent: iPrOH 17.5%, benzine 82.5%+DEA 0.1%), compound 13 being the compound that elutes the fastest.

Method 3.

Following the procedure described in Petasis N. A. et al. in Tetrahedron (1997), 53, 16463–16470, ethyl-N-piperazine carboxylate was reacted with 3-isopropylphenyl-boron dihydroxide in the presence of glycolaldehyde to provide 4-[2-hydroxy-1-(3-isopropyl-phenyl)-ethyl]-piperazine-1-carboxylic acid ethyl ester (compound 18). The compounds listed in Table III were obtained by the same method.

TABLE III

Compounds of formula V obtained by Method 3.

| Cpd No. | P | n' | Ar$^1$ | stereo-chemistry |
|---|---|---|---|---|
| 19 | COOEt | 1 | 4-methoxyphenyl | racemic |
| 20 | COOEt | 1 | thiophen-2-yl | racemic |
| 21 | COOEt | 1 | thiophen-3-yl | racemic |
| 22 | COOEt | 1 | furan-2-yl | racemic |
| 23 | COOEt | 1 | benzo[c]thiophen-1-yl | racemic |
| 24 | COOEt | 1 | isobenzofuran-1-yl | racemic |

Method 4.

2-Phenyl-2-[4-(toluene-4-sulfonyl)-piperazin-1-yl]-ethanol (compound 25) was obtained from 2-phenylethan-1-olamine and N,N-bis(chloroethyl)-4-methylbenzenesulfonamide following the method described in European Patent Application 617 028 A1. When starting from (S) or (R) 2-phenylethan-1-olamine, the corresponding (S) or (R) 2-Phenyl-2-[4-(toluene-4-sulfonyl)-piperazin-1-yl]-ethanol (compounds 26 and 27, respectively) were obtained.

1.2. Preparation of Compounds of Formula IV 1.2.1. Preparation of compounds of formula IV wherein Z is O.

In a round-bottomed flask fitted with a reflux condenser and a thermometer 8.8 g (32 mmoles) of (S)-4-(2-Hydroxy-1-phenyl-ethyl)-piperazine-1-carboxylic acid ethyl ester (compound 2 prepared at example 1.1) and 50 ml of THF were introduced. The solution was cooled to 0° C. and 1.5 g of sodium hydride (47 mmoles, 78% in parafin) were added portionwise. The solution was allowed to reach room temperature and was stirred for 30 minutes. The solution was cooled again to 0° C., and a solution of 8.5 g (32 mmoles) of 3,5-bis-(trifluoromethyl)-benzyl chloride in 20 ml of THF was added dropwise. Sodium iodide (4.7 g, 32 mmoles) was added to the mixture, which was then stirred at room temperature for 24 hours. The mixture was then cooled to 0° C. and the reaction was quenched with 20 ml of aqueous ammonium chloride. The volatile substances were removed under reduced pressure, 100 ml of water were added, and the pH was adjusted to 11 by addition of aqueous sodium hydroxide. The mixture was extracted with diethyl ether, the organic phase was dried over magnesium sulfate, and concentrated under reduced pressure, affording 15.4 g of an oil. This oil was purified by chromatography on silica gel (eluent: methylene chloride-methanol-aqueous ammonia 99/1/0.5 (v/v/v)), affording 9.5 g of (S)-4-[2-(3,5-bis-[trifluoromethyl]-benzyloxy)-1-phenyl-ethyl]-piperazine-1-carboxylic acid ethyl ester (compound 30) as a yellow oil. Yield: 60%.

The compounds listed in Table IV were obtained by the same method. When R$^3$ represents CH$_3$, the starting alkylating agents used according to this method may be obtained by the method disclosed in Owens A. P. et al., Bio. Med. Chem. Lett. (1995), 5, 2761–2766.

TABLE IV

Preparation of compounds of formula IV wherein Z is O

| Cpd No. | P | n' | R² | Ar¹ | Ar² | stereo-chemistry | starting cpd No. |
|---|---|---|---|---|---|---|---|
| 28 | Boc | 1 | H | phenyl | 3,5-bis(trifluoromethyl)phenyl | racemic | 8 |
| 29 | COOEt | 1 | H | phenyl | 3,5-bis(trifluoromethyl)phenyl | racemic | 1 |
| 31 | COOEt | 1 | H | phenyl | 3,5-bis(trifluoromethyl)phenyl | R | 3 |
| 32 | Tos | 1 | H | phenyl | 3,5-bis(trifluoromethyl)phenyl | racemic | 25 |
| 33 | Tos | 1 | H | phenyl | 3,5-bis(trifluoromethyl)phenyl | S | 26 |
| 34 | Tos | 1 | H | phenyl | 3,5-bis(trifluoromethyl)phenyl | R | 27 |
| 35 | COOEt | 1 | H | 4-methylphenyl | 3,5-bis(trifluoromethyl)phenyl | racemic | 4 |
| 36 | COOEt | 1 | H | 3-isopropylphenyl | 3,5-bis(trifluoromethyl)phenyl | racemic | 18 |
| 37 | COOEt | 1 | H | 4-methoxyphenyl | 3,5-bis(trifluoromethyl)phenyl | racemic | 19 |
| 38 | COOEt | 1 | H | 3-chlorophenyl | 3,5-bis(trifluoromethyl)phenyl | racemic | 11 |
| 39 | COOEt | 1 | H | 4-bromophenyl | 3,5-bis(trifluoromethyl)phenyl | racemic | 10 |
| 40 | COOEt | 1 | H | 4-fluorophenyl | 3,5-bis(trifluoromethyl)phenyl | racemic | 5 |
| 41 | COOEt | 1 | H | 3,4-dichlorophenyl | 3,5-bis(trifluoromethyl)phenyl | racemic | 12 |
| 42 | COOEt | 1 | H | 3,4-dichlorophenyl | 3,5-bis(trifluoromethyl)phenyl | NSA | 13 |
| 43 | COOEt | 1 | H | 3,4-dichlorophenyl | 3,5-bis(trifluoromethyl)phenyl | NSB | 14 |
| 44 | COOEt | 1 | H | 2,3-difluorophenyl | 3,5-bis(trifluoromethyl)phenyl | racemic | 15 |
| 45 | COOEt | 1 | H | 3,4,5-trifluorophenyl | 3,5-bis(trifluoromethyl)phenyl | racemic | 16 |
| 46 | COOEt | 1 | H | 1-naphthyl | 3,5-bis(trifluoromethyl)phenyl | racemic | 6 |
| 47 | COOEt | 1 | H | 2-naphthyl | 3,5-bis(trifluoromethyl)phenyl | racemic | 7 |
| 48 | COOEt | 1 | H | thiophen-2-yl | 3,5-bis(trifluoromethyl)phenyl | racemic | 20 |
| 49 | COOEt | 1 | H | thiophen-3-yl | 3,5-bis(trifluoromethyl)phenyl | racemic | 21 |
| 50 | COOEt | 1 | H | furan-2-yl | 3,5-bis(trifluoromethyl)phenyl | racemic | 22 |
| 51 | COOEt | 1 | H | benzo[c]thiophen-1-yl | 3,5-bis(trifluoromethyl)phenyl | racemic | 23 |
| 52 | COOEt | 1 | H | isobenzofuran-1-yl | 3,5-bis(trifluoromethyl)phenyl | racemic | 24 |
| 53 | COOEt | 1 | H | phenyl | 2,4-bis(trifluoromethyl)phenyl | racemic | 1 |
| 54 | COOEt | 1 | H | phenyl | 3,5-dimethylphenyl | racemic | 1 |
| 55 | COOEt | 1 | H | phenyl | 3,5-bis(tert-butyl)phenyl | racemic | 1 |
| 56 | COOEt | 1 | H | phenyl | 2-methoxyphenyl | racemic | 1 |
| 57 | COOEt | 1 | H | phenyl | 3-isopropoxyphenyl | racemic | 1 |
| 58 | COOEt | 1 | H | phenyl | 2-trifluoromethoxyphenyl | racemic | 1 |
| 59 | COOEt | 1 | H | phenyl | 3,4,5-trimethoxyphenyl | racemic | 1 |
| 60 | Tos | 1 | H | phenyl | 3-chlorophenyl | racemic | 25 |
| 61 | COOEt | 1 | H | phenyl | 3,5-dichlorophenyl | racemic | 1 |
| 62 | Tos | 1 | H | phenyl | 3,5-dichlorophenyl | S | 26 |
| 63 | Tos | 1 | H | phenyl | 3,5-dichlorophenyl | R | 27 |
| 64 | COOEt | 1 | H | phenyl | 3,4-dichlorophenyl | racemic | 1 |
| 65 | Tos | 1 | H | phenyl | 3,5-dibromophenyl | racemic | 25 |
| 66 | Tos | 1 | H | phenyl | 3,5-difluorophenyl | racemic | 25 |
| 67 | Boc | 1 | H | phenyl | 3-bromo-5-iodophenyl | racemic | 8 |
| 68 | Boc | 1 | H | phenyl | 3,5-dichloro-4-methoxyphenyl | racemic | 8 |
| 69 | COOEt | 1 | H | 3,5-bis(trifluoromethyl)phenyl | phenyl | racemic | 9 |
| 70 | COOEt | 1 | CH3 | phenyl | 3,5-bis(trifluoromethyl)phenyl | racemic | 1 |
| 73 | Tos | 1 | CH3 | phenyl | 3,5-bis(trifluoromethyl)phenyl | racemic | 25 |
| 76 | Tos | 1 | CH3 | phenyl | 3,5-bis(trifluoromethyl)phenyl | S, rac. | 26 |
| 79 | Tos | 1 | CH3 | phenyl | 3,5-bis(trifluoromethyl)phenyl | R, rac. | 27 |
| 82 | Boc | 2 | H | phenyl | 3,5-bis(trifluoromethyl)phenyl | racemic | 17 |

The following racemic mixtures were resolved into their isomers by chromatographic separation on silica gel 60 or on chiral stationary phases:
- compound 70: stationary phase: silica gel 60; eluent: CH₂Cl₂; the individual enantiomers so-obtained will be referred to as compounds 71 (NSA) and 72 (NSB), 71 being the compound that elutes the fastest under the given conditions;
- compound 73: stationary phase: silica gel 60; eluent: benzine 40%, CH₂Cl₂ 60%; the individual isomers so-obtained will be referred to as compounds 74 (NSA) and 75 (NSB), 74 being the compound that elutes the fastest.
- compound 76: stationary phase: CHIRALPAK AD, detection at 226 nm; temperature 20° C.; eluent: ethanol 5%, benzine 95%, diethylamine 0.1%; the individual diastereoisomers so-obtained will be referred to as compounds 77 (S,R) and 78 (S,S), 77 being the compound that elutes the fastest.
- compound 79: stationary phase: silica gel 60; eluent: benzine 40%, CH₂Cl₂ 60%; the individual diastereoisomers so-obtained will be referred to as compounds 80 (R,R) and 81 (R,S), 80 being the compound that elutes the slowest.

1.2.2. Preparation of compounds of formula IV wherein Z is S.

a. In a round-bottomed flask fitted with a reflux condenser and a thermometer 6.3 g (17.5 mmoles) of 2-phenyl-2-[4-(toluene-4-sulfonyl)-piperazin-1-yl]-ethanol (compound 25 prepared at example 1.1) and 20 ml of methanol are introduced. An excess of 3 N methanolic HCl is added dropwise, the volatile substances are removed under reduced pressure, affording the dihydrochloride salt of 2-phenyl-2-[4-(toluene-4-sulfonyl)-piperazin-1-yl]-ethanol. To the salt are added 250 ml of CHCl₃, the mixture is cooled to 0° C., and 4.7 g (39.5 mmoles) of SOCl₂ are added dropwise. After completion of the addition, the mixture is heated at reflux for 3 hours. The volatile substances are removed under reduced pressure, affording crude 1-(2-chloro-1-phenyl-ethyl)-4-(toluene-4-sulfonyl)-piperazine as an oil. Ethyl alcohol (300 ml), 2.5 g (22.2 mmoles) of potassium thioacetate, and 3.07 g (22.2 mmoles) of potassium carbonate are then added to this crude product. The mixture is stirred for 16 hours, and the volatile substances are removed under reduced pressure. 150 ml of ether and 150 ml of water are added to the residue, and the mixture is filtered, affording the crude thioacetic acid S-{2-phenyl-2-[4-(toluene-4-sulfonyl)-piperazin-1-yl]-ethyl}ester (compound 83) as a white solid. The aqueous phase is extracted three times with methylene chloride. The solid is dissolved in methylene chloride, the methylene chloride solutions are combined and washed with brine, dried over magnesium sulfate and concentrated under reduced pressure, affording 4.32 gr of compound 83 as a white solid. Yield: 59%.

b. In a round-bottomed flask fitted with a reflux condenser and a thermometer 2.76 g (6.6 mmoles) of thioacetate 83 and 250 ml of degassed methyl alcohol are introduced. The mixture is cooled to 0° C. and 356 mg (6.6 mmoles) of sodium methylate are added. The mixture is stirred under argon for one hour at 0° C., and 1.9 g (7.26 mmoles) of 3,5-bis-trifluoromethyl-benzyl bromide are added. The mixture is stirred for 48 hours, volatile substances are removed under reduced pressure, and 100 ml of water are added. The aqueous phase is extracted three times with methylene chloride, the combined organic phases are washed with brine and dried over magnesium sulfate. Volatile substances are removed under reduced pressure, affording 4.54 g of crude 1-[2-(3,5-bis-trifluoromethyl-benzylsulfanyl)-1-phenyl-ethyl]-4-(toluene-4-sulfonyl)-piperazine (compound 84) as a colorless oil. This oil was purified by chromatography on silica gel (eluent: methylene chloride-hexane 65/35 (v/v)), affording 3.26 g of compound 84 as a colorless oil. Yield: 82%.

1-[2-(3,5-Dimethyl-benzylsulfanyl)-1-phenyl-ethyl]-4-(toluene-4-sulfonyl)-piperazine (compound 85) was obtained by the same method.

1.3. Preparation of Compounds of Formula II 1.3.1. Preparation of compounds of formula II wherein Ar1 is not a mono-, di- or tri-substituted phenyl group in which the substituent is $NO_2$.

The compounds of formula II summarized in Table V are obtained by classical deprotection methods of corresponding compounds of formula IV. For more details concerning deprotection methods, see "Protective Groups in Organic Chemistry", J. F. W. Omie, Plenum Press, London and New York, 1973 and "Protective Groups in Organic Synthesis, Th. W. Greene, John Wiley & Sons, 1981.

Physico-chemical properties of the compounds of formula II prepared according to this method are given in Table Va below. When the compounds of formula II are in the form of non toxic pharmaceutically acceptable salts, they are obtained by the general method stated above.

TABLE V

Preparation of compounds of formula II by deprotection of compounds of formula IV

| Cpd No. | n' | R2 | Ar$^1$ | Ar$^2$ | Z | Stereo-chemistry | Starting cpd No. |
|---|---|---|---|---|---|---|---|
| 86 | 1 | H | phenyl | 3,5-bis(trifluoromethyl)phenyl | O | racemic | 28, 29 or 32 |
| 87 | 1 | H | phenyl | 3,5-bis(trifluoromethyl)phenyl | O | S | 30 or 33 |
| 88 | 1 | H | phenyl | 3,5-bis(trifluoromethyl)phenyl | O | R | 31 or 34 |
| 89 | 1 | H | 4-methylphenyl | 3,5-bis(trifluoromethyl)phenyl | O | racemic | 35 |
| 90 | 1 | H | 3-isopropylphenyl | 3,5-bis(trifluoromethyl)phenyl | O | racemic | 36 |
| 91 | 1 | H | 4-methoxyphenyl | 3,5-bis(trifluoromethyl)phenyl | O | racemic | 37 |
| 92 | 1 | H | 3-chlorophenyl | 3,5-bis(trifluoromethyl)phenyl | O | racemic | 38 |
| 93 | 1 | H | 4-bromophenyl | 3,5-bis(trifluoromethyl)phenyl | O | racemic | 39 |
| 94 | 1 | H | 4-fluorophenyl | 3,5-bis(trifluoromethyl)phenyl | O | racemic | 40 |
| 95 | 1 | H | 3,4-dichlorophenyl | 3,5-bis(trifluoromethyl)phenyl | O | racemic | 41 |
| 96 | 1 | H | 3,4-dichlorophenyl | 3,5-bis(trifluoromethyl)phenyl | O | NSA | 42 |
| 97 | 1 | H | 3,4-dichlorophenyl | 3,5-bis(trifluoromethyl)phenyl | O | NSB | 43 |
| 98 | 1 | H | 2,3-difluorophenyl | 3,5-bis(trifluoromethyl)phenyl | O | racemic | 44 |
| 99 | 1 | H | 3,4,5-trifluorophenyl | 3,5-bis(trifluoromethyl)phenyl | O | racemic | 45 |
| 100 | 1 | H | 1-naphthyl | 3,5-bis(trifluoromethyl)phenyl | O | racemic | 46 |
| 101 | 1 | H | 2-naphthyl | 3,5-bis(trifluoromethyl)phenyl | O | racemic | 47 |
| 102 | 1 | H | thiophen-2-yl | 3,5-bis(trifluoromethyl)phenyl | O | racemic | 48 |
| 103 | 1 | H | thiophen-3-yl | 3,5-bis(trifluoromethyl)phenyl | O | racemic | 49 |
| 104 | 1 | H | furan-2-yl | 3,5-bis(trifluoromethyl)phenyl | O | racemic | 50 |
| 105 | 1 | H | benzo[c]thiophen-1-yl | 3,5-bis(trifluoromethyl)phenyl | O | racemic | 51 |
| 106 | 1 | H | isobenzofuran-1-yl | 3,5-bis(trifluoromethyl)phenyl | O | racemic | 52 |
| 107 | 1 | H | phenyl | 2,4-bis(trifluoromethyl)phenyl | O | racemic | 53 |
| 108 | 1 | H | phenyl | 3,5-dimethylphenyl | O | racemic | 54 |
| 109 | 1 | H | phenyl | 3,5-bis(tert-butyl)phenyl | O | racemic | 55 |
| 110 | 1 | H | phenyl | 2-methoxyphenyl | O | racemic | 56 |
| 111 | 1 | H | phenyl | 3-isopropoxyphenyl | O | racemic | 57 |
| 112 | 1 | H | phenyl | 2-trifluoromethoxyphenyl | O | racemic | 58 |
| 113 | 1 | H | phenyl | 3,4,5-trimethoxyphenyl | O | racemic | 59 |
| 114 | 1 | H | phenyl | 3-chlorophenyl | O | racemic | 60 |
| 115 | 1 | H | phenyl | 3,5-dichlorophenyl | O | racemic | 61 |
| 116 | 1 | H | phenyl | 3,5-dichlorophenyl | O | S | 62 |
| 117 | 1 | H | phenyl | 3,5-dichlorophenyl | O | R | 63 |
| 118 | 1 | H | phenyl | 3,4-dichlorophenyl | O | racemic | 64 |
| 119 | 1 | H | phenyl | 3,5-dibromophenyl | O | racemic | 65 |
| 120 | 1 | H | phenyl | 3,5-difluorophenyl | O | racemic | 66 |
| 121 | 1 | H | phenyl | 3-bromo-5-iodophenyl | O | racemic | 67 |
| 122 | 1 | H | phenyl | 3,5-dichloro-4-methoxyphenyl | O | racemic | 68 |
| 123 | 1 | H | 3,5-bis(trifluoromethyl)phenyl | phenyl | O | racemic | 69 |
| 124 | 1 | CH3 | phenyl | 3,5-bis(trifluoromethyl)phenyl | O | NSA | 71 |
| 125 | 1 | CH3 | phenyl | 3,5-bis(trifluoromethyl)phenyl | O | NSB | 72 or 75 |
| 126 | 1 | CH3 | phenyl | 3,5-bis(trifluoromethyl)phenyl | O | S, R | 77 |
| 127 | 1 | CH3 | phenyl | 3,5-bis(trifluoromethyl)phenyl | O | S, S | 78 |

TABLE V-continued

Preparation of compounds of formula II by deprotection of compounds of formula IV

| Cpd No. | n' | R2 | Ar$^1$ | Ar$^2$ | Z | Stereo-chemistry | Starting cpd No. |
|---|---|---|---|---|---|---|---|
| 128 | 1 | CH3 | phenyl | 3,5-bis(trifluoromethyl)phenyl | O | R, R | 80 |
| 129 | 1 | CH3 | phenyl | 3,5-bis(trifluoromethyl)phenyl | O | R, S | 81 |
| 130 | 2 | H | phenyl | 3,5-bis(trifluoromethyl)phenyl | O | racemic | 82 |
| 131 | 1 | H | phenyl | 3,5-bis(trifluoromethyl)phenyl | S | racemic | 84 |
| 132 | 1 | H | phenyl | 3,5-dimethylphenyl | S | racemic | 85 |

TABLE Va

Physico-chemical properties of compounds of formula II.

| Cpd No. | Free base/salt | Physico-chemical properties |
|---|---|---|
| 86 | | $^1$H-NMR (DMSO): 7.94 (s, 1H), 7.85 (s, 2H), 7.4–7.2 (m, 5H), 4.65 (s, 2H), 3.92 (dd, 1H), 3.78 (dd, 1H), 3.59 (t, 1H), 2.75–2.55 (m, 4H), 2.45–2.2 (m, 4H). Mass: (LC/MS APCI+): 433 (MH+). |
| 90 | 2 HCl·¾ H$_2$O | $^1$H-NMR (DMSO): 8.02 (s, 1H), 7.94 (s, 2H), 7.37 (s, 1H), 7.34 (m, 2H), 7.31 (t, 1H), 4.74 (s, 2H), 4.59 (m, 1H), 4.32 (m, 1H), 4.05 (m, 1H), 3.41 (m, 8H), 2.89 (m, 1H), 1.21 (d, 6H). Mass: (LC/MS APCI+): 475 (MH+). |
| 91 | 2 HCl·1 H$_2$O | $^1$H-NMR (DMSO): 7.91 (s, 1H), 7.84 (s, 2H), 7.4 (d, 2H), 6.95 (d, 2H), 4.7 (dd, 2H), 4.47 (t, 1H), 4.1–3.9 (m, 2H), 3.73 (s, 3H), 3.4–3.2 (m, 6H), 3.2–3.05 (m, 2H). Mass: (LC/MS APCI+): 463 (MH+). |
| 92 | 2 maleate | $^1$H-NMR (DMSO): 7.9 (s, 1H), 7.75 (s, 2H), 7.35–7.2 (m, 4H), 6.18 (s, 4H), 4.6 (s, 2H), 4.0–3.65 (m, 3H), 3.0 (m, 4H), 2.6 (m, 4H). Mass: (LC/MS APCI+): 467/469 (MH+). |
| 94 | 2 HCl·⅔ H$_2$O | $^1$H-NMR (DMSO): 7.91 (s, 1H), 7.81 (s, 2H), 7.52 (dd, 2H), 7.2 (d + d, 2H), 4.75 (s, 2H), 4.44 (t, 1H), 4.1–3.95 (m, 2H), 3.4–3.2 (m, 6H), 3.2–3.05 (m, 2H). Mass: (LC/MS APCI+): 451 (MH+). |
| 95 | 2 HCl | $^1$H-NMR (DMSO): 7.91 (s, 1H), 7.76 (s, 2H), 7.64 (d, 1H), 7.58 (d, 1H), 7.38 (dd, 1H), 4.65 (s, 2H), 4.08 (t, 1H), 3.91 (d, 2H), 3.25–3.15 (m, 4H), 3.0–2.7 (m, 4H). Mass: (LC/MS APCI+): 501/503/505 (MH+). |
| 98 | 1 maleate | $^1$H-NMR (DMSO): 8.2 (s, 2H), 8.0 (s, 1H), 7.8 (s, 2H), 7.3 (m, 1H), 7.2 (m, 2H), 6.0 (s, 2H), 4.7 (m, 2H), 4.2 (m, 1H), 4.0 (m, 1H), 3.9 (m, 1H), 2.0–2.5 (m, 8H). Mass: (LC/MS APCI+): 469 (MH+). |
| 100 | 2 HCl | $^1$H-NMR (DMSO): 8.21 (d, 1H), 7.92 (d, 2H), 7.83 (s, 1H), 7.7 (d + s, 3H), 7.6–7.4 (m, 3H), 5.05 (t, 1H), 4.64 (s, 2H), 4.15–3.95 (m, 2H), 3.85–3.65 (m, 6H), 3.15–2.95 (m, 2H). Mass: (EI/DIP): 482 (M+). |
| 101 | | $^1$H-NMR (CDCl3): 7.82 (dd, 3H), 7.74 (s, 2H), 7.65 (s, 2H), 7.45 (dd, 3H), 4.57 (s, 2H), 3.95 (dd, 1H), 3.85 (dd, 1H), 3.72 (t, 1H), 2.95 (m, 4H), 2.6–2.4 (m, 4H). Mass: (LC/MS APCI+): 483 (MH+). |
| 107 | | $^1$H-NMR (DMSO): 7.97 (d, 1H), 7.92 (s, 1H), 7.75 (d, 1H), 7.35–7.15 (m, 5H), 4.7 (s, 2H), 3.92 (dd, 1H), 3.78 (dd, 1H), 3.57 (t, 1H), 2.75–2.55 (m, 4H), 2.45–2.2 (m, 4H). Mass: (LC/MS APCI+): 433 (MH+). |
| 108 | | $^1$H-NMR (DMSO): 7.35–7.15 (m, 5H), 6.87 (s, 1H), 6.79 (s, 2H), 4.43 (s, 2H), 3.78 (dd, 1H), 3.66 (dd, 1H), 3.53 (t, 1H), 2.75–2.55 (m, 4H), 2.45–2.2 (m, 4H), 2.22 (s, 6H). Mass: (LC/MS APCI+): 325 (MH+). |
| 109 | 2 maleate | $^1$H-NMR (DMSO): 7.29 (m, 5H), 7.24 (s, 1H), 6.99 (s, 2H), 6.17 (s, 2H), 4.40 (m, 1H), 3.95–3.6 (m, 4H), 3.04 (m, 4H), 2.65–2.5 (m, 4H), 1.19 (s, 9H). Mass: (LC/MS APCI+): 409 (MH+). |
| 110 | | $^1$H-NMR (DMSO): 7.35–7.15 (m, 7H), 6.95 (d, 1H), 6.88 (t, 1H), 4.44 (s, 2H), 3.9–3.6 (m, 2H), 3.75 (s, 1H), 3.55 (t, 1H), 3.41 (s, 3H), 2.75–2.55 (m, 4H), 2.45–2.2 (m, 4H). Mass: (LC/MS APCI+): 327 (MH+). |
| 112 | | $^1$H-NMR (DMSO): 7.45–7.15 (m, 9H), 4.55 (s, 2H), 3.85 (dd, 1H), 3.75 (dd, 1H), 3.55 (t, 1H), 2.75–2.55 (m, 4H), 2.45–2.2 (m, 4H). Mass: (LC/MS APCI+): 381 (MH+). |

TABLE Va-continued

Physico-chemical properties of compounds of formula II.

| Cpd No. | Free base/salt | Physico-chemical properties |
|---|---|---|
| 113 | | $^1$H-NMR (DMSO): 7.35–7.2 (m, 5H), 6.51 (d, 2H), 4.36 (d, 2H), 3.9–3.5 (m, 3H), 3.71 (s, 6H), 3.64 (s, 3H), 3.0–2.4 (m, 8H). Mass: (LC/MS APCI+): 387 (MH+). |
| 114 | 2 HCl | $^1$H-NMR (DMSO): 7.4–7.25 (m, 9H), 4.45 (s, 2H), 3.85 (m, 1H), 3.8–3.55 (m, 2H), 3.7–3.1 (m, 8H). Mass: (LC/MS APCI): 331/333 (MH+). |
| 115 | 2 HCl | $^1$H-NMR (DMSO): 7.55–7.4 (m, 5H), 7.4 (s, 1H), 7.25 (s, 2H), 4.53 (dd, 2H), 4.45 (t, 1H), 4.1–3.8 (m, 2H), 3.4–3.2 (m, 6H), 3.2–3.0 (m, 2H). Mass: (LC/MS APCI+): 365/367/369 (MH+). |
| 118 | | $^1$H-NMR (DMSO): 7.55 (d, 1H), 7.4 (d, 1H), 7.4–7.15 (m, 6H), 4.45 (s, 2H), 3.85 (dd, 1H), 3.73 (dd, 1H), 3.55 (t, 1H), 2.75–2.55 (m, 4H), 2.45–2.2 (m, 4H). Mass: (LC/MS APCI+): 365/367/369 (MH+). |
| 119 | 2 HCl | $^1$H-NMR (DMSO): 7.65 (s, 1H), 7.4 (m, 6H), 4.52 (s, 2H), 4.41 (t, 1H), 4.1–3.9 (m, 2H), 3.5–3.2 (m, 6H), 3.2–3.0 (m, 2H). Mass: (LC/MS APCI): 453/455/457 (MH+). |
| 120 | 2 HCl | $^1$H-NMR (DMSO): 7.65 (m, 1H), 7.45 (m, 2H), 7.2–7.0 (m, 5H), 4.7–4.5 (m, 1H), 4.6 (s, 2H), 4.3 (m, 1H), 4.0 (m, 1H), 3.6–3.1 (m, 8H). Mass: (LC/MS APCI): 333 (MH+). |
| 121 | 1 maleate | $^1$H-NMR (DMSO): 7.8 (s, 1H), 7.6 (s, 1H), 7.4 (s, 1H), 7.3 (m, 5H), 6.1 (s, 2H), 4.5 (s, 2H), 3.8 (m, 3H), 2.6–3.0 (m, 8H). Mass: (LC/MS APCI): 501/503 (MH+). |
| 122 | 2 HCl | $^1$H-NMR (DMSO): 7.5–7.4 (m, 5H), 7.3 (s, 2H), 4.47 (s, 2H), 4.4 (t, 1H), 4.1–3.85 (m, 2H), 3.75 (s, 3H), 3.35–3.2 (m, 6H), 3.1 (m, 2H). Mass: (LC/MS APCI+): 395/397/399 (MH+). |
| 130 | | $^1$H-NMR (CDCl3): 7.78 (s, 1H), 7.68 (s, 2H), 7.29 (m, 5H), 4.60 (s, 2H), 4.1–3.9 (m, 2H), 3.85 (m, 1H), 3.30 (m, 2H), 3.12 (m, 2H), 3.03 (m, 2H), 2.87 (m, 4H), 2.05 (m, 2H). Mass: (LC/MS APCI+): 447 (MH+). |
| 131 | 2 HCl.½ H$_2$O | $^1$H-NMR (DMSO): 7.75 (s, 1H), 7.65 (s, 2H), 7.2–7.1 (m, 5H), 4.2 (t, 1H), 4.1–3.8 (dd, 2H), 3.3 (m, 2H), 3.2 (m, 4H), 3.1 (m, 4H). Mass: (LC/MS ESI+): 449 (MH+). |
| 132 | 2 HCl.½ H$_2$O | $^1$H-NMR (DMSO): 7.35 (m, 5H), 6.82 (s, 1H), 6.74 (s, 2H), 4.15 (t, 1H), 3.54 (s, 2H), 3.45–3.0 (m, 10H), 2.16 (s, 6H). Mass: (LC/MS ESI+): 341 (MH+). |

1.3.2. Preparation of compounds of formula II wherein Ar$^1$ is a mono-, di- or tri-substituted phenyl group in which the substituent is NO$_2$.

1-[2-(3,5-Bis-trifluoromethyl-benzyloxy)-1-(2-nitrophenyl)-ethyl]-piperazine (compound 133) was obtained by nitration of 1-[2-(3,5-Bis-trifluoromethyl-benzyloxy)-1-phenyl-ethyl]-piperazine (compound 86 prepared at example 1.3.1 above) according to the method described in Lynch B. M., Poon L., Can. J. Chem. (1967), 45, 1431.

1.4. Preparation of Compounds of Formula I 1.4.1. Preparation of compounds of formula I according to process (a.1).

In a round-bottomed flask fitted with a reflux condenser and a thermometer 7.5 g (17 mmoles) of 1-[2-(3,5-Bis-trifluoromethyl-benzyloxy)-1-phenyl-ethyl]-piperazine (compound 86 prepared at example 1.3.1 above), 60 ml of DMF and 7.2 g (52 mmoles) of potassium carbonate were introduced. The resulting mixture was cooled to 5° C., and a solution of 5 g (31 mmoles) of 5-bromo-valeronitrile in 10 ml of DMF was added dropwise. The reaction mixture was stirred at 5° C. for 5 hours, and volatile substances were removed under reduced pressure. Methylene chloride (50 ml) was added, the organic phase was washed twice with water, dried over magnesium sulfate, and concentrated under reduced pressure, affording 11.3 g of an oil. This oil was purified by chromatography on silica gel (eluent: methylene chloride-methanol-aqueous ammonia 98.5/1.5/0.15 (v/v/v)), affording 7.2 g of {4-[2-(3,5-Bis-trifluoromethyl-benzyloxy)-1-phenyl-ethyl]-piperazin-1-yl}-acetic acid methyl ester (compound 134) as an oil. Yield: 80%.

The compounds listed in Table VI were obtained by this method.

Physico-chemical properties of the compounds of formula I prepared according to this method are given in Table VIa below. When the compounds of formula I are in the form of non toxic pharmaceutically acceptable salts, they are obtained by the general methods given above.

The following racemic mixtures were resolved into their individual enantiomers by chromatography using a chiral stationary phase:

compound 175: stationary phase: CHIRALPAK AD, detection at 226 nm; temperature 30° C.; eluent: ethanol 10%, benzine 90%, diethylamine 0.1%; the individual isomers so-obtained will be referred to as compounds 176 (NSA) and 177 (NSB), 176 being the compound that elutes the fastest;

compound 181: stationary phase: CHIRALCEL OJ, detection at 226 nm; temperature 30° C.; eluent: isopropanol 5%, benzine 95%, diethylamine 0.1%; the individual isomers so-obtained will be referred to as compounds 182 (NSA) and 183 (NSB), 182 being the compound that elutes the fastest;

compound 214: stationary phase: CHIRALPAK AS, detection at 226 nm; temperature 30° C.; eluent: ethanol 10%, benzine 90%, diethylamine 0.1%; the individual isomers so-obtained will be referred to as compounds 215 (S,R) and 218 (R,S), 215 being the compound that elutes the slowest;

compound 224: stationary phase: CHIRALCEL OJ, detection at 226 nm; temperature: room temperature; eluent: ethanol 5%, benzine 95%, diethylamine 0.1%; the individual isomers so-obtained will be referred to as compounds 225 (NSA) and 226 (NSB), 225 being the compound that elutes the fastest.

TABLE VI

Compound of formula I by process (a.1)

| Cpd No. | Stereo-chemistry | n' | R2 | $Ar^1$ | $Ar^2$ | Z | W | Starting cpd No. |
|---|---|---|---|---|---|---|---|---|
| 134 | racemic | 1 | H | phenyl | 3,5-bis(trifluoromethyl)phenyl | O | MeO(CO)CH$_2$— | 86 |
| 135 | racemic | 1 | H | phenyl | 3,5-bis(trifluoromethyl)phenyl | O | EtO(CO)CH$_2$— | 86 |
| 136 | S | 1 | H | phenyl | 3,5-bis(trifluoromethyl)phenyl | O | iPrO(CO)CH$_2$— | 87 |
| 137 | S | 1 | H | phenyl | 3,5-bis(trifluoromethyl)phenyl | O | tBuO(CO)CH$_2$— | 87 |
| 138 | racemic | 1 | H | phenyl | 3,5-bis(trifluoromethyl)phenyl | O | EtO(CO)(CH$_2$)$_3$— | 86 |
| 139 | racemic | 1 | H | phenyl | 3,5-bis(trifluoromethyl)phenyl | O | MeO(CO)(CH$_2$)$_4$— | 86 |
| 140 | racemic | 1 | H | phenyl | 3,5-bis(trifluoromethyl)phenyl | O | EtO(CO)(CH$_2$)$_4$— | 86 |
| 141 | racemic | 1 | H | phenyl | 3,5-bis(trifluoromethyl)phenyl | O | EtO(CO)(CH$_2$)$_5$— | 86 |
| 142 | racemic | 1 | H | phenyl | 3,5-bis(trifluoromethyl)phenyl | O | $^i$PrO(CO)(CH$_2$)$_5$— | 86 |
| 143 | racemic | 1 | H | phenyl | 3,5-bis(trifluoromethyl)phenyl | O | H$_2$N(CO)CH$_2$— | 86 |
| 144 | S | 1 | H | phenyl | 3,5-bis(trifluoromethyl)phenyl | O | H$_2$N(CO)CH$_2$— | 87 |
| 145 | R | 1 | H | phenyl | 3,5-bis(trifluoromethyl)phenyl | O | H$_2$N(CO)CH$_2$— | 88 |
| 146 | racemic | 1 | H | phenyl | 3,5-bis(trifluoromethyl)phenyl | O | H$_2$N(CO)(CH$_2$)$_2$— | 87 |
| 147 | racemic | 1 | H | phenyl | 3,5-bis(trifluoromethyl)phenyl | O | H$_2$N(CO)CH$_2$O(CH$_2$)$_2$— | 86 |
| 148 | S | 1 | H | phenyl | 3,5-bis(trifluoromethyl)phenyl | O | H$_2$N(CO)CH$_2$O(CH$_2$)$_2$— | 87 |
| 149 | R | 1 | H | phenyl | 3,5-bis(trifluoromethyl)phenyl | O | H$_2$N(CO)CH$_2$O(CH$_2$)$_2$— | 88 |
| 150 | racemic | 1 | H | phenyl | 3,5-bis(trifluoromethyl)phenyl | O | H$_2$N(CO)(CH$_2$)$_5$— | 86 |
| 151 | racemic | 1 | H | phenyl | 3,5-bis(trifluoromethyl)phenyl | O | NC(CH$_2$)$_3$— | 86 |
| 152 | racemic | 1 | H | phenyl | 3,5-bis(trifluoromethyl)phenyl | O | NC(CH$_2$)$_4$— | 86 |
| 153 | S | 1 | H | phenyl | 3,5-bis(trifluoromethyl)phenyl | O | NC(CH$_2$)$_4$— | 87 |
| 154 | R | 1 | H | phenyl | 3,5-bis(trifluoromethyl)phenyl | O | NC(CH$_2$)$_4$— | 88 |
| 155 | racemic | 1 | H | phenyl | 3,5-bis(trifluoromethyl)phenyl | O | NC—CH$_2$O(CH$_2$)$_2$— | 86 |
| 156 | racemic | 1 | H | phenyl | 3,5-bis(trifluoromethyl)phenyl | O | NC(CH$_2$)$_5$— | 86 |
| 157 | racemic | 1 | H | phenyl | 3,5-bis(trifluoromethyl)phenyl | O | HO(CH$_2$)$_2$— | 86 |
| 158 | S | 1 | H | phenyl | 3,5-bis(trifluoromethyl)phenyl | O | HO(CH$_2$)$_2$O(CH$_2$)$_2$— | 87 |
| 159 | racemic | 1 | H | phenyl | 3,5-bis(trifluoromethyl)phenyl | O | HO$_3$S(CH$_2$)$_2$— | 86 |
| 160 | racemic | 1 | H | phenyl | 3,5-bis(trifluoromethyl)phenyl | O | HO$_3$S(CH$_2$)$_3$— | 86 |
| 161 | racemic | 1 | H | phenyl | 3,5-bis(trifluoromethyl)phenyl | O | 2-(4-thiomorpholino 1,1-dioxide)ethyl | 86 |
| 162 | racemic | 1 | H | phenyl | 3,5-bis(trifluoromethyl)phenyl | O | 2-(N-morpholino)ethyl | 86 |
| 163 | racemic | 1 | H | phenyl | 3,5-bis(trifluoromethyl)phenyl | O | (EtO)$_2$(PO)(CH$_2$)$_2$— | 86 |
| 164 | S | 1 | H | phenyl | 3,5-bis(trifluoromethyl)phenyl | O | (EtO)$_2$(PO)(CH$_2$)$_2$— | 87 |
| 165 | racemic | 1 | H | phenyl | 3,5-bis(trifluoromethyl)phenyl | O | 2-(EtO(CO))—C$_6$H$_4$—CH$_2$— | 86 |
| 166 | racemic | 1 | H | phenyl | 3,5-bis(trifluoromethyl)phenyl | O | 3-(MeO(CO))—C$_6$H$_4$—CH$_2$— | 86 |
| 167 | S | 1 | H | phenyl | 3,5-bis(trifluoromethyl)phenyl | O | 4-(MeO(CO))—C$_6$H$_4$—CH$_2$— | 87 |
| 168 | S, NS | 1 | H | phenyl | 3,5-bis(trifluoromethyl)phenyl | O | C$_6$H$_5$CH(COOMe)— | 87 |
| 169 | racemic | 1 | H | phenyl | 3,5-bis(trifluoromethyl)phenyl | O | C$_6$H$_5$CH(OH)(CH$_2$)$_2$— | 86 |
| 170 | racemic | 1 | H | phenyl | 3,5-bis(trifluoromethyl)phenyl | O | 2-pyridinyl-CH$_2$— | 86 |
| 171 | racemic | 1 | H | phenyl | 3,5-bis(trifluoromethyl)phenyl | O | N-phthalimidyl-(CH$_2$)$_2$— | 86 |
| 172 | racemic | 1 | H | phenyl | 3,5-bis(trifluoromethyl)phenyl | O | 3,4,5-trimethoxyphenyl-methyl | 86 |
| 173 | S | 1 | H | phenyl | 3,5-bis(trifluoromethyl)phenyl | O | 3,4,5-trimethoxyphenyl-methyl | 87 |
| 174 | R | 1 | H | phenyl | 3,5-bis(trifluoromethyl)phenyl | O | 3,4,5-trimethoxyphenyl-methyl | 88 |
| 175 | racemic | 1 | H | phenyl | 3,5-bis(trifluoromethyl)phenyl | O | 3,4,5-trimethoxyphenyl-methoxy-2-ethyl- | 86 |
| 178 | racemic | 1 | H | 4-methylphenyl | 3,5-bis(trifluoromethyl)phenyl | O | EtO(CO)CH$_2$— | 89 |
| 179 | racemic | 1 | H | 3-isopropylphenyl | 3,5-bis(trifluoromethyl)phenyl | O | EtO(CO)CH$_2$— | 90 |
| 180 | racemic | 1 | H | 4-methoxyphenyl | 3,5-bis(trifluoromethyl)phenyl | O | EtO(CO)CH$_2$— | 91 |
| 181 | racemic | 1 | H | 3-chlorophenyl | 3,5-bis(trifluoromethyl)phenyl | O | MeO(CO)CH$_2$— | 92 |
| 184 | racemic | 1 | H | 4-bromophenyl | 3,5-bis(trifluoromethyl)phenyl | O | MeO(CO)CH$_2$— | 93 |
| 185 | racemic | 1 | H | 4-fluorophenyl | 3,5-bis(trifluoromethyl)phenyl | O | NC(CH$_2$)$_4$— | 94 |
| 186 | NSA | 1 | H | 3,4-dichlorophenyl | 3,5-bis(trifluoromethyl)phenyl | O | EtO(CO)CH$_2$— | 96 |
| 187 | NSB | 1 | H | 3,4-dichlorophenyl | 3,5-bis(trifluoromethyl)phenyl | O | EtO(CO)CH$_2$— | 97 |
| 188 | racemic | 1 | H | 2,3-difluorophenyl | 3,5-bis(trifluoromethyl)phenyl | O | MeO(CO)CH$_2$— | 98 |
| 189 | racemic | 1 | H | 3,4,5-trifluorophenyl | 3,5-bis(trifluoromethyl)phenyl | O | EtO(CO)CH$_2$— | 99 |
| 190 | racemic | 1 | H | 2-nitrophenyl | 3,5-bis(trifluoromethyl)phenyl | O | MeO(CO)CH$_2$— | 134 |
| 191 | racemic | 1 | H | 1-naphthyl | 3,5-bis(trifluoromethyl)phenyl | O | H2N(CO)CH$_2$— | 100 |
| 192 | racemic | 1 | H | thiophen-2-yl | 3,5-bis(trifluoromethyl)phenyl | O | MeO(CO)CH$_2$— | 102 |
| 193 | racemic | 1 | H | thiophen-3-yl | 3,5-bis(trifluoromethyl)phenyl | O | MeO(CO)CH$_2$— | 103 |
| 194 | racemic | 1 | H | furan-2-yl | 3,5-bis(trifluoromethyl)phenyl | O | MeO(CO)CH$_2$— | 104 |
| 195 | racemic | 1 | H | benzo[c]thiophen-1-yl | 3,5-bis(trifluoromethyl)phenyl | O | MeO(CO)CH$_2$— | 105 |
| 196 | racemic | 1 | H | isobenzofuran-1-yl | 3,5-bis(trifluoromethyl)phenyl | O | MeO(CO)CH$_2$— | 106 |
| 197 | racemic | 1 | H | phenyl | 3,5-dimethylphenyl | O | MeO(CO)CH$_2$— | 108 |
| 198 | racemic | 1 | H | phenyl | 2-methoxyphenyl | O | MeO(CO)CH$_2$— | 110 |
| 199 | racemic | 1 | H | phenyl | 3-isopropoxyphenyl | O | MeO(CO)CH$_2$— | 111 |
| 200 | racemic | 1 | H | phenyl | 3,4,5-trimethoxyphenyl | O | H$_2$N(CO)CH$_2$— | 113 |
| 201 | racemic | 1 | H | phenyl | 3-chlorophenyl | O | EtO(CO)CH$_2$— | 114 |

TABLE VI-continued

Compound of formula I by process (a.1)

| Cpd No. | Stereo-chemistry | n' | R2 | Ar¹ | Ar² | Z | W | Starting cpd No. |
|---|---|---|---|---|---|---|---|---|
| 202 | racemic | 1 | H | phenyl | 3,5-dichlorophenyl | O | MeO(CO)CH$_2$— | 115 |
| 203 | S | 1 | H | phenyl | 3,5-dichlorophenyl | O | EtO(CO)CH$_2$— | 116 |
| 204 | R | 1 | H | phenyl | 3,5-dichlorophenyl | O | EtO(CO)CH$_2$— | 117 |
| 205 | racemic | 1 | H | phenyl | 3,4-dichlorophenyl | O | MeO(CO)CH$_2$— | 118 |
| 206 | racemic | 1 | H | phenyl | 3,5-dibromophenyl | O | EtO(CO)CH$_2$— | 119 |
| 207 | racemic | 1 | H | phenyl | 3,5-difluorophenyl | O | EtO(CO)CH$_2$— | 120 |
| 208 | racemic | 1 | H | phenyl | 3-bromo-5-iodophenyl | O | MeO(CO)CH$_2$— | 121 |
| 209 | racemic | 1 | H | 3,5-bis(trifluoromethyl)-phenyl | phenyl | O | EtO(CO)CH$_2$— | 123 |
| 210 | NSA | 1 | CH$_3$ | phenyl | 3,5-bis(trifluoromethyl)phenyl | O | MeO(CO)CH$_2$— | 124 |
| 211 | NSB | 1 | CH$_3$ | phenyl | 3,5-bis(trifluoromethyl)phenyl | O | MeO(CO)CH$_2$— | 125 |
| 212 | NSA | 1 | CH$_3$ | phenyl | 3,5-bis(trifluoromethyl)phenyl | O | NC(CH$_2$)$_4$— | 124 |
| 213 | NSB | 1 | CH$_3$ | phenyl | 3,5-bis(trifluoromethyl)phenyl | O | NC(CH$_2$)$_4$— | 125 |
| 214 | NSB | 1 | CH$_3$ | phenyl | 3,5-bis(trifluoromethyl)phenyl | O | H$_2$N(CO)CH$_2$— | 125 |
| 215 | S, R | 1 | CH$_3$ | phenyl | 3,5-bis(trifluoromethyl)phenyl | O | H$_2$N(CO)CH$_2$— | 126 |
| 216 | S, S | 1 | CH$_3$ | phenyl | 3,5-bis(trifluoromethyl)phenyl | O | H$_2$N(CO)CH$_2$— | 127 |
| 217 | R, R | 1 | CH$_3$ | phenyl | 3,5-bis(trifluoromethyl)phenyl | O | H$_2$N(CO)CH$_2$— | 128 |
| 218 | R, S | 1 | CH$_3$ | phenyl | 3,5-bis(trifluoromethyl)phenyl | O | H$_2$N(CO)CH$_2$— | 129 |
| 219 | S, R | 1 | CH$_3$ | phenyl | 3,5-bis(trifluoromethyl)phenyl | O | H$_2$N(CO)CH$_2$O(CH$_2$)$_2$— | 126 |
| 220 | S, S | 1 | CH$_3$ | phenyl | 3,5-bis(trifluoromethyl)phenyl | O | H$_2$N(CO)CH$_2$O(CH$_2$)$_2$— | 127 |
| 221 | R, R | 1 | CH$_3$ | phenyl | 3,5-bis(trifluoromethyl)phenyl | O | H$_2$N(CO)CH$_2$O(CH$_2$)$_2$— | 128 |
| 222 | R, S | 1 | CH$_3$ | phenyl | 3,5-bis(trifluoromethyl)phenyl | O | H$_2$N(CO)CH$_2$O(CH$_2$)$_2$— | 129 |
| 223 | racemic | 2 | H | phenyl | 3,5-bis(trifluoromethyl)phenyl | O | MeO(CO)CH$_2$— | 130 |
| 224 | racemic | 2 | H | phenyl | 3,5-bis(trifluoromethyl)phenyl | O | 3-(MeO(CO))—C$_6$H$_4$—CH$_2$— | 130 |
| 227 | racemic | 1 | H | phenyl | 3,5-bis(trifluoromethyl)phenyl | O | 4-quinolyl | 86 |
| 228 | racemic | 1 | H | phenyl | 3,5-bis(trifluoromethyl)phenyl | S | MeO(CO)CH$_2$O | 131 |

TABLE VIa

Physico-chemical properties of compounds of formula I.

| I | Stereo-chemistry | Salt | Characteristics |
|---|---|---|---|
| 134 | racemic | 2 HCl | $^1$H-NMR (DMSO): 7.92 (s, 1H), 7.84 (s, 2H), 7.5–7.3 (m, 5H), 4.69 (dd, 2H), 4.44 (t, 1H), 4.04 (m, 2H), 3.95 (dd, 2H), 3.66 (s, 2H), 6.64 (s, 3H), 3.3–3.15 (m, 2H), 3.1–3.0 (m, 6H). Mass: (LC/MS APCI+): 505 (MH+). |
| 137 | S | 2 HCl.½ H$_2$O | $^1$H-NMR (DMSO): 7.90 (s, 1H), 7.87 (s, 2H), 7.55–7.4 (m, 5H), 4.71 dd, 2H), 4.59 (t, 1H), 4.13 (dd, 1H), 4.02 (dd, 1H), 3.88 (s, 2H), 3.5–3.3 (m, 6H), 3.3–3.1 (m, 2H), 1.4 (s, 9H). Mass: (LC/MS APCI+): 547 (MH+). [α]D = +14.77° (1% CH3OH, 25° C.). |
| 138 | racemic | 2 maleate | $^1$H-NMR (DMSO): 7.9 (s, 1H), 7.75 (s, 2H), 7.25 (m, 5H), 6.17 (s, 4H), 4.6 (dd, 2H), 4.1–3.75 (m, 2H), 3.1 (m, 4H), 2.95 (m, 2H), 2.65 (m, 4H), 2.32 (t, 2H), 1.81 (m, 2H), 1.13 (t, 3H). Mass: (LC/MS APCI+): 547 (MH+). |
| 139 | racemic | 2 maleate | $^1$H-NMR (DMSO): 7.91 (s, 1H), 7.78 (s, 2H), 7.30 (m, 5H), 6.17 (s, 4H), 4.62 (s, 2H), 4.0–3.8 (m, 3H), 3.77 (s, 3H), 3.3–3.1 (m, 4H), 2.97 (t, 2H), 2.8–2.6 (m, 4H), 2.30 (t, 2H), 1.7–1.5 (m, 4H). Mass: (LC/MS APCI+): 547 (MH+). |
| 141 | racemic | 2 maleate | $^1$H-NMR (DMSO): 7.89 (s, 1H), 7.75 (s, 2H), 7.29 (m, 5H), 6.17 (s, 4H), 4.61 (s, 2H), 4.06 (q, 2H), 4.0–3.8 (m, 3H), 3.3–3.1 (m, 4H), 3.01 (t, 2H), 2.8–2.6 (m, 4H), 2.28 (t, 2H), 1.7–1.5 (m, 4H), 1.27 (m, 2H), 1.17 (t, 3H). Mass: (LC/MS APCI+): 575 (MH+). |
| 142 | racemic | 2 maleate | $^1$H-NMR (DMSO): 7.89 (s, 1H), 7.76 (s, 2H), 7.29 (m, 5H), 6.17 (s, 4H), 4.82 (m, 1H), 4.61 (s, 2H), 4.05–3.8 (m, 3H), 3.3–3.1 (m, 4H), 2.94 (t, 2H), 2.8–2.6 (m, 4H), 2.20 (t, 2H), 1.7–1.5 (m, 4H), 1.24 (m, 2H), 1.12 (d, 6H). Mass: (LC/MS APCI+): 589 (MH+). |
| 144 | S | 2 HCl | $^1$H-NMR (DMSO): 7.91 (s, 1H), 7.85 (s + s, 3H), 7.5–7.3 (m, 6H), 4.7 (s, 2H), 4.25 (t, 1H), 4.0–3.85 (m, 2H), 3.55 (s, 2H), 3.2–3.1 (m, 6H), 3.05– |

TABLE VIa-continued

Physico-chemical properties of compounds of formula I.

| I | Stereo-chemistry | Salt | Characteristics |
|---|---|---|---|
| 145 | R | 2 HCl | 2.9 (m, 2H).<br>Mass: (LC/MS APCI+): 490 (MH+).<br>$[\alpha]_D$ = +15.43° (1% CH$_3$OH, 25° C.).<br>$^1$H-NMR (DMSO): 7.91 (s, 1H), 7.85 (s + s, 3H), 7.5–7.3 (m, 6H), 4.7 (dd, 2H), 4.44 (t, 1H), 4.05 (dd, 1H), 3.95 (dd, 1H), 3.73 (s, 2H), 3.4–3.2 (m, 6H), 3.3–3.0 (m, 2H).<br>Mass: (EI/DIP): 489 (M+).<br>$[\alpha]_D$ = −17.7° (1% CH$_3$OH, 25° C.). |
| 147 | racemic | 2 HCl.½ H$_2$O | $^1$H-NMR (DMSO): 7.89 (s, 1H), 7.83 (s, 2H), 7.6 (s, 1H), 7.5–7.3 (m, 5H), 7.15 (s, 1H), 4.69 (dd, 2H), 4.44 (t, 1H), 4.15–3.95 (m, 2H), 3.91 (s, 2H), 3.74 (t, 2H), 3.6–3.4 (m, 4H), 3.4–3.2 (m, 4H), 3.2–3.1 (m, 2H).<br>Mass: (LC/MS ESI+): 534 (MH+). |
| 148 | S | 2 maleate ½ H$_2$O | $^1$H-NMR (DMSO): 7.88 (s, 1H), 7.74 (s, 2H), 7.3 (m, 5H), 6.18 (s, 4H), 4.60 (s, 2H), 4.0–3.7 (m, 7H), 3.88 (s, 2H), 3.69 (t, 2H), 3.2 (m, 6H), 2.7 (m, 2H).<br>Mass: (LC/MS APCI+): 534 (MH+).<br>$[\alpha]_D$ = +8.27° (1% CH$_3$OH, 25° C.). |
| 149 | R | 2 maleate.½ H$_2$O | $^1$H-NMR (DMSO): 7.88 (s, 1H), 7.75 (s, 2H), 7.3 (m, 5H), 6.18 (s, 4H), 4.61 (s, 2H), 4.0–3.7 (m, 7H), 3.88 (s, 2H), 3.68 (t, 2H), 3.2 (m, 6H), 2.7 (m, 2H).<br>Mass: (LC/MS APCI+): 534 (MH+).<br>$[\alpha]_D$ = −20° (1% CH$_3$OH, 25° C.). |
| 150 | racemic | 2 maleate | $^1$H-NMR (DMSO): 7.97 (s, 1H), 7.87 (s, 2H), 7.35 (m, 5H), 7.15 (s, 1H), 6.75 (s, 1H), 6.14 (s, 4H), 4.69 (s, 2H), 4.05–3.85 (m, 3H), 3.3–3.1 (m, 4H), 3.04 (t, 2H), 2.8–2.6 (m, 4H), 2.04 (t, 2H), 1.7–1.5 (m, 4H), 1.28 (m, 2H).<br>Mass: (LC/MS APCI): 546 (MH+). |
| 151 | racemic | 2 maleate | $^1$H-NMR (DMSO): 7.88 (s, 1H), 7.75 (s, 2H), 7.3 (m, 5H), 6.17 (s, 4H), 4.61 (m, 2H), 4.0–3.8 (m, 3H), 3.1 (m, 4H), 2.95 (m, 2H), 2.7 (m, 4H), 2.5 (m, 2H), 1.85 (m, 2H).<br>Mass: (LC/MS APCI+): 500 (MH+) |
| 152 | racemic | 2 maleate | $^1$H-NMR (DMSO): 7.89 (s, 1H), 7.76 (s, 2H), 7.32 (m, 5H), 6.18 (s, 4H), 4.61 (s, 2H), 4.1–3.8 (m, 5H), 3.3–3.2 (m, 4H), 3.01 (t, 2H), 2.8–2.6 (m, 4H), 2.45 (t, 2H), 1.8–1.5 (m, 4H).<br>Mass: (LC/MS APCI): 514 (MH+). |
| 155 | racemic | 2 maleate | $^1$H-NMR (DMSO): 7.91 (s, 1H), 7.78 (s, 2H), 7.32 (m, 5H), 6.17 (s, 4H), 4.62 (s, 2H), 4.40 (s, 2H), 4.1–3.8 (m, 5H), 3.19 (t, 2H), 3.2–3.1 (m, 4H), 2.96 (t, 2H), 2.8–2.6 (m, 4H).<br>Mass: (LC/MS APCI): 516 (MH+). |
| 156 | racemic | 2 maleate | $^1$H-NMR (DMSO): 7.88 (s, 1H), 7.75 (s, 2H), 7.32 (m, 5H), 6.18 (s, 4H), 4.60 (s, 2H), 4.1–3.8 (m, 3H), 3.3–3.1 (m, 4H), 2.96 (t, 2H), 2.8–2.6 (m, 4H), 2.40 (t, 2H), 1.7–1.5 (m, 4H), 1.27 (m, 2H).<br>Mass: (LC/MS APCI): 528 (MH+) |
| 157 | racemic | 2 HCl.½ H$_2$O | $^1$H-NMR (DMSO): 7.91 (s, 1H), 7.83 (s, 2H), 7.5–7.3 (m, 5H), 4.68 (dd, 2H), 4.36 (t, 1H), 4.1–3.9 (m, 2H), 3.7 (t, 1H), 3.5–3.3 (m, 4H), 3.3–3.0 (m, 6H).<br>Mass: (LC/MS APCI+): 477 (MH+). |
| 158 | S | 2 maleate | $^1$H-NMR (DMSO): 7.89 (s, 1H), 7.76 (s, 2H), 7.3 (m, 5H), 6.17 (s, 4H), 4.61 (dd, 2H), 4.0–3.75 (m, 3H), 3.65 (t, 2H), 3.48 (m, 2H), 3.45 (m, 2H), 3.18 (m, 6H), 2.7 (m, 2H).<br>Mass: (LC/MS APCI+):521 (MH+).<br>$[\alpha]_D$ = +9° (1% CH$_3$OH, 25° C.) |
| 159 | racemic | 1 H$_2$O | $^1$H-NMR (DMSO): 7.76 (s, 1H), 7.64 (s, 2H), 7.35–7.15 (m, 5H), 4.55 (s, 2H), 3.9–3.6 (m, 3H), 3.5 (t, 2H), 3.3 (t, 2H), 3.1–2.6 (m, 8H).<br>Mass: (LC/MS APCI+): 541 (MH+). |
| 160 | racemic | 2 HCl | $^1$H-NMR (DMSO): 7.90 (s, 1H), 7.83 (s, 2H), 7.45–7.35 (m, 5H), 4.68 (m, 2H), 4.40 (t, 1H), 4.2–3.8 (m, 2H), 3.5–3.3 (m, 4H), 3.3–3.0 (m, 6H), 2.67 (t, 2H), 1.97 (t, 2H).<br>Mass: (LC/MS APCI+): 555 (MH+). |

TABLE VIa-continued

Physico-chemical properties of compounds of formula I.

| I | Stereo-chemistry | Salt | Characteristics |
|---|---|---|---|
| 161 | racemic | 3 HCl | $^1$H-NMR (DMSO): 7.95 (s, 1H), 7.89 (s, 2H), 7.6–7.5 (m, 2H), 7.5–7.4 (m, 3H), 4.73 (s, 2H), 4.55 (t, 1H), 4.15 (dd, 1H), 4.05 (dd, 1H), 3.55–3.4 (m, 4H), 3.4–3.25 (m, 6H), 3.25–3.15 (m, 6H), 3.15–3.05 (m, 4H).<br>Mass: (LC/MS APCI+): 594 (MH+). |
| 162 | racemic | 3 HCl | $^1$H-NMR (DMSO): 7.92 (s, 1H), 7.85 (s, 2H), 7.5 (m, 2H), 7.4 (m, 3H), 4.7 (dd, 2H), 4.53 (t, 1H), 4.15–3.85 (m, 2H), 3.85 (t, 4H), 3.4–3.15 (m, 8H), 3.05 (m, 2H), 2.95–2.75 (m, 6H).<br>Mass: (LC/MS APCI+): 546 (MH+). |
| 164 | S | 2 maleate | $^1$H-NMR (DMSO): 7.98 (s, 1H), 7.88 (s, 2H), 7.36 (m, 5H), 6.14 (s, 4H), 4.69 (s, 2H), 4.1–3.8 (m, 3H), 4.03 (q, 4H), 3.4–3.1 (m, 8H), 2.8–2.6 (m, 2H), 2.20 (m, 2H), 1.24 (t, 3H).<br>Mass: (LC/MS APCI+): 597 (MH+).<br>$[\alpha]_D = +9.32°$ (1% CH$_3$OH, 25° C.). |
| 165 | racemic | 2 HCl | $^1$H-NMR (DMSO): 7.99 (d, 1H), 7.91 (s, 1H), 7.83 (s, 2H), 7.65–7.5 (m, 3H), 7.4–7.3 (m, 5H), 4.68 (s, 2H), 4.43 (s, 2H), 4.25 (q, 2H), 4.1–3.8 (m, 3H), 3.3–3.2 (m, 4H), 3.2–3.05 (m, 2H), 3.05–2.9 (m, 2H), 1.27 (t, 3H).<br>Mass: (LC/MS APCI+): 595 (MH+). |
| 168 | S, rac. | 2 HCl.1 H$_2$O | $^1$H-NMR (DMSO): 7.89 (s, 1H), 7.82 (s, 2H), 7.5–7.2 (m, 5H), 4.75–4.6 (dd, 2H), 4.66 (s, 1H), 4.6–4.4 (m, 1H), 4.2–3.9 (m, 2H) 3.58 (s, 3H), 3.3–3.15 (m, 2H), 3.1–2.95 (m, 2H), 2.77 (m, 4H).<br>Mass: (LC/MS APCI+): 581 (MH+).<br>$[\alpha]_D = +16.47°$ (1% CH$_3$OH, 25° C.). |
| 170 | racemic | 3 HCl.½ H$_2$O | $^1$H-NMR (DMSO): 8.68 (d, 1H), 8.2 (t, 1H), 7.95 (s, 1H), 7.9 (s, 2H), 7.76 (d, 1H), 7.7 (t, 1H), 7.6 (m, 2H), 7.45 (m, 3H), 4.73 (s, 2H), 4.67 (t, 1H), 4.26 (s, 2H), 4.2 (dd, 1H), 4.05 (dd, 1H), 3.5–3.4 (m, 2H), 3.2 (m, 6H).<br>Mass: (EI/DIP): 523 (M+). |
| 171 | racemic | — | $^1$H-NMR (DMSO): 7.9 (d, 1H), 7.75 (s, 1H), 7.64 (s, 2H), 7.5–7.1 (m, 8H), 4.57 (s, 2H), 4.3–4.1 (m, 2H), 4.0–3.7 (m, 6H), 3.65 (t, 1H), 3.14 (t, 2H), 2.7–2.5 (m, 2H), 2.5–2.3 (m, 2H).<br>Mass: (LC/MS APCI+): 606 (MH+). |
| 173 | S | 2 HCl | $^1$H-NMR (DMSO): 7.91 (s, 1H), 7.85 (s, 2H), 7.5–7.3 (m, 5H), 6.82 (s, 2H), 4.69 (s, 2H), 4.41 (t, 1H), 4.22 (s, 2H), 4.05 (dd, 1H), 3.95 (dd, 1H), 3.76 (s, 6H), 3.64 (s, 3H), 3.4–3.2 (m, 6H), 3.2–3.05 (m, 2H).<br>Mass: (EI/DIP): 612 (M+).<br>$[\alpha]_D = +19,63°$ (1% CH$_3$OH, 25° C.). |
| 174 | R | 2 HCl | $^1$H-NMR (DMSO): 7.92 (s, 1H), 7.85 (s, 2H), 7.5–7.3 (m, 5H), 6.81 (s, 2H), 4.68 (s, 2H), 4.33 (t, 1H), 4.19 (s, 2H), 4.05 (dd, 1H), 3.95 (dd, 1H), 3.76 (s, 6H), 3.64 (s, 3H), 3.4–3.15 (m, 6H), 3.1–2.95 (m, 2H).<br>Mass: (EI/DIP): 612 (M+).<br>$[\alpha]_D = -20,09°$ (1% CH$_3$OH, 25° C.). |
| 176 | NSA | 2 HCl | $^1$H-NMR (DMSO): 7.91 (s, 1H), 7.83 (s, 2H), 7.39 (m, 5H), 6.6 (s, 2H), 4.67 (s, 2H), 4.4 (s, 2H), 4.21 (t, 1H), 4.05–3.85 (m, 2H), 3.87 (s, 6H), 3.85 (m, 2H), 3.7 (s, 3H), 3.4–3.25 (m, 6H), 3.2–2.9 (m, 4H).<br>Mass: (EI/DIP): 656 (M+).<br>$[\alpha]_D = +12,61°$ (1% CH$_3$OH, 25° C.). |
| 177 | NSB | 2 HCl | $^1$H-NMR (DMSO): 7.9 (s, 1H), 7.81 (s, 2H), 7.38 (m, 5H), 6.6 (s, 2H), 4.66 (s, 2H), 4.39 (s, 2H), 4.21 (t, 1H), 4.05–3.85 (m, 2H), 3.92 (s, 6H), 3.9 (m, 2H), 3.69 (s, 3H), 3.4–3.25 (m, 6H), 3.2–2.9 (m, 4H).<br>Mass: (EI/DIP): 656 (M+).<br>$[\alpha]_D = -17,73°$ (1% CH$_3$OH, 25° C.). |
| 182 | NSA | 2 maleate | $^1$H-NMR (DMSO): 7.99 (s, 1H), 7.89 (s, 2H), 7.49 (s, 1H), 7.39 (m, 3H), 6.17 (s, 4H), 4.70 (s, 2H), 4.05 (m, 1H), 3.95 (m, 2H), 3.71 (s, 2H), 3.68 (s, 3H), 3.1–2.9 (m, 6H), 2.8 (m, 2H).<br>Mass: (LC/MS APCI): 539 (MH+). |

TABLE VIa-continued

Physico-chemical properties of compounds of formula I.

| I | Stereo-chemistry | Salt | Characteristics |
|---|---|---|---|
| 188 | racemic | 2 maleate | ¹H-NMR (DMSO): 8.00 (s, 1H), 7.85 (s, 2H), 7.4 (m, 1H), 7.26 (m, 2H), 6.18 (s, 4H), 4.69 (dd, 2H), 4.24 (t, 1H), 4.0–3.9 (m, 2H), 3.89 (s, 2H), 3.70 (s, 3H), 3.0 (m, 4H), 2.7 (m, 4H). Mass: (LC/MS APCI+): 541 (MH+). |
| 191 | racemic | 2 HCl | ¹H-NMR (DMSO): 8.21 (d, 1H), 7.85 (m, 2H), 7.81 (s, 1H), 7.75–7.65 (m, 3H), 7.5–7.4 (m, 3H), 4.98 (m, 1H), 4.62 (s, 2H), 4.1–3.9 (m, 2H), 3.67 (s, 2H), 3.3–3.15 (m, 6H), 3.15–2.95 (m, 2H). Mass: (LC/MS APCI+): 540 (MH+). |
| 192 | racemic | — | ¹H-NMR (DMSO): 7.98 (s, 1H), 7.95 (s, 2H), 7.41 (dd, 1H), 7.0–6.9 (m, 2H), 4.72 (s, 2H), 4.09 (t, 1H), 3.91 (dd, 1H), 3.82 (dd, 1H), 3.59 (s, 3H), 3.26 (s, 2H), 2.6–2.4 (m, 8H). Mass: (LC/MS APCI+): 511 (MH+). |
| 193 | racemic | — | ¹H-NMR (DMSO): 7.96 (s, 1H), 7.92 (s, 2H), 7.46 (m, 1H), 7.31 (d, 1H), 7.05 (dd, 1H), 4.69 (s, 2H), 4.0–3.75 (m, 3H), 3.59 (s, 3H), 3.25 (s, 2H), 2.6–2.35 (m, 8H). Mass: (LC/MS APCI+): 511 (MH+) |
| 194 | racemic | — | ¹H-NMR (DMSO): 7.97 (s, 1H), 7.93 (s, 2H), 7.57 (d, 1H), 6.41 (m, 1H), 6.29 (dd, 1H), 4.7 (dd, 2H), 4.0–3.8 (m, 3H), 3.58 (s, 3H), 3.26 (s, 2H), 2.5–2.3 (m, 8H). Mass: (LC/MS APCI+): 495 (MH+) |
| 200 | racemic | — | ¹H-NMR (DMSO): 7.35–7.2 (m, 5H), 7.0–6.85 (s + s, 2H), 6.5 (s, 2H), 4.38 (s, 2H), 3.99 (q, 1H), 3.8–3.3 (m, 2H), 3.71 (s, 6H), 3.64 (s, 3H), 2.7 (s, 2H), 2.5–2.4 (m, 8H). Mass: (LC/MS APCI+): 444 (MH+). |
| 208 | racemic | 2 maleate | ¹H-NMR (DMSO): 7.86 (s, 1H), 7.62 (s, 1H), 7.47 (s, 1H), 7.48 (m, 5H), 6.15 (s, 4H), 4.51 (s, 2H), 4.36 (m, 1H), 3.94 (m, 2H), 3.66 (s, 3H), 3.55 (s, 2H), 3.0–2.8 (m, 8H). Mass: (LC/MS APCI): 573/575 (MH+). |
| 219 | S, R | 2 maleate | ¹H-NMR (DMSO): 7.96 (s, 1H), 7.89 (s, 2H), 7.33 (m, 5H), 6.14 (s, 4H), 4.73 (q, 1H), 3.89 (s, 2H), 3.85–3.65 (m, 5H), 3.27 (t, 2H), 3.3–3.1 (m, 4H), 2.8–2.6 (m, 4H), 1.36 (m, 2H). Mass: (LC/MS APCI): 548 (MH+). $[\alpha]_D = +27$ (1% CH₃OH, 25° C.). |

1.4.2. Preparation of compounds of formula I according to process (a.2).

In a round-bottomed flask fitted with a reflux condenser and a thermometer 2.48 g (4 mmoles) of 5-{4-[2-(3,5-Bis-trifluoromethyl-benzyloxy)-1-phenyl-ethyl]-piperazin-1-yl}-pentanoic acid ethyl ester (compound 140 prepared at example 1.4.1 above), 45 ml of ethyl alcohol, 4 ml of water, and 6.6 ml of a 1N solution of sodium hydroxide in water were introduced. The mixture was stirred at room temperature for 22 hours, and 6.6 ml of a 1N solution of hydrochloric acid in water was added. The volatile substances were removed under reduced pressure, water and methylene chloride were added, the aqueous layer was extracted with methylene chloride, and the combined organic phases were dried over magnesium sulfate and concentrated under reduced pressure. The residue was dissolved in 35 ml of methylene chloride, 3.96 ml of a 1.96 N solution of hydrochloric acid in diethyl ether were added, and the volatile substances were removed under reduced pressure. The residue was recristallized from acetonitrile, affording 1.6 g of 5-{4-[2-(3,5-Bis-trifluoromethyl-benzyloxy)-1-phenyl-ethyl]-piperazin-1-yl}-pentanoic acid (compound 233) as a solid. Yield: 61%.

The compounds listed in Table VII were obtained by the same method. Physico-chemical properties of the compounds of formula I prepared according to this method are given in Table VIIa below. When the compounds of formula I are in the form of non toxic pharmaceutically acceptable salts, they are obtained by the general methods given above.

TABLE VII

Preparation of compounds of formula I by process (a.2)

| Cpd No. | W | Stereo-chemistry | Hydrolysis | Starting Cpd No |
|---|---|---|---|---|
| 229 | HOOC—CH₂— | racemic | KOH, room temp., 1 night | 134 or 135 |
| 230 | HOOC—CH₂— | S | KOH (3 eq), room temp., 4 h or HCl 1 N, 100° C., 11 h | 144 |

TABLE VII-continued

Preparation of compounds of formula I by process (a.2)

| Cpd No. | W | Stereo-chemistry | Hydrolysis | Starting Cpd No |
|---|---|---|---|---|
| 231 | HOOC—CH$_2$— | R | KOH (2.5 eq), room temp., 1 night, or NaOH, EtOH, H$_2$O | 145 |
| 232 | HOOC—(CH$_2$)$_3$— | racemic | KOH (3 eq), EtOH, reflux, 1 h | 138 |
| 233 | HOOC—(CH$_2$)$_4$— | racemic | NaOH, EtOH, H$_2$O | 140 |
| 234 | HOOC—(CH$_2$)$_5$— | racemic | NaOH, EtOH, H$_2$O | 141 or 150 |
| 235 | HOOC—CH$_2$O(CH$_2$)$_2$— | racemic | HCl 1 N, 50° C., 1 night | 147 |
| 236 | HOOC—CH$_2$O(CH$_2$)$_2$— | S | HCl 6 N, 50° C., 3 h 30 | 148 |
| 237 | HOOC—CH$_2$O(CH$_2$)$_2$— | R | HCl 6 N, 50° C. 1 night | 149 |
| 238 | HOOC—CH$_2$—NH—C(O)—CH$_2$— | S | KOH (2.5 eq), EtOH, 0–5° C., 2 h | 290 |
| 239 | (HO)$_2$(PO)(CH$_2$)$_2$— | racemic | HCl 6 N, 100° C., 4 days | 163 |
| 240 | (HO)(EtO)(PO)(CH$_2$)$_2$— | S | KOH (4 eq), EtOH, reflux, 24 h | 164 |
| 241 | 2-(HOOC)—C$_6$H$_4$—CH$_2$— | racemic | KOH (2.5 eq), MeOH, room temp., 48 h | 165 |
| 242 | 3-(HOOC)—C$_6$H$_4$—CH$_2$— | racemic | KOH (6 eq), MeOH, reflux, 4 days | 166 |
| 243 | 4-(HOOC)—C$_6$H$_4$—CH$_2$— | S | KOH (3 eq), MeOH, reflux, 1 night | 167 |
| 244 | C$_6$H$_5$CH(COOH)— | S, rac | HCl 6 N, CH$_3$COOH, 50° C., 7 days | 168 |
| 245 | HOOC—CH$_2$— | racemic | NaOH, EtOH, H$_2$O | 178 |
| 246 | HOOC—CH$_2$— | racemic | NaOH, EtOH, H$_2$O | 179 |
| 247 | HOOC—CH$_2$— | racemic | NaOH, EtOH, H$_2$O | 180 |
| 248 | HOOC—CH$_2$— | NSA | KOH (10 eq), EtOH, reflux, 1 h | 182 |
| 249 | HOOC—CH$_2$— | NSB | KOH (10 eq), EtOH, reflux, 6 h | 183 |
| 250 | HOOC—CH$_2$— | racemic | KOH, room temp., 48 h | 184 |
| 251 | HOOC—CH$_2$— | NSA | NaOH, EtOH, H$_2$O | 186 |
| 252 | HOOC—CH$_2$— | NSB | NaOH, EtOH, H$_2$O | 187 |
| 253 | HOOC—CH$_2$— | racemic | KOH (3 eq), MeOH, reflux, 1 h 30 | 188 |
| 254 | HOOC—CH$_2$— | racemic | NaOH, EtOH, H$_2$O | 189 |
| 255 | HOOC—CH$_2$— | racemic | KOH (2.5 eq), MeOH, room t°, 48 h | 190 |
| 256 | HOOC—CH$_2$— | racemic | KOH (2.5 eq), MeOH, room t°, 24 h | 192 |
| 257 | HOOC—CH$_2$— | racemic | KOH (2.5 eq), MeOH, room t°, 24 h | 193 |
| 258 | HOOC—CH$_2$— | racemic | KOH (2.5 eq), MeOH, room t°, 24 h | 194 |
| 259 | HOOC—CH$_2$— | racemic | KOH (2.5 eq), MeOH, room t°, 48 h | 195 |
| 260 | HOOC—CH$_2$— | racemic | KOH (2.5 eq), MeOH, room t°, 48 h | 196 |
| 261 | HOOC—CH$_2$— | racemic | KOH (2.5 eq), MeOH, reflux, 2 h | 197 |
| 262 | HOOC—CH$_2$— | racemic | KOH (2.5 eq), MeOH, reflux, 3 h | 198 |
| 263 | HOOC—CH$_2$— | racemic | KOH (2.5 eq), MeOH, room temp., 24 h | 199 |
| 264 | HOOC—CH$_2$— | racemic | NaOH, EtOH, H$_2$O | 201 |
| 265 | HOOC—CH$_2$— | racemic | HCl 3 N, 50° C., 55 h | 202 |
| 266 | HOOC—CH$_2$— | S | NaOH, EtOH, H$_2$O | 203 |
| 267 | HOOC—CH$_2$— | R | NaOH, EtOH, H$_2$O | 204 |
| 268 | HOOC—CH$_2$— | racemic | HCl 3 N, 50° C., 24 h | 205 |
| 269 | HOOC—CH$_2$— | racemic | NaOH, EtOH, H$_2$O | 206 |
| 270 | HOOC—CH$_2$— | racemic | NaOH, EtOH, H$_2$O | 207 |
| 271 | HOOC—CH$_2$— | racemic | KOH (3 eq), MeOH, reflux, 4 h | 208 |
| 272 | HOOC—CH$_2$— | racemic | NaOH, EtOH, H$_2$O | 209 |
| 273 | HOOC—CH$_2$— | NSA | KOH (3 eq), room temp., 4 h | 210 |
| 274 | HOOC—CH$_2$— | NSB | KOH (3 eq), room temp., 6 h | 211 |
| 275 | HOOC—CH$_2$— | S, R | HCl 10% | 215 |
| 276 | HOOC—CH$_2$— | S, S | HCl 10% | 216 |
| 277 | HOOC—CH$_2$— | R, R | HCl 10% | 217 |
| 278 | HOOC—CH$_2$— | R, S | HCl 10% | 218 |
| 279 | HOOC—CH$_2$O(CH$_2$)$_2$— | S, R | HCl 6 N, 50° C., 2 h | 219 |
| 280 | HOOC—CH$_2$O(CH$_2$)$_2$— | S, S | HCl 6 N, 50° C., 2 h | 220 |
| 281 | HOOC—CH$_2$O(CH$_2$)$_2$— | R, R | HCl 6 N, 50° C., 20 h | 221 |
| 282 | HOOC—CH$_2$O(CH$_2$)$_2$— | R, S | HCl 6 N, 50° C., 20 h | 222 |
| 283 | HOOC—CH$_2$— | racemic | KOH (2.5 eq), MeOH, reflux, 4 h | 223 |

TABLE VII-continued

Preparation of compounds of formula I by process (a.2)

| Cpd No. | W | Stereo-chemistry | Hydrolysis | Starting Cpd No |
|---|---|---|---|---|
| 284 | 3-(HOOC)—C$_6$H$_4$—CH$_2$— | NSA | KOH (2.5 eq), MeOH, reflux, 4 h | 225 |
| 285 | 3-(HOOC)—C$_6$H$_4$—CH$_2$— | NSB | KOH (3 eq), MeOH, reflux, 3 h | 226 |
| 286 | HOOC—CH$_2$— | racemic | HCl 6 N, 50° C., 48 h | 228 |

TABLE VIIa

Physico-chemical properties of compounds of formula I

| Cpd No. | Free base/Salt | Stereo-chemistry | Analysis |
|---|---|---|---|
| 229 | 2 HCl | racemic | $^1$H-NMR (DMSO): 7.97 (s, 1H), 7.94 (s, 2H), 7.62 (m, 2H), 7.4 (m, 2H), 4.74 (s, 2H), 4.6 (m, 1H), 4.35 (dd, 1H), 3.95 (dd, 1H), 3.95 (s, 2H), 3.5–3.3 (m, 6H), 3.3–3.1 (m, 2H). Mass: (LC/MS APCI+): 491 (MH+). |
| 230 | 2 HCl.½ H$_2$O | S | $^1$H-NMR (DMSO): 7.91 (s, 1H), 7.83 (s, 2H), 7.4 (m, 5H), 4.67 (s, 2H), 4.29 (t, 1H), 4.1–3.9 (m, 2H), 3.68 (s, 2H), 3.2–3.05 (m, 6H), 3.05–2.9 (m, 2H). Mass: (LC/MS APCI+): 491 (MH+). [α]$_D$ = +12,6 (1% CH$_3$OH, 25° C.). |
|  | 2 maleate |  | $^1$H-NMR (DMSO): 8.0 (s, 1H), 7.9 (s, 2H), 7.5–7.3 (m, 5H), 6.17 (s, 4H) 4.7 (s, 2H), 4.1–3.85 (m, 3H), 3.79 (s, 2H), 3.2–3.1 (m, 4H), 3.0–2.85 (m, 2H), 2.85–2.7 (m, 2H). Mass: (LC/MS APCI+): 491 (MH+). [α]$_D$ = +5.8 (1% CH$_3$OH, 25° C.). |
| 231 | 2 HCl.1 H$_2$O | R | $^1$H-NMR (DMSO): 7.98 (s, 1H), 7.93 (s, 2H), 7.6 (m, 2H), 7.4 (m, 3H), 4.74 (s, 2H), 4.6–4.4 (m, 1H), 4.25 (m, 1H), 3.95 (dd, 1H), 3.91 (s, 2H), 3.5–3.3 (m, 6H), 3.2–2.9 (m, 2H). Mass: (LC/MS APCI+): 491 (MH+). [α]$_D$ = −17.8 (1% CH$_3$OH, 25° C.). |
|  | 2 maleate |  | $^1$H-NMR (DMSO): 7.98 (s, 1H), 7.89 (s, 2H), 7.39 (m, 5H), 6.15 (s, 4H), 4.70 (s, 2H), 4.1–3.9 (m, 3H), 3.76 (s, 2H), 3.2 (m, 4H), 3.0–2.8 (m, 4H). Mass: (LC/MS APCI+): 491 (MH+). [α]$_D$ = −13.51 (1% CH$_3$OH, 25° C.). |
| 232 | 2 maleate | racemic | $^1$H-NMR (DMSO): 7.97 (s, 1H), 7.87 (s, 2H), 7.34 (m, 5H), 6.14 (s, 4H), 4.69 (s, 2H), 4.1–3.8 (m, 3H), 3.4–3.2 (m, 4H), 3.05 (t, 2H), 2.8–2.6 (m, 4H), 2.30 (t, 2H), 1.85 (m, 2H) Mass: (LC/MS APCI+): 519 (MH+). Mass: (LC/MS APCI−): 517 (M − H). |
| 233 | 2 HCl | racemic | $^1$H-NMR (DMSO): 7.98 (s, 1H), 7.96 (s, 2H), 7.65 (m, 2H), 7.45 (m, 3H), 4.74 (s, 2H), 4.65 (m, 1H), 4.3 (m, 1H), 4.0 (dd, 1H), 3.7–3.0 (m, 10H), 2.25 (t, 2H), 1.75–1.6 (m, 2H), 1.6–1.4 (m, 2H). Mass: (LC/MS APCI+): 533 (MH+). |
| 234 | ½ maleate | racemic | $^1$H-NMR (DMSO): 7.88 (s, 1H), 7.75 (s, 2H), 7.30 (m, 5H), 6.19 (s, 4H), 4.61 (s, 2H), 4.1–3.8 (m, 3H), 3.3–3.1 (m, 4H), 3.05 (t, 2H), 2.8–2.6 (m, 4H), 2.22 (t, 2H), 1.7–1.5 (m, 4H), 1.27 (m, 2H). Mass: (LC/MS APCI+): 547 (MH+). |
| 235 | 2 maleate | racemic | $^1$H-NMR (DMSO): 7.97 (s, 1H), 7.87 (s, 2H), 7.4–7.3 (m, 5H), 6.11 (s, 4H), 4.69 (s, 2H), 4.07 (s, 2H), 3.95–3.8 (m, 3H), 3.85 (t, 2H), 3.77 (t, 2H), 3.25 (m, 6H), 2.7 (m, 2H). Mass: (LC/MS APCI+): 535 (MH+). |
|  | 2 HCl |  | $^1$H-NMR (DMSO): 7.9 (s, 1H), 7.85 (s, 2H), 7.5–7.3 (m, 5H), 4.7 (dd, 2H), 4.4 (t, 1H), 4.05 (s, 2H), 4.1–3.9 (m, 2H), 3.75 (t, 2H), 3.6–3.4 (m, 4H), 3.4–3.2 (m, 4H), 3.2–3.0 (m, 2H) Mass: (LC/MS APCI+): 535 (MH+). |
| 236 | 2 HCl | S | $^1$H-NMR (DMSO): 7.90 (s, 1H), 7.82 (s, 2H), 7.5–7.3 (m, 5H), 4.68 (m, 2H), 4.36 (m, 1H), 4.2–3.9 (m, 4H), 3.75 (t, 2H), 3.5–3.0 (m, 10H). Mass: (LC/MS APCI+): 535 (MH+). |
|  | 2 maleate |  | $^1$H-NMR (DMSO): 7.89 (s, 1H), 7.76 (s, 2H), 7.30 (m, 5H), 6.18 (s, 4H), 4.61 (s, 2H), 4.05 (s, 2H), 4.1–3.8 (m, 3H), 3.78 (t, 2H), 3.4–3.2 (m, 6H), 2.9–2.7 (m, 4H) Mass: (LC/MS APCI+): 535 (MH+). [α]$_D$ = 9.87 (1% CH$_3$OH, 25° C.). |
| 237 | 2 HCl | R | $^1$H-NMR (DMSO): 7.90 (s, 1H), 7.79 (s, 2H), 7.3 (m, 5H), 4.64 (m, 2H), 4.2–3.9 (m, 5H), 3.73 (t, 2H), 3.4–2.8 (m, 10H). Mass: (LC/MS APCI+): 535 (MH+). |
|  | 2 maleate |  | $^1$H-NMR (DMSO): 7.97 (s, 1H), 7.87 (s, 2H), 7.35 (m, 5H), 6.14 (s, 4H), 4.69 (s, 2H), 4.07 (s, 2H), 4.0–3.8 (m, 5H), 3.4–3.2 (m, 4H), 2.9–2.7 (m, 4H). Mass: (LC/MS APCI+): 535 (MH+). [α]$_D$ = −12.82 (1% CH$_3$OH, 25° C.). |
| 238 | — | S | $^1$H-NMR (DMSO): 7.86 (s, 1H), 7.75 (s, 2H), 7.35–7.15 (m, 5H), 4.6 (s, 2H), 3.8 (m, 2H), 3.65 (t, 1H), 3.57 (s, 2H), 2.95 (s, 2H), 2.55–2.45 (m, 8H). Mass: (LC/MS APCI+): 548 (MH+). [α]$_D$ = +17.2 (1% CH$_3$OH, 25° C.). |
| 239 | 2 HCl | racemic | $^1$H-NMR (DMSO): 7.92 (s, 1H), 7.84 (s, 2H), 7.40 (m, 5H), 4.68 (s, 2H), 4.32 (t, 1H), 4.1–3.8 (m, 2H), 3.4 (m, 4H), 3.25 (m, 4H), 3.1 (m, 2H), 2.1–1.9 (m, 2H). Mass: (LC/MS APCI+): 540 (MH+). |

TABLE VIIa-continued

Physico-chemical properties of compounds of formula I

| Cpd No. | Free base/Salt | Stereo- chemistry | Analysis |
|---|---|---|---|
| 240 | 2 maleate.1 $H_2O$ | S | ¹H-NMR (DMSO): 7.97 (s, 1H), 7.86 (s, 2H), 7.34 (m, 5H), 6.12 (s, 4H), 4.68 (s, 2H), 4.1–3.8 (m, 5H), 3.3–3.1 (m, 6H), 2.9–2.6 (m, 4H), 2.1–1.9 (m, 2H), 1.19 (t, 3H). Mass: (LC/MS APCI+): 569 (MH+). |
| 241 | 2 HCl.1 $H_2O$ | racemic | ¹H-NMR (DMSO): 8.01 (d, 1H), 7.90 (s, 1H), 7.80 (s, 2H), 7.65–7.5 (m, 3H), 7.4–7.3 (m, 5H), 4.66 (s, 2H), 4.46 (s, 2H), 4.27 (t, 1H), 4.15–3.9 (m, 2H), 3.35 (m, 4H), 3.2–3.05 (m, 2H), 3.05–2.9 (m, 2H). Mass: (LC/MS APCI+): 567 (MH+). |
| 242 | 2 HCl.½ $H_2O$ | racemic | ¹H-NMR (CDCl3): 8.17 (s, 1H), 7.94 (d, 1H), 7.7–7.55 (m, 4H), 7.5–7.3 (m, 6H), 4.65 (dd, 2H), 4.3 (m, 1H), 4.15–3.85 (m, 4H), 3.5–3.1 (m, 8H). Mass: (LC/MS APCI+): 567 (MH+). |
| 243 | 2 maleate. ½ $H_2O$ | S | ¹H-NMR (DMSO): 7.98 (s, 1H), 7.95 (d, 2H), 7.88 (s, 2H), 7.59 (d, 2H), 7.38 (m, 5H), 6.17 (s, 2H), 4.69 (s, 2H), 4.2 (s, 2H), 4.05 (m, 2H), 3.9 (m, 1H), 3.2–3.0 (m, 8H). Mass: (LC/MS APCI+): 567 (MH+). $[\alpha]_D = 18$ (1% $CH_3OH$) |
| 244 | — | S, rac. | ¹H-NMR (DMSO): 7.87 (s, 1H), 7.75 (s, 2H), 7.4–7.15 (m, 10H), 4.59 (m, 2H), 4.22 (s, 1H), 3.8–3.6 (m, 3H), 3.05–2.9 (m, 4H), 2.8–2.5 (m, 4H). Mass: (LC/MS APCI+): 567 (MH+). $[\alpha]_D = +10.14$ (1% $CH_3OH$, 25° C.) |
| 245 | 1 $H_2O$ | racemic | ¹H-NMR (DMSO): 8.0 (s, 1H), 7.85 (s, 2H), 7.25–7.15 (m, 4H), 4.85 (dd, 2H), 3.95 (dd, 1H), 3.85 (dd, 1H), 3.60 (t, 1H), 3.1 (s, 2H), 2.7–2.4 (m, 8H), 2.3 (s, 3H). Mass: (LC/MS APCI+): 505 (MH+). |
| 246 | 2 maleate | racemic | ¹H-NMR (DMSO): 8.03 (s, 1H), 7.92 (s, 2H), 7.3–7.2 (m, 4H), 6.14 (s, 4H), 4.71 (s, 2H), 3.99 (m, 1H), 3.8 (m, 2H), 3.76 (s, 2H), 3.3–3.0 (m, 4H), 2.88 (m, 1H), 1.20 (d, 6H). Mass: (LC/MS APCI+): 533 (MH+). |
| 247 | 2 HCl.½ $H_2O$ | racemic | ¹H-NMR (DMSO): 7.92 (s, 1H), 7.85 (s, 2H), 7.42 (d, 2H), 6.96 (d, 2H), 4.7 (dd, 2H), 4.47 (t, 1H), 4.1–3.9 (m, 2H), 3.77 (s, 2H), 3.73 (s, 3H), 3.4–3.2 (m, 6H), 3.2–3.05 (m, 2H). Mass: (LC/MS APCI+): 521 (MH+) |
| 248 | 2 maleate | NSA | ¹H-NMR (DMSO): 7.98 (s, 1H), 7.87 (s, 2H), 7.45 (s, 1H), 7.35 (m, 3H), 6.15 (s, 4H), 4.69 (s, 2H), 3.91 (m, 3H), 3.85 (s, 2H), 3.2 (m, 4H), 2.9–2.7 (m, 4H). Mass: (LC/MS APCI): 525/527 (MH+). $[\alpha]_D = 8.2$ (1% $CH_3OH$). |
| 249 | 2 maleate | NSB | ¹H-NMR (DMSO): 7.99 (s, 1H), 7.87 (s, 2H), 7.46 (s, 1H), 7.37 (m, 3H), 6.14 (s, 4H), 4.69 (s, 2H), 3.89 (m, 3H), 3.84 (s, 2H), 3.2 (m, 4H), 2.9–2.7 (m, 4H). Mass: (LC/MS APCI+): 525/527 (MH+). |
| 250 | 2 HCl | racemic | ¹H-NMR (DMSO): 7.9 (s, 1H), 7.76 (s, 2H), 7.54 (d, 2H), 7.36 (d, 2H), 4.65 (dd, 2H), 4.16 (t, 1H), 4.05–3.85 (m, 2H), 3.82 (s, 2H), 3.3–3.15 (m, 4H), 3.15–3.0 (m, 2H), 3.0–2.8 (m, 2H). Mass: (LC/MS APCI+): 569/571 (MH+). |
| 251 | 1 $H_2O$ | NSA | ¹H-NMR (DMSO): 7.81 (s, 1H), 7.62 (s, 2H), 7.45 (m, 2H), 7.25 (d, 1H), 4.55 (s, 2H), 3.9–3.6 (m, 3H), 3.05 (s, 2H), 2.65–2.35 (m, 8H). Mass: (LC/MS APCI+): 559/561/563 (MH+). $[\alpha]_D = +6.65$ (1% $CH_3OH$, 25° C.). |
| 252 | 1 $H_2O$ | NSB | ¹H-NMR (DMSO): 7.85 (s, 1H), 7.65 (s, 2H), 7.45 (m, 2H), 7.27 (d, 1H), 4.58 (s, 2H), 3.83 (m, 2H), 3.65 (t, 1H), 3.06 (s, 2H), 2.6–2.35 (m, 8H). Mass: (LC/MS APCI+): 559/561/563 (MH+). $[\alpha]_D = -8.91$ (1% $CH_3OH$, 25° C.). |
| 253 | 2 maleate | racemic | ¹H-NMR (DMSO): 7.99 (s, 1H), 7.85 (s, 2H), 7.4 (m, 2H), 7.24 (m, 1H), 6.16 (s, 4H), 4.70 (dd, 2H), 4.22 (t, 1H), 4.0–3.9 (m, 2H), 3.98 (s, 2H), 3.22 (m, 4H), 2.75 (m, 4H). Mass: (LC/MS APCI+): 527 (MH+). |
| 254 | ½ $H_2O$ | racemic | ¹H-NMR (DMSO): 7.94 (s, 1H), 7.77 (s, 2H), 7.28 (dd, 2H), 4.64 (s, 2H), 3.81 (d, 2H), 3.65 (t, 1H), 3.08 (s, 2H), 2.6–2.35 (m, 8H). Mass: (LC/MS APCI+): 545 (MH+). |
| 255 | 2 HCl | racemic | ¹H-NMR (DMSO): 8.4 (s, 1H), 8.22 (dd, 2H), 7.98 (d, 1H), 7.98 (s, 1H), 7.85 (s, 2H), 7.7 (t, 1H), 4.71 (s, 2H), 4.4 (m, 1H), 4.1–3.9 (m, 2H), 4.04 (s, 2H), 3.5–2.9 (m, 8H). Mass: (LC/MS APCI+): 536 (MH+). |
| 256 | — | racemic | ¹H-NMR (DMSO): 7.91 (s, 1H), 7.86 (s, 2H), 7.38 (m, 1H), 6.98 (d, 1H), 4.65 (s, 2H), 4.11 (t, 1H), 3.9–3.75 (m, 2H), 3.25 (s, 2H), 3.1–2.9 (m, 4H), 2.7–2.55 (m, 4H). Mass: (LC/MS APCI): 497 (MH+). |
| 257 | — | racemic | ¹H-NMR (DMSO): 7.89 (s, 1H), 7.81 (s, 2H), 7.43 (m, 1H), 7.32 (d, 1H), 7.04 (dd, 1H), 4.63 (s, 2H), 4.0–3.75 (m, 3H), 3.33 (s, 2H), 3.2–3.0 (m, 4H), 2.7–2.55 (m, 4H). Mass: (LC/MS APCI+): 497 (MH+). |
| 258 | — | racemic | ¹H-NMR (DMSO): 7.97 (s, 1H), 7.93 (s, 2H), 7.58 (d, 1H), 6.42 (m, 1H), 6.32 (dd, 1H), 4.71 (dd, 2H), 4.0–3.8 (m, 3H), 3.2 (s, 2H), 2.7–2.55 (m, 4H), 2.55–2.4 (m, 4H). Mass: (LC/MS APCI+): 481 (MH+). |
| 259 | — | racemic | ¹H-NMR (DMSO): 7.87 (s, 3H), 7.85–7.75 (m, 1H), 7.72 (m, 1H), 6.65 (m, 3H), 4.68 (s, 2H), 4.2 (t, 1H), 3.9–3.75 (m, 2H), 3.4 (s, 2H), 3.2–3.0 (m, 4H), 2.85–2.7 (m, 4H). Mass: (LC/MS APCI+): 547 (MH+). |
| 260 | — | racemic | ¹H-NMR (DMSO): 7.94 (s, 3H), 7.58 (dd, 1H), 7.49 (d, 1H), 7.3–7.15 (m, 3H), 4.74 (dd, 2H), 4.12 (t, 1H), 3.99 (d, 2H), 3.07 (s, 2H), 2.75–2.5 (m, 8H). Mass: (LC/MS APCI+): 531 (MH+). |
| 261 | — | racemic | ¹H-NMR (DMSO): 7.35 (s, 5H), 6.86 (s, 1H), 6.77 (s, 2H), 4.38 (s, 2H), 3.9–3.7 (m, 3H), 3.45 (s, 2H), 3.1–2.7 (m, 8H), 2.15 (s, 6H). Mass: (LC/MS APCI+): 383 (MH+). |

TABLE VIIa-continued

Physico-chemical properties of compounds of formula I

| Cpd No. | Free base/Salt | Stereo-chemistry | Analysis |
|---|---|---|---|
| 262 | — | racemic | $^1$H-NMR (CDCl3): 7.3–7.1 (m, 7H), 6.9–6.7 (m, 2H), 4.5 (s, 2H), 3.8–3.6 (m, 3H), 3.78 (s, 3H), 3.36 (s, 2H), 3.25–3.0 (m, 4H), 2.9–2.6 (m, 4H). Mass: (LC/MS APCI+): 385 (MH+). |
| 263 | — | racemic | $^1$H-NMR (DMSO): 7.45–7.25 (m, 5H), 7.16 (t, 1H), 6.73 (d, 2H), 6.67 (s, 1H), 4.44 (m, 1H), 4.41 (s, 2H), 3.85–3.65 (m, 3H), 3.35 (s, 2H), 3.1 (m, 4H), 2.7–2.5 (m, 4H), 1.18 (d, 6H). Mass: (LC/MS APCI+): 413 (MH+). |
| 264 | 1 maleate. ⅓ H$_2$O | racemic | $^1$H-NMR (DMSO): 7.4–7.2 (m, 9H), 6.14 (s, 4H), 4.52 (s, 2H), 4.2 (m, 1H), 4.05 (m, 1H), 3.9 (m, 1H), 3.68 (s, 2H), 3.2–3.0 (m, 4H), 3.0–2.8 (m, 4H). Mass: (LC/MS APCI+): 389/391 (MH+). |
| 266 | — | S | $^1$H-NMR (DMSO): 7.45 (t, 1H), 7.4–7.2 (m, 5H), 7.22 (d, 2H), 4.47 (s, 2H), 3.85 (dd, 1H), 3.73 (t, 1H), 3.66 (dd, 2H), 3.16 (s, 2H), 2.7 (m, 4H), 2.6–2.4 (m, 4H). Mass: (LC/MS APCI+): 423/425/427 (MH+). [α]$_D$ = +8.9 (1% CH$_3$OH, 25° C.). |
| 267 | — | R | $^1$H-NMR (DMSO): 7.45 (t, 1H), 7.4–7.2 (m, 5H), 7.22 (d, 2H), 4.47 (s, 2H), 3.85 (dd, 1H), 3.73 (t, 1H), 3.66 (dd, 2H), 3.14 (s, 2H), 2.65 (m, 4H), 2.6–2.4 (m, 4H). Mass: (LC/MS APCI+): 423/425/427 (MH+). [α]$_D$ = +13.45 (1% CH$_3$OH, 25° C.). |
| 268 | 2 HCl | racemic | $^1$H-NMR (DMSO): 7.51 (d, 1H), 7.4 (m, 6H), 7.22 (d, 2H), 4.5 (s, 2H), 4.33 (t, 1H), 4.05–3.8 (m, 2H), 3.69 (s, 2H), 3.2–3.1 (m, 6H), 3.05 (m, 2H). Mass: (LC/MS APCI+): 423/425/427 (MH+). |
| 269 | 2 maleate | racemic | $^1$H-NMR (DMSO): 7.74 (s, 1H), 7.45 (s, 2H), 7.40 (m, 5H), 6.15 (s, 4H), 4.52 (s, 2H), 4.05 (m, 1H), 3.9–3.8 (m, 2H), 3.78 (s, 2H), 3.1 (m, 4H), 2.8 (m, 4H). Mass: (LC/MS APCI+): 511/513/515 (MH+). |
| 270 | 2 maleate | racemic | $^1$H-NMR (DMSO): 7.45 (d, 1H), 7.36 (s, 5H), 7.10 (m, 2H), 6.95 (d, 1H), 6.07 (s, 4H), 4.52 (s, 2H), 4.49 (s, 2H), 3.9 (m, 2H), 3.85 (m, 1H), 3.7–3.5 (m, 4H), 3.0–2.7 (m, 4H). Mass: (LC/MS APCI+): 391 (MH+). |
| 271 | 1 maleate.1 H$_2$O | racemic | $^1$H-NMR (DMSO): 7.84 (s, 1H), 7.61 (s, 1H), 7.44 (s, 1H), 7.4 (m, 5H), 6.22 (s, 4H), 4.48 (s, 2H), 4.1–3.7 (m, 5H), 3.2–3.0 (m, 6H, 2.9 (m, 2H). Mass: (LC/MS APCI+): 559/561 (MH+). |
| 272 | ⅔ H$_2$O | racemic | $^1$H-NMR (DMSO): 8.00 (s, 2H), 7.98 (s, 1H), 7.25 (m, 3H), 7.15 (m, 2H), 4.0–3.65 (m, 3H), 3.07 (s, 2H), 2.6–2.3 (m, 8H). Mass: (LC/MS APCI+): 491 (MH+). |
| 273 | 2 HCl.3 H$_2$O | NSA | $^1$H-NMR (DMSO): 7.87 (s, 1H), 7.81 (s, 2H), 7.5–7.3 (m, 5H), 4.7 (q, 1H), 4.35 (t, 1H), 3.95 (dd, 1H), 3.77 (s, 2H), 3.57 (dd, 1H), 3.4–3.1 (m, 6H), 3.1–3.0 (m, 2H), 1.41 (d, 3H). Mass:. (LC/MS APCI+): 505 (MH+). |
| 274 | 2 HCl.1 H$_2$O | NSB | $^1$H-NMR (DMSO): 7.89 (s, 1H), 7.8 (s, 2H), 7.4–7.3 (m, 5H), 4.71 (q, 1H), 4.35 (t, 1H), 4.1–3.9 (dd, 1H), 3.8 (s, 2H), 3.65 (dd, 1H), 3.4–3.1 (m, 6H), 3.1–2.95 (m, 2H), 1.35 (d, 3H). Mass: (LC/MS APCI+): 505 (MH+). |
| 275 | 2 HCl.½ H$_2$O | S, R | $^1$H-NMR (DMSO): 7.91 (s, 1H), 7.85 (s, 2H), 7.5–7.4 (m, 5H), 4.73 (q, 1H), 4.44 (t, 1H), 3.89 (s, 2H), 3.99 (m, 1H), 3.58 (m, 1H), 3.41 (m, 2H), 3.36 (m, 4H), 3.16 (m, 2H), 1.41 (d, 3H). Mass: (LC/MS APCI+): 505 (MH+). [α]$_D$ = +31,38; +23,65° (1% DMSO 25° C.). |
| 276 | 2 HCl.1 H$_2$O | S, S | $^1$H-NMR (DMSO): 7.93 (s, 1H), 7.82 (s, 2H), 7.4 (m, 5H), 4.70 (q, 1H), 4.35 (t, 1H), 4.00 (m, 1H), 3.78 (s, 2H), 3.66 (m, 1H), 3.23 (m, 4H), 3.20 (m, 2H), 3.04 (m, 2H), 1.35 (d, 3H). Mass: (LC/MS APCI+): 505 (MH+). [α]$_D$ = −14,33° (1% DMSO 25° C.). |
| 277 | 2 HCl.1 H$_2$O | R, R | $^1$H-NMR (DMSO): 7.92 (s, 1H), 7.82 (s, 2H), 7.4 (m, 5H), 4.71 (q, 1H), 4.34 (t, 1H), 4.00 (m, 1H), 3.79 (s, 2H), 3.66 (m, 1H), 3.23 (m, 4H), 3.20 (m, 2H), 3.04 (m, 2H), 1.36 (d, 3H). Mass: (LC/MS APCI+): 505 (MH+). [α]$_D$ = +13,41 (1% DMSO 25° C.). |
| 278 | 2 HCl.½ H$_2$O | R, S | $^1$H-NMR (DMSO): 7.91 (s, 1H), 7.84 (s, 2H), 7.5–7.4 (m, 5H), 4.72 (q, 1H), 4.44 (t, 1H), 3.89 (s, 2H), 3.99 (m, 1H), 3.58 (m, 1H), 3.41 (m, 2H), 3.36 (m, 4H), 3.16 (m, 2H), 1.40 (d, 3H). Mass: (LC/MS APCI+): 505 (MH+). [α]$_D$ = −31,66; −23,83° (1% DMSO 25° C.). |
| 279 | 2 HCl.1 H$_2$O | S, R | $^1$H-NMR (DMSO): 7.88 (s, 1H), 7.80 (s, 2H), 7.4–7.3 (m, 5H), 4.68 (q, 1H), 4.2–4.0 (m, 1H), 4.06 (s, 2H), 3.95–3.8 (m, 1H), 3.75 (t, 2H), 3.65–3.5 (m, 1H), 3.4–3.3 (m, 4H), 3.28 (t, 2H), 3.25–3.1 (m, 2H), 3.1–2.9 (m, 2H), 1.38 (d, 3H). Mass: (LC/MS APCI+): 549 (MH+). [α]$_D$ = +26,55° (1% CH$_3$OH, 25° C.). |
| 280 | 2 HCl.1 H$_2$O | S, S | $^1$H-NMR (DMSO): 7.89 (s, 1H), 7.79 (s, 2H), 7.5–7.3 (m, 5H), 4.69 (q, 1H), 4.26 (t, 1H), 4.1–3.95 (m, 1H), 4.05 (s, 2H), 3.75 (t, 2H), 3.7–3.6 (m, 1H), 3.5–3.3 (m, 4H), 3.29 (t, 2H), 3.3–3.15 (m, 2H), 3.15–3.0 (m, 2H), 1.34 (d, 3H). Mass: (LC/MS APCI+): 549 (MH+). [α]$_D$ = −3.51 (1% CH$_3$OH, 25° C.). |
| 281 | 2 HCl.½ H$_2$O | R, R | $^1$H-NMR (DMSO): 7.86 (s, 1H), 7.81 (s, 2H), 7.5–7.3 (m, 5H), 4.73 (q, 1H), 4.54 (t, 1H), 4.15–4.0 (m, 1H), 4.06 (s, 2H), 3.8–3.65 (m, 3H), 3.6–3.5 (m, 4H), 3.5–3.3 (m, 4H), 3.25–3.1 (m, 2H), 1.35 (d, 3H). Mass: (LC/MS APCI+): 549 (MH+). [α]$_D$ = +1.77° (1% CH$_3$OH, 25° C.). |
| 282 | 2 HCl.½ H$_2$O | R, S | $^1$H-NMR (DMSO): 7.89 (s, 1H), 7.80 (s, 2H), 7.4–7.3 (m, 5H), 4.68 (q, 1H), 4.1–4.0 (m, 1H), 4.06 (s, 2H), 3.95–3.8 (m, 1H), 3.74 (t, 2H), 3.6–3.5 (m, 1H), 3.4–3.3 (m, 4H), 3.26 (t, 2H), 3.15–3.0 (m, 2H), 3.0–2.85 (m, 2H), 1.37 (d, 3H). Mass: (LC/MS APCI+): 549 (MH+). [α]$_D$ = −30,67° (1% CH$_3$OH, 25° C.). |

TABLE VIIa-continued

Physico-chemical properties of compounds of formula I

| Cpd No. | Free base/Salt | Stereo-chemistry | Analysis |
|---|---|---|---|
| 283 | 2 HCl.½ H$_2$O | racemic | $^1$H-NMR (DMSO): 7.94 (s, 1H), 7.88 (s, 2H), 7.5–7.35 (m, 5H), 4.72 (s, 2H), 4.67 (m, 1H), 4.1–3.8 (m, 2H), 3.98 (s 2H), 3.7–3.5 (m, 4H), 3.4–3.2 (m, 4H), 2.15–2.0 (m, 2H). Mass: (LC/MS APCI+): 505 (MH+). |
| 284 | 2 maleate.1 H$_2$O | NSA | $^1$H-NMR (DMSO): 8.11 (s, 1H), 8.0 (m, 2H), 7.89 (s, 2H), 7.7 (d, 1H), 7.55 (t, 1H), 7.4–7.25 (m, 5H), 6.14 (s, 4H), 4.7 (s, 2H), 4.31 (s, 2H), 4.16 (t, 1H), 4.0–3.8 (m, 2H), 3.2–2.95 (m, 6H), 3.85 (m, 2H), 1.9 (m, 2H). Mass: (LC/MS APCI+): 581 (MH+). [α]$_D$ = −5.80 (1% CH$_3$OH, 25° C.). |
| 285 | 2 maleate.1 H$_2$O | NSB | $^1$H-NMR (DMSO): 8.11 (s, 1H), 8.0 (m, 2H), 7.89 (s, 2H), 7.7 (d, 1H), 7.55 (t, 1H), 7.4–7.25 (m, 5H), 6.15 (s, 4H), 4.7 (s, 2H), 4.31 (s, 2H), 4.16 (t, 1H), 4.0–3.8 (m, 2H), 3.2–2.95 (m, 6H), 3.85 (m, 2H), 1.92 (m, 2H). Mass: (LC/MS APCI+): 581 (MH+). [α]$_D$ = +2.30 (1% CH$_3$OH, 25° C.). |
| 286 | 2 HCl.2 H$_2$O | racemic | $^1$H-NMR (DMSO): 7.75 (s, 1H), 7.69 (s, 2H), 7.2 (m, 5H), 4.26 (t, 2H), 4.67 (m, 1H), 3.91 (dd, 2H), 3.84 (s 2H), 3.45–3.05 (m, 10H). Mass: (LC/MS APCI+): 507 (MH+). |

1.4.3. Preparation of compounds of formula I according to process (a.3).

1.4.3.1. (2-{4-[2-(3,5-Bis-trifluoromethyl-benzyloxy)-1-phenyl-ethyl]-piperazin-1-yl}ethoxy)-acetic acid isobutyl ester (compound 287) dichlorhydrate monohydrate.

In a round-bottomed flask fitted with a reflux condenser and a thermometer were introduced (2-{4-[2-(3,5-Bis-trifluoromethyl-benzyloxy)-1-phenyl-ethyl]-piperazin-1-yl}-ethoxy)-acetic acid (compound 235, 0.5 g, 0.84 mmoles) dissolved in THF (20 ml). To this solution cooled at 0° C. were successively added isobutanol (0.155 ml, 1.68 mmoles), DMAP (0.01 g, 0.084 mmoles) and EDCI (0.177 g, 0.93 mmoles). The reaction mixture was stirred for 2 hours at 0° C. and then allowed to reach room temperature and stirred overnight. The organic solution was washed with HCl 0.1N and water, dried over MgSO$_4$ and concentrated. The resulting oil was purified by chromatography on silica gel (eluent: CH$_2$Cl$_2$/MeOH/NH$_3$: 99.5/0.5/0.1 v/v/v) to yield (2-{4-[2-(3,5-Bis-trifluoromethyl-benzyloxy)-1-phenyl-ethyl]-piperazin-1-yl}-ethoxy)-acetic acid isobutyl ester (compound 287, 390 mg, 65%) which was converted into its dihydrochloride monohydrate salt by reaction with HCl in diethylether.

Analysis for dihydrochloride monohydrate salt of compound 287:

$^1$H-NMR (DMSO): 7.95 (s, 1H), 7.9 (s, 2H), 7.5–7.3 (m, 5H), 4.7 (dd, 2H), 4.4 (t, 1H), 4.1 (s, 2H), 4.05–3.85 (m, 2H), 3.8 (d, 2H), 3.85–3.7 (m, 2H), 3.55–3.05 (m, 10H), 1.7 (m, 1H), 0.8 (d, 6H).

Mass: (LC/MS APCI+): 591 (MH+).

1.4.3.2. 4-{4-[2-(3,5-Bis-trifluoromethyl-benzyloxy)-1-phenyl-ethyl]-piperazin-1-yl}-butyramide (compound 288).

In a round-bottomed flask fitted with a reflux condenser are introduced 493 mg (0.9 mmoles) of 4-{4-[2-(3,5-Bis-trifluoromethyl-benzyloxy)-1-phenyl-ethyl]-piperazin-1-yl}-butyric acid ethyl ester (compound 138 prepared at example 1.4.1 above), 15 ml of formamide and 97 mg (1.8 mmoles) of sodium methoxide. The mixture is heated to 95° C. for 4 hours, then 48 mg (0.9 mmole) of sodium methoxide are added and the mixture is kept overnight at 85° C. The mixture is cooled and partitioned between diethyl ether (100 ml) and brine (100 ml). The organic phase is dried and volatile substances are removed under reduced pressure, affording 400 mg of 4-{4-[2-(3,5-Bis-trifluoromethyl-benzyloxy)-1-phenyl-ethyl]-piperazin-1-yl}-butyramide as a yellow oil (yield 86%). The dimaleate salt of compound 288 is prepared in 2-butanone (yield: 4.32 g as a white solid).

Analysis for dimaleate of compound 288:

$^1$H-NMR (DMSO): 8.00 (s, 1H), 7.87 (s, 2H), 7.44 (s, 1H), 7.33 (m, 5H), 6.95 (s, 1H), 4.68 (dd, 2H), 3.9.1–3.8 (m, 3H), 3.9–3.4 (m, 8H), 3.0 (t, 2H), 2.14 (t, 2H), 1.78 (m, 2H).

Mass: (LC/MS APCI+): 518 (MH+).

1.4.3.3. (S)-{4-[2-(3,5-Bis-trifluoromethyl-benzyloxy)-1-phenyl-ethyl]-piperazin-1-yl}-acetonitrile dichlorhydrate (compound 291).

In a round-bottomed flask fitted with a reflux condenser and a thermometer were introduced 3 g (6.13 mmoles) of (S)-2-{4-[2-(3,5-Bis-trifluoromethyl-benzyloxy)-1-phenyl-ethyl]-piperazin-1-yl}-acetamide dissolved in 30 ml of CH$_2$Cl$_2$ (compound 144 prepared at example 1.4.1 above). The solution was cooled to −78° C. and DMSO (0.7 ml, 9.8 mmoles) and oxalyl chloride (0.6 ml, 7.4 mmoles) were added. After 15 minutes, triethylamine (2.5 ml, 18.4 mmoles) was added dropwise and the reaction mixture was stirred at −70° C. until complete disappearance of the starting material. The reaction was quenched with water and the pH was adjusted to 11 by addition of aqueous NaOH. The aqueous solution was extracted with CH$_2$Cl$_2$ and the combined organic layers were dried over MgSO$_4$ and concentrated. The crude was purified by chromatography on silica gel (eluent: CH$_2$Cl$_2$/MeOH/NH$_3$: 98/2/0.2 v/v/v) to yield (S)-{4-[2-(3,5-Bis-trifluoromethyl-benzyloxy)-1-phenyl-ethyl]-piperazin-1-yl}-acetonitrile (compound 291, 2.14 g, 73%) as a pale yellow powder which was converted into the dichlorhydrate salt by reaction with HCl in diethylether.

Analysis for Dihydrochloride of Compound 291

$^1$H-NMR (DMSO): 7.95 (s, 1H), 7.9 (s, 2H), 7.55–7.35 (m, 5H), 4.72 (dd, 2H), 4.6 (t, 1H), 4.07 (d, 2H), 3.72 (s, 2H), 3.15 (m, 4H), 2.75 (m, 4H).

Mass: (LC/MS APCI+): 472 (MH+).

[α]D=+11.2° (1% CH$_3$OH, 25° C.).

1.4.3.4. 2-{4-[2-(3,5-Bis-trifluoromethyl-benzyloxy)-1-phenyl-ethyl]-piperazin-1-yl}-N-methyl-acetamide (compound 292)

In a round-bottomed flask fitted with a reflux condenser and a thermometer are introduced 1.5 g (3 mmoles) of {4-[2-(3,5-Bis-trifluoromethyl-benzyloxy)-1-phenyl-ethyl]-piperazin-1-yl}-acetic acid (compound 229 prepared at example 1.4.2 above), 7 ml of THF and 7 ml of acetonitrile. Then 1.85 ml (3.7 mmoles) of a 2M solution of methylamine in THF are added, followed by 234 mg (1.5 mmoles) of HOBT, 1.33 ml (7.6 mmoles) of diisopropylethylamine and 880 mg (4.3 mmoles) of DCC. The mixture is stirred until completion of the reaction, and filtered. Volatile substances are removed under reduced pressure, and the residue is partitioned between ethyl acetate and 0.1 N sodium hydroxide. The organic phase is washed with brine, dried over magnesium sulfate and volatile substances are removed under reduced pressure. This yields crude 2-{4-[2-(3,5-Bis-trifluoromethyl-benzyloxy)-1-phenyl-ethyl]-piperazin-1-yl}-N-methyl-acetamide (compound 292) which is directly converted into its dimaleate salt in 2-butanone (1.44 g of a white solid; yield 65%).

The compounds 290, 293 and 294 (Table VIII) were obtained by the same method. Physico-chemical properties of the compounds of formula I prepared according to this method are given in Table VIIIa below. When the compounds of formula I are in the form of non toxic pharmaceutically acceptable salts, they are obtained by the general methods given above.

TABLE VIII

Preparation of compounds 290, 293 and 294.

| Cpd No. | W | Stereo-chemistry | Conditions material I | Starting |
|---|---|---|---|---|
| 290 | H$_3$COOC—CH$_2$—NH—CO—CH$_2$— | S | H$_2$N—CH$_2$—COOCH$_3$, EDCI, HOBT | 231 |
| 293 | (tBu)NH—CO—CH$_2$— | racemic | NH$_2$tBu, EDCI, HOBT | 229 |
| 294 | (tBu)(CH$_3$)NH—CO—CH$_2$— | racemic | NtBuCH$_3$, EDCI, HOBT | 229 |

TABLE VIIIa

Physico-chemical properties of compounds of formula I

| Cpd No. | Free base/ Salt | Stereo chemistry | Analysis |
|---|---|---|---|
| 292 | 2 maleate | racemic | $^1$H-NMR (DMSO): 8.2 (s, 2H), 8.0 (s, 1H), 7.5 (m, 2H), 6.3 (s, 4H), 4.8 (s, 2H), 4.0–3.8 (m, 3H), 3.6 (m, 2H), 3.2–2.8 (m, 8H), 2.7 (s, 3H). SM (LC/MS APCI+): 504 (MH+). |
| 293 | 2 maleate | racemic | $^1$H-NMR (DMSO): 7.9 (s, 1H), 7.8 (s, 2H), 7.3 (m, 5H), 6.2 (s, 4H), 4.7 (s, 2H), 3.9 (m, 3H), 3.5 (m, 2H), 2.6–3.2 (m, 8H), 1.2 (s, 9H). SM (LC/MS APCI+): 546 (MH+). |
| 294 | 2 maleate | racemic | $^1$H-NMR (DMSO): 7.97 (s, 1H), 7.87 (s, 2H), 7.35 (m, 5H), 6.13 (s, 4H), 4.68 (s, 2H), 4.12 (s, 2H), 4.0–3.8 (m, 3H), 3.3–3.0 (m, 6H), 2.79 (s, 3H), 2.75 (m, 2H), 1.37 (s, 9H). SM (LC/MS APCI+): 560 (MH+). |

1.4.4. Preparation of compounds of formula I according to process (a.4).

5-{4-[2-(3,5-Bis-trifluoromethyl-benzyloxy)-1-phenyl-ethyl]-piperazin-1-ylmethyl}-2,4-dihydro-[1,2,4]triazol-3-one (compound 295) is prepared by reacting 1-[2-(3,5-Bis-trifluoromethyl-benzyloxy)-1-phenyl-ethyl]-piperazine (compound 86 prepared at example 1.3.1 above) with N'-(2-Chloro-1-imino-ethyl)-hydrazinecarboxylic acid methyl ester according to the procedure described by Ladduwahetty T. et al., J. Med. Chem. (1996), 39, 2907–2914.

Analysis for compound 295:

$^1$H-NMR (DMSO): 7.95 (s, 1H), 7.85 (s, 2H), 7.35–7.25 (m, 5H), 4.65 (s, 2H), 3.9 (dd, 1H), 3.8 (dd, 1H), 3.65 (t, 1H), 3.21 (s, 2H), 2.5–2.35 (m, 8H).

Mass: (LC/MS APCI+): 530 (MH+).

1.4.5. Preparation of compounds of formula I according to process (a.5).

In a round-bottomed flask fitted with a reflux condenser and a thermometer 7.2 g (14 mmoles) of (S)-5-{4-[2-(3,5-Bis-trifluoromethyl-benzyloxy)-1-phenyl-ethyl]-piperazin-1-yl}-pentanenitrile (compound 153, prepared at example 1.4.1 above), 25 ml of toluene, 3.9 g (15 mmoles) of dibutyl tin oxide, and 3.3 g (28 mmoles) of trimethyl silyl azide were introduced. The mixture was heated at reflux for 18 hours, the volatile substances were removed under reduced pressure and the residue was washed with methyl alcohol, affording 11.4 g of crude product. The product was purified by chromatography on silica gel (eluant: methylene chloride-methanol-aqueous ammonia 90/10/1 (v/v/v)), affording 6.2 g of an oil (yield 80%). The product was dissolved in 50 ml of diisopropyl ether, the solution was filtered, and 13 ml of a 1.88N solution of hydrochloric acid in diethyl ether were added to the filtrate. The mixture was stirred for 16 hours and filtered. The precipitate was collected and recrystallized from acetonitrile, affording 4.2 g of (S)-1-[2-(3,5-Bis-trifluoromethyl-benzyloxy)-1-phenyl-ethyl]-4-[4-(1H-tetrazol-5-yl)-butyl]-piperazine (compound 298) as its dihydrochloride. Yield: 48%.

The compounds listed in Table IX were obtained by the same method. Physico-chemical properties of the compounds of formula I prepared according to this method are given in Table IXa below. When the compounds of formula I are in the form of non toxic pharmaceutically acceptable salts, they are obtained by the general methods given above.

TABLE IX

Preparation of compounds of formula by process (a.2)

| Cpd No. | Stereo-chemistry | n' | R2 | Ar$^1$ | Ar$^2$ | Z | W* | Starting cpd No |
|---|---|---|---|---|---|---|---|---|
| 296 | S | 1 | H | phenyl | 3,5-bis(trifluoromethyl)-phenyl | O | Tet-CH$_2$— | 291 |
| 297 | racemic | 1 | H | phenyl | 3,5-bis(trifluoromethyl)-phenyl | O | Tet-(CH$_2$)$_4$— | 152 |
| 299 | R | 1 | H | phenyl | 3,5-bis(trifluoromethyl)-phenyl | O | Tet-(CH$_2$)$_4$— | 154 |
| 300 | racemic | 1 | H | phenyl | 3,5-bis(trifluoromethyl)-phenyl | O | Tet-CH$_2$O(CH$_2$)$_2$— | 155 |
| 301 | racemic | 1 | H | 4-fluoro-phenyl | 3,5-bis(trifluoromethyl-phenyl | O | Tet-(CH$_2$)$_4$— | 185 |
| 302 | NSA | 1 | CH$_3$ | phenyl | 3,5-bis(trifluoromethyl)-phenyl | O | Tet-(CH$_2$)$_4$— | 212 |
| 303 | NSB | 1 | CH$_3$ | phenyl | 3,5-bis(trifluoromethyl)-phenyl | O | Tet-(CH$_2$)$_4$— | 213 |
| 304 | racemic | 1 | CH$_3$ | phenyl | 3,5-bis(trifluoromethyl)-phenyl | O | Tet-(CH$_2$)$_5$— | 156 |

*Tet means tetrazol.

TABLE IXa

Physico-chemical properties of compounds of formula I.

| Cpd No. | Stereo-chemistry | Salt | Characteristics |
|---|---|---|---|
| 296 | S | 2 HCl.1 H2O | $^1$H-NMR (DMSO): 7.92 (s, 1H), 7.85 (s, 2H), 7.55–7.35 (m, 5H), 4.7 (s, 2H), 4.55 (t, 1H), 4.1–3.9 (m, 4H), 3.3 (m, 2H), 3.1 (m, 2H), 2.8 (m, 4H). SM (LC/MS APCI+): 515 (MH+). [α]$_D$ = +19 (1% CH3OH, 25° C.). |
| 297 | racemic | 2 HCl | $^1$H-NMR (DMSO): 7.91 (s, 1H), 7.81 (s, 2H), 7.35 (m, 5H), 4.66 (s, 2H), 4.2 (m, 1H), 4.1–3.9 (m, 2H), 3.4–3.2 (m, 4H), 3.2–2.9 (m, 6H), 2.89 (t, 2H), 1.7–1.5 (m, 4H). SM (LC/MS APCI+): 557 (MH+) |
| 298 | S | 2 HCl | $^1$H-NMR (DMSO): 7.95 (s, 1H), 7.9 (s, 2H), 7.55 (m, 2H), 7.4 (m, 3H), 4.7 (s, 2H), 4.6 (t, 1H), 4.1–3.9 (m, 2H), 3.55–2.85 (m, 12H), 1.8–1.55 (m, 4H). SM (LC/MS APCI+): 557 (MH+). [α]$_D$ = +16 (1% CH$_3$OH, 25° C.). |
| 299 | R | 2 HCl | $^1$H-NMR (DMSO): 7.92 (s, 1H), 7.83 (s, 2H), 7.45–7.35 (m, 5H), 4.68 (s, 2H), 4.68 (t, 1H), 4.05–3.9 (m, 2H), 3.4–3.25 (m, 4H), 3.15–2.85 (m, 8H), 1.8–1.55 (m, 4H). SM (LC/MS APCI+): 557 (MH+). [α]$_D$ = +18.95 (1% CH$_3$OH, 25° C.). |
| 300 | racemic | 2 HCl | $^1$H-NMR (DMSO): 7.92 (s, 1H), 7.83 (s, 2H), 7.45–7.35 (m, 5H), 4.85 (s, 2H), 4.67 (s, 2H), 4.25 (t, 1H), 4.1–3.75 (m, 4H), 3.45–3.25 (m, 6H), 3.2–2.9 (m, 4H). SM (LC/MS APCI+): 559 (MH+). |
| 301 | racemic | 2 HCl. ⅓ C$_3$H$_8$O | $^1$H-NMR (DMSO): 7.98 (s, 1H), 7.9 (s, 2H), 7.6 (m, 2H), 7.25 (t, 2H), 4.72 (s, 2H), 4.45 (m, 1H), 4.15 (m, 1H), 3.95 (m, 1H), 3.75 (se, 1/3H), 3.6–3.0 (m, 10H), 2.92 (t, 2H), 1.8–1.6 (m, 4H), 1.04 (d, 2H). SM (LC/MS APCI+): 575 (MH+). |
| 302 | NSA | 2 HCl | $^1$H-NMR (DMSO): 7.9 (s, 1H), 7.8 (s, 2H), 7.45–7.25 (m, 5H), 4.7 (q, 1H), 4.3 (t, 1H), 4.05 (dd, 1H), 3.65 (dd, 1H), 3.5–2.95 (m, 10H), 2.9 (t, 2H), 1.7–1.55 (m, 4H), 1.35 (d, 3H). SM (LC/MS APCI+): 571 (MH+). |
| 303 | NSB | 2 HCl | $^1$H-NMR (DMSO): 7.91 (s, 1H), 7.81 (s, 2H), 7.45–7.25 (m, 5H), 4.7 (q, 1H), 4.28 (t, 1H), 4.05 (dd, 1H), 3.65 (dd, 1H), 3.5–2.95 (m, 10H), 2.9 (t, 2H), 1.7–1.55 (m, 4H), 1.35 (d, 3H). SM (LC/MS APCI+): 571 (MH+). |
| 304 | racemic | 2 maleate | $^1$H-NMR (DMSO): 7.97 (s, 1 H), 7.87 (s, 2H), 7.35 (m, 5H), 6.14 (s, 4H), 4.69 (s, 2H), 4.05–3.8 (m, 3H), 3.3–3.1 (m, 4H), 3.04 (t, 2H), 2.91 (t, 2H), 2.8–2.6 (m, 4H), 2.04 (t, 2H), 1.85–1.7 (m, 2H), 1.7–1.5 (m, 2H), 1.32 (m, 2H). SM (LC/MS APCI+): 571 (MH+). |

1.4.6. Preparation of compounds of formula I according to process (a.6).

1.4.6.1. Synthesis of N-[(2-{4-[2-(3,5-Bis-trifluoromethyl-benzyloxy)-1-phenyl-ethyl]-piperazin-1-yl}-ethoxy)-acetyl]-methanesulfonamide (compound 305).

In a round-bottomed flask fitted with a reflux condenser and a thermometer, 0.5 g (0.8 mmoles) of the dihydrochloride of (2-{4-[2-(3,5-Bis-trifluoromethyl-benzyloxy)-1-phenyl-ethyl]-piperazin-1-yl}-ethoxy)-acetic acid (compound 235) and 10 ml of dichloromethane, were introduced under nitrogen. The solution was cooled to 0° C. and 0.1 ml (1.2 mmoles) of oxalyl chloride were added. The reaction mixture was stirred at room temperature for one night. Again, 1 ml (12 mmoles) of oxalyl chloride were added. After 2 hours, the mixture was concentrated under reduced pressure. The residue was dissolved in dichloromethane and a solution of 0.075 g (0.8 mmoles) of methanesulfonamide and 0.12 ml (0.8 mmoles) of triethylamine in 5 ml of tetrahydrofuran, were added dropwise. The mixture was stirred at room temperature for one night. The solution was washed with water and brine. The organic phase was dried over magnesium sulfate and concentrated under reduced pressure affording 0.33 g of crude product. This was purified by chromatography on silica gel (eluent: $CH_2Cl_2/CH_3OH$: 95/5) affording 0.129 g of an oil. This oil was dissolved in methanol and was filtered on dicalite; 0.4 ml of HCl 1N and water were added. The mixture was concentrated under reduced pressure, lyophilized and dried under high vacuum at 50° C., affording 0.087 g (14%) of a white powder as the hydrated (3/2 $H_2O$) dihydrochloride of N-[(2-{4-[2-(3,5-Bis-trifluoromethyl-benzyloxy)-1-phenyl-ethyl]-piperazin-1-yl}-ethoxy)-acetyl]-methanesulfonamide (compound 305).

Analysis for hydrated (3/2 $H_2O$) dihydrochloride of compound 305:

$^1$H-NMR (DMSO): 7.92 (s, 1H), 7.81 (s, 2H), 7.35 (m, 5H), 4.66 (s, 2H), 4.08 (m, 3H), 4.0–3.9 (m, 2H), 3.75 (t, 2H), 3.4–3.2 (m, 6H), 3.2 (s, 3H), 3.1–2.8 (m, 4H).

Mass (LC/MS APCI+): 612 (MH+).

1.4.6.2. N-[(2-{4-[2-(3,5-Bis-trifluoromethyl-benzyloxy)-1-phenyl-ethyl]-piperazin-1-yl}-ethoxy)-acetyl]-benzenesulfonamide (compound 306).

In a round-bottomed flask fitted with a reflux condenser and a thermometer was introduced (2-{4-[2-(3,5-Bis-trifluoromethyl-benzyloxy)-1-phenyl-ethyl]-piperazin-1-yl}-ethoxy)-acetic acid (compound 235 prepared at example 1.4.2; 2.7 g, 4.54 mmoles) dissolved in $CH_2Cl_2$ (25 ml). Benzenesulphonamide (1.07 g, 6.8 mmoles), DMAP (10 mg, 0.45 mmoles) and EDCI (0.96 g, 5 mmoles) were added to the solution and the reaction mixture was stirred at room temperature for 48 hours. The organic solution was washed with HCl 0.1N and brine, dried over $MgSO_4$ and concentrated. The residue was purified by chromatography on silica gel (eluent: $CH_2Cl_2/MeOH/NH_3$: 95/5/0.2 v/v/v) to afford the monohydrate of N-[(2-{4-[2-(3,5-Bis-trifluoromethyl-benzyloxy)-1-phenyl-ethyl]-piperazin-1-yl}-ethoxy)-acetyl]-benzenesulfonamide (compound 306; 1.5 g, 50%) as a beige solid.

Analysis for the monohydrate of compound 306:

$^1$H-NMR (DMSO): 7.85 (s, 1H), 7.72 (s, 2H), 7.68 (dd, 2H), 7.4–7.25 (m, 8H), 4.64 (s, 2H), 4.05–3.75 (m, 2H), 3.76 (s, 2H), 3.7–3.6 (m, 3H), 3.2–3.0 (m, 6H), 2.8–2.55 (m, 4H).

Mass: (LC/MS APCI+): 674 (MH+).

1.4.7. Preparation of compounds of formula I according to process (a.7).

N-p-toluenesulfonic-carbamic acid 2-{4-[2-(3,5-bis-trifluoromethyl-benzyloxy)-1-phenyl-ethyl]-piperazin-1-yl}-ethyl ester (compound 307).

In a round-bottomed flask fitted with a reflux condenser and a thermometer was introduced compound 2-{4-[2-(3,5-Bis-trifluoromethyl-benzyloxy)-1-phenyl-ethyl]-piperazin-1-yl}-ethanol (compound 157 prepared at example 1.4.1; 0.5 g, 0.99 mmoles) dissolved in $CH_2Cl_2$ (5 ml). p-toluenesulfonylisocyanate (0.14 ml, 1.09 mmoles) was added to the solution and the reaction mixture was stirred at room temperature. The organic solution was washed with $NaHCO_3$ and the aqueous layer was extracted with $CH_2Cl_2$. The combined organic layers were dried over $MgSO_4$ and concentrated. The residue was purified by chromatography on silica gel (eluent: $CH_2Cl_2/MeOH/NH_3$: 95/5/0.2) to give N-p-toluenesulfonic-carbamic acid 2-{4-[2-(3,5-bis-trifluoromethyl-benzyloxy)-1-phenyl-ethyl]-piperazin-1-yl}-ethyl ester (compound 307; 400 mg, 60%) which was converted into its dihydrochloride salt by reaction with HCl in diethylether (Friesen R. W. and Phipps L. G., Synlett (1991), 420–422).

Analysis for the dihydrochloride of compound 307:

$^1$H-NMR (DMSO): 7.91 (s, 1H), 7.82 (s, 2H), 7.74 (d, 2H), 7.4 (m, 5H), 7.38 (d, 2H), 4.67 (s, 2H), 4.24 (m, 3H), 4–3.9 (m, 1H), 3.3–3.05 (m, 8H), 3.05–2.9 (m, 2H), 2.33 (s, 3H).

Mass: (LC/MS APCI+): 674 (MH+).

1.4.8. Preparation of compounds of formula I according to process (a.8).

N-(3-{4-[2-(3,5-Bis-trifluoromethyl-benzyloxy)-1-phenyl-ethyl]-piperazin-1-yl}-1-phenyl-propyl)-acetamide (compound 308).

In a round-bottomed flask fitted with a reflux condenser and a thermometer, 1.55 g (2.73 mmoles) of 3-{4-[2-(3,5-Bis-trifluoromethyl-benzyloxy)-1-phenyl-ethyl]-piperazin-1-yl}-1-phenyl-propan-1-ol (compound 169 prepared at example 1.4.1 above) and 3.6 ml of acetonitrile were introduced. The mixture was cooled to 0° C. and 3 ml of $H_2SO_4$ 12N were added dropwise. The reaction was stirred at room temperature for 4 hours. Cold water was added and a solution of NaOH 6N was added until pH 7. The mixture was filtered, and extracted with $CH_2Cl_2$. The organic phase was dried over magnesium sulfate, and concentrated under reduced pressure, affording 1.41 g of crude product. Purification by chromatography on silica gel (eluent: $CH_2Cl_2/CH_3OH/NH_4OH$, 97/3/03, (v/v/v)) gave 1.1 g of an oil which was dissolved in 10 ml of diisopropylether; 1.75 ml of a solution 1.88N of HCl in ether was added affording, after filtration, 0.82 g of the hydrated (5/4 $H_2O$) dihydrochloride of N-(3-{4-[2-(3,5-Bis-trifluoromethyl-benzyloxy)-1-phenyl-ethyl]-piperazin-1-yl}-1-phenyl-propyl)-acetamide (compound 308) as a white powder.

Analysis for the hydrated (5/4 $H_2O$) dihydrochloride of compound 308

$^1$H-NMR (DMSO): 8.43 (d, 1H), 7.93 (s, 1H), 7.5–7.3 (m, 5H), 7.3–7.15 (m, 5H), 4.83 (t, 1H), 4.7 (s, 2H), 4.4 (t, 1H), 4.1 (dd, 1H), 3.95 (dd, 1H), 3.5–3.0 (m, 10H), 2.05 (m, 2H), 1.86 (s, 3H).

Mass: (LC/MS APCI+): 608 (MH+).

1.4.9. Preparation of compounds of formula I according to process (a.9).

a. Following the procedure described in Maryanoff B. E. et al., J. Med Chem. (1981), 24 (1), 79–88: cis- and trans-4-{4-[2-(3,5-Bis-trifluoromethyl-benzyloxy)-1-phenyl-ethyl]-piperazin-1-yl}-cyclohexanecarboxylic acid ethyl ester (compounds 310 and 311).

In a round-bottomed flask fitted with a reflux condenser and a thermometer was introduced 1-[2-(3,5-Bis-trifluoromethyl-benzyloxy)-1-phenyl-ethyl]-piperazine (compound 86 prepared at example 1.3.1 above; 2.5 g, 5.8 mmol) dissolved in MeOH (30 ml). Acetic acid (0.43 ml, 7.52 mmoles), ethyl-4-oxocyclohexanecarboxylate (3.7 ml, 23 mmoles) and NaBH$_3$CN (0.55 g, 8.7 mmoles) were added to the solution and the reaction mixture was heated at 50° C. MeOH was evaporated in vacuo and the residue was taken up in water. The aqueous layer was extracted with CH$_2$Cl$_2$ and the combined organic layers were dried over MgSO$_4$ and concentrated. The crude was purified by chromatography on silica gel (eluent:Hex/AcOEt: 30/70 v/v) to give cis- and trans-4-{4-[2-(3,5-Bis-trifluoromethyl-benzyloxy)-1-phenyl-ethyl]-piperazin-1-yl}-cyclohexanecarboxylic acid ethyl ester (compound 309; 3 g, 88%), which was separated by chiral HPLC (Chiralpak AD, eluent: MeOH/EtOH/Benzine/DEA: 8/2/90/0.1 v/v/v/v) into its cis and trans isomers (compounds 310 and 311). It was impossible by NMR to determine which of these two compounds has the cis-conformation and which has the trans-configuration.

b. Cis- and trans-4-{4-[2-(3,5-Bis-trifluoromethyl-benzyloxy)-1-phenyl-ethyl]-piperazin-1-yl}-cyclohexanecarboxylic acid dichlorhydrate (compounds 312 and 313).

In a round-bottomed flask fitted with a reflux condenser and a thermometer were introduced cis- or trans-4-{4-[2-(3,5-Bis-trifluoromethyl-benzyloxy)-1-phenyl-ethyl]-piperazin-1-yl}-cyclohexanecarboxylic acid ethyl ester (compound 310 prepared at example 1.4.9; 0.9 g, 1.53 mmoles), HCl 1N (8 ml) and the solution was added at reflux overnight. The pH of the solution was adjusted to 5–6 by addition of aqueous NaOH and was extracted with AcOEt. The combined organic layers were dried over MgSO$_4$ and concentrated. The crude was purified by chromatography on silica gel (eluent: CH$_2$Cl$_2$/MeOH/NH$_3$: 90/10/0.5 then 85/15/1 v/v/v) to afford cis- or trans-4-{4-[2-(3,5-Bis-trifluoromethyl-benzyloxy)-1-phenyl-ethyl]-piperazin-1-yl}-cyclohexanecarboxylic acid (compounds 312 or 313) as a pale yellow solid (0.4 g, 50%) which was converted into the dihydrochloride salt by reaction with HCl in diethyl-ether. It was impossible by NMR to determine which of these two compounds has the cis-conformation and which has the trans-configuration.

Analysis for the dihydrochloride of compound 312:
$^1$H-NMR (DMSO): 8.01 (s, 1H), 7.93 (s, 2H), 7.53 (m, 2H), 7.43 (m, 3H), 4.73 (dd, 2H), 4.64 (t, 1H), 4.16 (dd, 1H), 3.99 (dd,1H), 3.77 (m, 2H), 3.56 (m, 2H), 3.46 (m, 2H), 3.24 (m, 1H), 3.13 (m, 2H), 2.18 (m, 1H), 2.01 (m, 1H), 1.99 (m, 1H), 1.44 (m, 1H), 1.33 (m, 1H).
Mass: (LC/MS APCI+): 559 (MH+).

Analysis for the dihydrochloride of compound 313:
$^1$H-NMR (DMSO): 8.0 (s, 1H), 7.88 (s, 2H), 7.42 (m, 5H), 4.70 (dd, 2H), 4.33 (t, 1H), 4.00 (dd, 1H), 3.92 (dd,1H), 3.54 (m, 2H), 3.21 (m, 2H), 3.17 (m, 1H), 2.84 (m, 2H), 2.74 (m, 2H), 2.58 (m, 1H), 2.06 (m, 1H), 1.92 (m, 1H), 1.51 (m, 1H), 1.37 (m, 1H).
Mass: (LC/MS APCI+): 559 (MH+).

1.4.10. Preparation of compounds of formula I according to process (a.10).

6-{4-[2-(3,5-Bis-trifluoromethyl-benzyloxy)-1-phenyl-ethyl]-piperazin-1-yl}-hexanoic acid (2,4-dimethoxy-benzyloxy)-amide (Compound 314).

In a round-bottomed flask, 0.85 g (1.55 mmoles) of 6-{4-[2-(3,5-Bis-trifluoromethyl-benzyloxy)-1-phenyl-ethyl]-piperazin-1-yl}-hexanoic acid (compound 234), 0.28 g (2.02 mmoles) of hydroxybenzotriazole, 0.427 g (2.33 mmoles) of 2,4-dimethoxy-benzylhydroxylamine (obtained as described in B. Barlaam, A. Hamon, M. Maudet, Tetrahedron Lett (1998), 39, 7865–7868) and 0.456 g (2.33 mmoles) of 1-(3-dimethylaminopropyl)-3-ethylcarbodiimide hydrochloride, were introduced. The mixture was stirred at room temperature for 21 hours. The mixture was diluted with 40 ml of EtOAc and washed with water, saturated sodium bicarbonate, brine, dried over magnesium sulfate and concentrated under reduced pressure affording 1.27 g of crude product. Purification by chromatography on silica gel (eluent: ethylacetate/CH$_3$OH 94/6) gave 71% of 6-{4-[2-(3,5-Bis-trifluoromethyl-benzyloxy)-1-phenyl-ethyl]-piperazin-1-yl}-hexanoic acid (2,4-dimethoxy-benzyloxy)-amide (compound 314).

Analysis for compound 314:
$^1$H-NMR (DMSO): 7.94 (s, 1H), 7.84 (s, 2H), 7.2 (m, 6H), 6.5 (m, 2H), 4.68 (s, 2H), 4.64 (s, 2H), 3.89 (m, 1H), 3.75 (m, 7H), 3.6 (m, 1H), 2.45–2.2 (m,9H), 2.12 (t, 2H), 1.88 (t, 2H), 1.45 (m, 2H), 1.33 (m, 2H), 1.23 (m, 2H).
Mass: (LC/MS APCI+): 712 (MH+)

6-{4-[2-(3,5-Bis-trifluoromethyl-benzyloxy)-1-phenyl-ethyl]-piperazin-1-yl}-hexanoic acid hydroxyamide (compound 315) is prepared by deprotection of the O-protected hydroxamate 314 by trifluoroacetic acid:

In a round-bottomed flask fitted with a reflux condenser and a thermometer, 0.97 g (1.36 mmoles) of 6-{4-[2-(3,5-Bis-trifluoromethyl-benzyloxy)-1-phenyl-ethyl]-piperazin-1-yl}-hexanoic acid (2,4-dimethoxy-benzyloxy)-amide (compound 314) in 10 ml 5% TFA-dichloromethane solution, was stirred at room temperature during one day. Again, 1 ml of TFA was added. The reaction mixture turned deep purple. The mixture was evaporated in vacuum, diluted in CH$_3$OH and filtered to remove insoluble material. Evaporation of the filtrate gave 1.17 g of a brown oil which was purified by chromatography on silica gel affording 0.21 g of 6-{4-[2-(3,5-Bis-trifluoromethyl-benzyloxy)-1-phenyl-ethyl]-piperazin-1-yl}-hexanoic acid hydroxyamide (compound 315) transformed to its dimaleate salt by adding 0.085 g of maleic acid.

Analysis for monohydrated dimaleate of compound 315:
$^1$H-NMR (DMSO): 7.96 (s,1H), 7.86 (s, 2H), 7.3 (m, 5H), 6.11 (s, 4H), 4.67 (s,2H), 3.9–3.8 (m, 3H), 3.5–2.6 (m, 10H), 1.94 (s, 2H), 1.6–1.4 (m, 4H), 1.25 (m, 2H).
Mass: (LC/MS APCI+): 562 (MH+)

EXAMPLE 2

Preparation of Compounds of Formula I According to Process (b)

4-[2-(3,5-Bis-trifluoromethyl-benzyloxy)-1-(4-methoxycarbonylmethyl-piperazin-1-yl)-ethyl]-benzoic acid methyl ester (compound 316).

Following the method described in Lin C.-H. et al., J. Med. Chem. (1993), 36, 2208–2218:

In a round-bottomed flask fitted with a reflux condenser and a thermometer were introduced {4-[2-(3,5-Bis-trifluoromethyl-benzyloxy)-1-(4-bromo-phenyl)-ethyl]-piperazin-1-yl}-acetic acid methyl ester (compound 184 prepared at example 1.4.1 above; 0.5 g, 0.8 mmoles), Et$_3$N (0.26 ml, 1.8 mmoles), MeOH (3 ml) and DMF (9 ml). The mixture was purged with N$_2$ and a stream of CO was passed into the mixture for 10 min. A solution of Pd(OAc)$_2$ (19.2 mg, 10% moles) and Diphenylphosphinopropane (Dppp) (33 mg, 10% moles) dissolved in MeOH/DMF 1/3 (0.65 ml), purged with N$_2$, was then added to the mixture. The reaction mixture was heated at 70° C. and CO was bubbled through the reaction mixture overnight. The reaction mixture was purged with N$_2$, quenched with NaHCO$_3$ and extracted with AcOEt. The combined organic layers were dried over MgSO$_4$ and concentrated to give an oil which was purified by chromatography on silica gel (eluent: CH$_2$Cl$_2$/MeOH/

NH₃: 99.5/0.5/0.1 v/v/v) to afford 4-[2-(3,5-Bis-trifluoromethyl-benzyloxy)-1-(4-methoxycarbonylmethyl-piperazin-1-yl)-ethyl]-benzoic acid methyl ester (compound 316; 150 mg, 30%).

Analysis for compound 316:
¹H-NMR (DMSO): 7.95 (s, 2H), 7.90 (s, 1H), 7.75 (d, 2H), 7.45 (d, 2H), 4.65 (s, 2H), 4.0–3.65 (m, 3H), 3.90 (s, 3H), 3.60 (s, 3H), 3.15 (s, 2H), 2.60–2.30 (m, 8H).

EXAMPLE 3

Preparation of Compounds of Formula I According to Process (c)

{4-[2-(3,5-Bis-trifluoromethyl-benzyloxy)-1-(4-cyano-phenyl)-ethyl]-piperazin-1-yl}-acetic acid methyl ester (compound 317).

Following the method described in Tschaen D. M. et al., JOC (1995), 60, 4324–4330:

A round-bottomed flask charged with Pd(OAc)₂ (36 mg, 4% moles) and P(o-tol)3 (192 mg, 20% mol) was evacuated and then vented to nitrogen. N-methylpyrrolydone (NMP) (4 ml) was added and the mixture was heated at 50° C. for 30 min. Diethylzinc in hexane (0.29 ml) was added and the mixture was maintained at 50° C. for an additional 30 min. The mixture was cannulated into a flask containing a solution of {4-[2-(3,5-Bis-trifluoromethyl-benzyloxy)-1-(4-bromo-phenyl)-ethyl]-piperazin-1-yl}-acetic acid methyl ester (compound 184 prepared at example 1.4.1 above; 2.33 g, 4.0 mmoles) and Zn(CN)₂ (0.47 g, 4.0 mmoles) dissolved in NMP (6 ml). The reaction mixture was heated at 60° C. for 3 hours. The eluent was evaporated and the residue was taken up in diethylether. The precipitate was filtered and the organic solution was washed with ammonium hydroxyde, dried over MgSO₄ and concentrated. The residue was purified by chromatography on silica gel (eluent: Hex/AcOEt: 75/25 v/v) to give {4-[2-(3,5-Bis-trifluoromethyl-benzyloxy)-1-(4-cyano-phenyl)-ethyl]-piperazin-1-yl}-acetic acid methyl ester (compound 317; 0.9 g, 34%).

Analysis for compound 317:
¹H-NMR (DMSO): 7.95 (s, 1H), 7.85–7.75 (m, 4H), 7.50 (d, 2H), 4.65 (s, 2H), 3.95–3.65 (m, 3H), 3.60 (s, 3H), 3.15 (s, 2H), 2.60–2.30 (m, 8H).

Mass: (LC/MS APCI+): 530(MH+)

EXAMPLE 4

Preparation of Compounds of Formula I According to Process (d)

4-[2-(3,5-Bis-trifluoromethyl-benzyloxy)-1-(4-carboxymethyl-piperazin-1-yl)-ethyl]-benzoic acid methyl ester hemihydrate (compound 318).

In a round-bottomed flask was introduced 4-[2-(3,5-Bis-trifluoromethyl-benzyloxy)-1-(4-methoxycarbonylmethyl-piperazin-1-yl)-ethyl]-benzoic acid methyl ester (compound 316 prepared at example 2 above; 2.17 g, 3.86 mmoles) dissolved in MeOH (30 ml). To this solution cooled at 0° C. was added KOH (0.54 g, 9.62 mmoles) dissolved in MeOH (20 ml). The reaction mixture was allowed to stand at room temperature overnight. The reaction was cooled to 0° C., quenched by addition of HCl 0.1 N and extracted with CH₂Cl₂. The combined organic layers were dried over MgSO₄ and concentrated. The residue was purified by chromatography on silica gel (eluent: CH₂Cl₂/MeOH/H₂O: 95/5/0.5) to yield 4-[2-(3,5-bis-trifluoromethyl-benzyloxy)-1-(4-carboxymethyl-piperazin-1-yl)-ethyl]-benzoic acid methyl ester hemihydrate (compound 318; 1.5 g, 71%).

Analysis for the hemihydrate of compound 318:
¹H-NMR (DMSO): 7.93 (s, 1H), 7.90 (d, 2H), 7.79 (s, 2H), 7.47 (d, 2H), 4.65 (s, 2H), 3.95–3.7 (m, 2H), 3.85 (s, 3H), 3.72 (t, 1H), 3.08 (s, 2H), 2.65–2.45 (m, 8H).

Mass: (LC/MS APCI+): 549 (MH+).

4-[2-(3,5-Bis-trifluoromethyl-benzyloxy)-1-(4-carboxymethyl-piperazin-1-yl)-ethyl]-benzoic acid hemihydrate (compound 319).

In a round-bottomed flask were introduced 4-[2-(3,5-Bis-trifluoromethyl-benzyloxy)-1-(4-methoxycarbonylmethyl-piperazin-1-yl)-ethyl]-benzoic acid methyl ester (compound 316 prepared at example 2; 2 g, 3.56 mmoles), KOH (0.4 g, 7.12 mmoles) and MeOH. The reaction mixture was heated at 60° C. for 6 hours. MeOH was removed under reduce pressure and the residue was taken up by water. The pH was adjusted to 3–4 and the solution was extracted with AcOEt. The organic combined layers were dried over MgSO₄ and concentrated. The residue was purified by chromatography on silica gel (eluent: CH₂Cl₂/MeOH/H₂O: 90/10/1 v/v/v) to give 4-[2-(3,5-Bis-trifluoromethyl-benzyloxy)-1-(4-carboxymethyl-piperazin-1-yl)-ethyl]-benzoic acid hemihydrate (compound 319; 0.88 g, 45%).

Analysis for the hemihydrate of compound 319:
¹H-NMR (DMSO): 7.93 (s, 1H), 7.90 (d, 2H), 7.81 (s, 2H), 7.43 (d, 2H), 4.65 (s, 2H), 3.85 (dd, 1H), 3.8 (dd, 1H), 3.72 (t, 1H), 3.09 (s, 2H), 2.65–2.45 (m, 8H).

Mass: (LC/MS APCI+): 535 (MH+).

{4-[2-(3,5-Bis-trifluoromethyl-benzyloxy)-1-(4-carbamoyl-phenyl)-ethyl]-piperazin-1-yl}-acetic acid (compound 321) and 4-[2-(3,5-Bis-trifluoromethyl-benzyloxy)-1-(4-carbamoylmethyl-piperazin-1-yl)-ethyl]-benzamide (compound 322).

In a small autoclave, 1.5 g (2.73 mmoles) of 4-[2-(3,5-Bis-trifluoromethyl-benzyloxy)-1-(4-carboxymethyl-piperazin-1-yl)-ethyl]-benzoic acid methyl ester (compound 318) were dissolved in methanol. The solution was saturated with NH3 and heated at 100° C. for three days. Methanol was then evaporated and the crude product was purified by chromatography (eluent: CH₂Cl₂/MeOH/NH₃: 80/20/0.5 v/v/v) to give 880 mg of {4-[2-(3,5-Bis-trifluoromethyl-benzyloxy)-1-(4-carbamoyl-phenyl)-ethyl]-piperazin-1-yl}-acetic acid (compound 321) as a grey solid. 4-[2-(3,5-Bis-trifluoromethyl-benzyloxy)-1-(4-carbamoylmethyl-piperazin-1-yl)-ethyl]-benzamide (compound 322) was isolated as a side product (150 mg).

Analysis for compound 321:
¹H-NMR (DMSO): 7.95 (s, 1H), 7.85–7.8 (m, 5H), 7.38 (d, 2H), 7.2 (s, 1H), 4.66 (s, 2H), 3.95–3.6 (m, 3H), 3.02 (s, 2H), 2.65–2.35 (m, 8H).

Mass: (LC/MS APCI+): 534 (MH+).

Analysis for compound 322:
¹H-NMR (DMSO): 7.96 (s, 1H), 7.85 (s+d, 3H), 7.37 (d, 2H), 7.2 (s, 1H), 7.0–6.9 (s+s, 2H), 4.67 (s, 2H), 3.92 (dd, 1H), 3.82 (dd, 1H), 3.71 (t, 1H), 2.79 (s, 2H), 2.55–2.35 (m, 8H).

Mass: (LC/MS APCI+): 533 (MH+).

EXAMPLE 5

Preparation of Compounds of Formula I According to Process (f)

Dihydrochloride of {4-[2-(3,5-Bis-trifluoromethyl-benzyloxy)-1-(4-cyano-phenyl)-ethyl]-piperazin-1-yl}-acetic acid (compound 320).

In a round-bottomed flask were introduced compound {4-[2-(3,5-Bis-trifluoromethyl-benzyloxy)-1-(4-cyano-phenyl)-ethyl]-piperazin-1-yl}-acetic acid methyl ester (compound 317 prepared at example 2; 0.9 g, 1.7 mmoles), KOH (0.24 g, 4.25 mmoles) and MeOH. The reaction mixture was stirred at room temperature overnight. The reaction mixture was diluted with water and the pH was adjusted to 3. The solution was extracted with CH$_2$Cl$_2$ and the combined organic layers were dried over Na$_2$SO$_4$ and concentrated. The residue was crystallized from diethylether/HCl to give the dihydrochloride of {4-[2-(3,5-Bis-trifluoromethyl-benzyloxy)-1-(4-cyano-phenyl)-ethyl]-piperazin-1-yl}-acetic acid (compound 320; 0.8 g, 80%).

Analysis for the dihydrochloride of compound 320:

$^1$H-NMR (DMSO): 7.86 (s, 1H), 7.71 (d, 2H), 7.62 (s, 2H), 7.52 (d, 2H), 4.58 (s, 2H), 4.1–3.8 (m, 3H), 3.72 (s, 2H), 3.35–3.15 (m, 4H), 2.9–2.4 (m, 4H).

Mass: (LC/MS APCI+): 516 (MH+).

EXAMPLE 6

Preparation of Compounds of Formula I According to Process (g)

{4-[1-(2-Amino-phenyl)-2-(3,5-bis-trifluoromethyl-benzyloxy)-ethyl]-piperazin-1-yl}-acetic acid methyl ester (compound 323)

In a round-bottomed flask fitted with a reflux condenser and a thermometer were introduced {4-[2-(3,5-Bis-trifluoromethyl-benzyloxy)-1-(2-nitro-phenyl)-ethyl]-piperazin-1-yl}-acetic acid methyl ester (compound 190 prepared at example 1.4.1 above; 2 g, 3.64 mmoles), SnCl$_2$ (3.45 g, 18.2 mmoles) and MeOH (40 ml) and the reaction mixture was heated at 60° C. for 3 hours. MeOH was evaporated in vacuo and the crude was taken up in water. The pH was adjusted to 8–9 by addition of aqueous NaOH and the solution was extracted with AcOEt. The combined organic phases were dried over MgSO$_4$ and concentrated. The resulting oil was purified by chromatography on silica gel (eluent: CH$_2$Cl$_2$/MeOH/NH$_3$: 99/1/0.1 v/v/v) to yield {4-[1-(2-Amino-phenyl)-2-(3,5-bis-trifluoromethyl-benzyloxy)-ethyl]-piperazin-1-yl}-acetic acid methyl ester (compound 323; 1.7 g, 90%) as a yellow oil.

Analysis for compound 323:

$^1$H-NMR (DMSO): 7.95 (s, 1H), 7.90 (s, 2H), 6.95 (t, 1H), 6.55–6.45 (m, 3H), 4.90 (s, NH2), 4.65 (s, 2H), 3.85 (dd, 1H), 3.65 (dd, 1H), 3.40 (t, 1H), 3.15 (s, 2H), 2.55–2.35 (m, 8H).

Mass: (LC/MS APCI+): 520 (MH+).

{4-[1-(2-Amino-phenyl)-2-(3,5-bis-trifluoromethyl-benzyloxy)-ethyl]-piperazin-1-yl}-acetic acid (compound 324)

In a round-bottomed flask were introduced {4-[1-(2-Amino-phenyl)-2-(3,5-bis-trifluoromethyl-benzyloxy)-ethyl]-piperazin-1-yl}-acetic acid methyl ester (compound 323; 1.3 g, 2.5 mmoles), KOH (0.35 g, 6.3 mmoles) and MeOH (20 ml). The reaction mixture was stirred at room temperature for 6 hours. MeOH was removed under reduce pressure and the residue was taken up in water. The pH was adjusted to 6 and the solution was extracted with CH$_2$Cl$_2$. The combined organic layers were dried over MgSO$_4$ and concentrated. The residue (1.1 g, 88%) was recrystallized from diethylether to give {4-[1-(2-Amino-phenyl)-2-(3,5-bis-trifluoromethyl-benzyloxy)-ethyl]-piperazin-1-yl}-acetic acid (compound 324; 0.75 g, 60%) as white needles.

Analysis for compound 324:

$^1$H-NMR (DMSO): 7.89 (s, 1H), 7.82 (s, 2H), 6.97 (t, 1H), 6.55–6.4 (m, 3H), 4.6 (dd, 2H), 3.85 (dd, 1H), 3.68 (dd, 1H), 3.52 (t, 1H), 3.34 (s, 2H), 3.2–3.0 (m, 4H), 2.8–2.5 (m, 4H).

Mass: (LC/MS APCI+): 506 (MH+).

Another aspect of the invention concerns the use of a therapeutically effective amount of an α-arylethylpiperazine derivative of formula I, an individual enantiomer, diastereoisomer or non-toxic pharmaceutically acceptable salt thereof for the prevention and/or treatment of a condition associated with pathological levels of substance P in a patient.

As used herein, "pathological levels of substance P" means a level of substance P sufficient to cause a pathological process leading to pain, emesis, pulmonary diseases such as asthma and bronchitis or allergic rhinitis. In a preferred embodiment, the present invention concerns the use of a therapeutically effective amount of an α-arylethylpiperazine derivative of formula I, an individual enantiomer, diastereoisomer or non-toxic pharmaceutically acceptable salt thereof for the prevention and/or treatment of asthma and/or allergic rhinitis.

As used herein, "patient" means any living animal in need of prevention and/or treatment of symptoms associated with pathological levels of substance P. Such patients include most preferably humans.

As used herein, "a therapeutically effective amount" of an α-arylethylpiperazine derivative of formula I an amount sufficient to at least ameliorate or prevent the symptoms of the patients. This amount may vary within wide limits depending on a series of factors such as the age and sex of the patient, the state of condition being treated, the overall health of the patient, the method of administration, the severity of side-effects and the like.

Preferably, the daily dosage is administered once or several times, depending on factors such as the severity of the condition, the mode of administration, the tolerance by the patient.

Accordingly, a further aspect of the invention concerns a pharmaceutical composition comprising a therapeutically effective amount of an α-arylethylpiperazine derivative of formula I, an individual enantiomer, diastereoisomer or non-toxic pharmaceutically acceptable salt thereof, as well as pharmaceutically acceptable solid or liquid excipients or carriers therefor.

Suitable pharmaceutically acceptable excipient or carriers are the ones well known by the person skilled in the art and are prepared according to the methods generally applied by pharmacists, and may include solid, liquid or gazeous, non-toxic pharmaceutically acceptable vehicles. The percentage of active compound/pharmaceutically acceptable carrier may vary within very large ranges, only limited by the tolerance and the possible side-effects upon the patient. The limits are particularly determined by their frequency of administration.

For preparing solid compositions such as tablets, the compound according to the invention is mixed with conventional tabletting ingredients such as corn starch, lactose, sucrose, sorbitol, talc, stearic acid, magnesium stearate, dicalcium phosphate, gum. Solid formulations may also include sustained release excipients such as cellulose ester derivatives or any other known matricial excipient. Tablet formation by wet or dry granulation may take place according to the methods well known by pharmacists.

Liquid formulations include syrups, aqueous or oil suspensions, flavoured emulsions . . . . Compositions for inhalation include solutions and suspensions in pharmaceutically aqueous or organic solvents or powders, suitable for oral or nasal administration.

As indicated above, the α-arylethylpiperazine derivatives of formula I, their individual enantiomers, diastereisomers and pharmaceutically acceptable salts thereof have the property of acting as neurokinin antagonists, without interacting with calcium channels. These advantageous properties are demonstrated by the following studies.

1. Characterisation of the interactions between a test substance and the human recombinant $NK_1$ receptor.

Tachykinin receptors are divided into three subclasses: $NK_1$, $NK_2$ and $NK_3$ receptors. $NK_1$ receptors are found on sensory nerve terminals, on smooth muscles and on immune cells. Their activation by substance P is involved in several pathophysiological states including, but not restricted to, asthma (mucus secretion, bronchoconstriction, plasma extravasation . . . ), emesis and nociception (Bertrand and Geppetti, TIPS (1996), 17, 255–259; Longmore et al. DN&P (1995), 1, 1–23).

The recombinant human $NK_1$ receptor is coded by a gene located on chromosome 2 (Gerard N. et al., Biochemistry (1991), 30, 10640–10646.). Besides being more ethical, the use of human cloned receptors offers the advantage of population homogeneity (avoidance of cross binding of the test substances, including the radioligand, with other receptors or other receptor subtypes) and of being cloned from the target species i.e. human.

$NK_1$ receptors may be studied with [4,53H-Leu10] substance P, a commercially available radioligand. It offers a good selectivity, a high affinity and a low non specific binding (Aharony et al., The Journal of Pharmacology and Experimental Therapeutics (1991), 259, 146–155).

The following test was designed to assess the affinity of test substances for human recombinant $NK_1$ receptors expressed in Chinese Hamster Ovarian (CHO) cells.

1.1. Cells

CHO cells expressing the human recombinant $NK_1$ receptor are used. The cells were obtained from Euroscreen (Brussels, Belgium).

Cells expressing the human $NK_1$ receptor are routinely cultured in 175 cm2 flasks containing 75 ml of medium F12 (Ham) enriched with 2 mmol/l L-glutamine, 100 IU/ml penicilline, 100 µg/ml streptomycine, 1% sodium pyruvate, 2.5 µg/ml fungizone amphotericin B, 400 µg/ml geneticin and supplemented with 10% foetal calf serum. The cells are grown at 37° C. in a humidified atmosphere composed of 5% CO2 and 95% air. When subcultured, the cells are seeded at a concentration of 50,000 cells/cm2.

1.2. Experimental Procedure 1.2.1. Membrane Preparation

Confluent cells are gently scraped and resuspended in 25 ml of phosphate buffered saline without calcium and magnesium. The cellular suspension is centrifuged at 1500×g for 3 min (4° C.). The cell pellet is homogenized in a 15 mmol/l Tris-HCl (pH 7.5) buffer, 2 mmol/l $MgCl_2$, 0.3 mmol/l EDTA, 1 mmol/l EGTA. The crude membrane fraction is collected by two consecutive centrifugation steps at 40,000×g for 25 min (4° C.). The final pellet is resuspended in 20 mmol/l Tris-HCl (pH 7.4), 250 mmol/l sucrose buffer at a protein concentration ranging from 2 to 6 mg/ml and stored in liquid nitrogen.

1.2.2. Test Design

The inhibition constant (Ki) is determined using increasing concentrations of the test substance. The concentration range usually encompasses 6 log units with variable steps (0.3 to 1 log). Assays are performed in mono- or duplicate.

Membranes are incubated at 25° C. for 60 min in 0.5 ml of a 50 mmol/l Tris-HCl buffer (pH 7.4) containing 2 mmol/l $MgCl_2$, 100 µg/ml bacitracine, 0.1 to $0.4 \times 10^{-9}$ mol/l of [4,5$^3$H-Leu$^{10}$] substance P (specific activity>100 Ci/mmol) and increasing concentrations of the test substance. The non specific binding (NSB) is defined as the residual binding observed in the presence of a concentration in excess of reference substance (e.g. $10^{-6}$ mol/l CP-96,345). Membrane-bound and free radioligands are separated by rapid filtration through glass fiber filters (equivalent to Whatman GF/C or GF/B; VEL, Belgium) presoaked in 0.1% polyethyleneimine to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a β-counter (Tri-Carb 1900 or TopCount 9206, Camberra Packard, Belgium, or any other equivalent counter).

1.3. Data Analysis

Data analysis is performed by a computerized non linear (NLIN) curve fitting method using a set of equations describing several binding models assuming populations of independent non-interacting receptors which obey to the law of mass action (Weiland, G. A. and P. B. Molinoff, Life Science (1981), 29, 313–330; Molinoff P. et al., Life Science (1981), 29, 427–443). Initial values for the different variables may be provided by the experimenter.

1.4. Results

Table A below summarizes the results obtained with the compounds according to the invention. In this Table, $pIC_{50}=-\log IC_{50}$, $IC_{50}$ being the concentration of compound necessary to inhibit by 50% the specific binding of [4,5$^3$H] substance P.

TABLE A

Binding of compounds of formula I to $NK_1$ receptors

| Cpd No. | Free base/Salt | $pIC_{50}$ |
| --- | --- | --- |
| 136 | 2 maleate | 7.1 |
| 138 | 2 maleate | 8.0 |
| 139 | 2 maleate | 8.2 |
| 141 | 2 maleate | 8.1 |
| 142 | 2 maleate | 8.1 |
| 143 | 2 HCl | 7.4 |
| 144 | 2 HCl | 7.4 |
| 145 | 2 HCl | 7.5 |
| 146 | 1 HCl | 7.8 |
| 147 | 2 HCl.2 $H_2O$ | 8.0 |
| 148 | 2 maleate.½$H_2O$ | 7.4 |
| 149 | 2 maleate.½$H_2O$ | 7.2 |
| 150 | 2 maleate | 8.3 |
| 151 | 2 maleate | 7.7 |
| 152 | 2 maleate | 7.9 |
| 155 | 2 maleate | 7.8 |
| 156 | 2 maleate | 8.1 |
| 157 | 2 HCl.½$H_2O$ | 8.2 |
| 158 | 2 maleate | 8.1 |
| 160 | 2 HCl | 7.5 |
| 161 | 3 HCl | 8.1 |
| 162 | 3 HCl | 8.1 |
| 164 | 2 maleate | 7.4 |
| 170 | 3 HCl.½$H_2O$ | 7.3 |
| 171 | — | 7.1 |
| 173 | 2 HCl | 7.6 |
| 174 | 2 HCl | 7.4 |
| 175 | 2 HCl.1 $H_2O$ | 8.3 |
| 176 | 2 HCl | 7.6 |
| 177 | 2 HCl | 8.2 |
| 182 | 2 maleate | 7.0 |
| 191 | 2 HCl | 7.2 |
| 208 | 2 maleate | 7.2 |

TABLE A-continued

Binding of compounds of formula I to $NK_1$ receptors

| Cpd No. | Free base/Salt | $pIC_{50}$ |
|---|---|---|
| 219 | 2 maleate | 9.5 |
| 227 | 2 maleate | 7.4 |
| 229 | 2 HCl | 7.1 |
| 230 | 2 HCl.½H$_2$O | 7.3 |
| 231 | 2 HCl.1 H$_2$O | 7.1 |
| 232 | 2 maleate | 7.3 |
| 233 | 2 HCl | 7.5 |
| 234 | ½maleate | 7.8 |
| 235 | 2 maleate | 7.2 |
| 236 | 2 maleate | 7.1 |
| 237 | 2 maleate | 7.0 |
| 239 | 2 HCl | 7.5 |
| 241 | 2 HCl.1 H$_2$O | 8.1 |
| 242 | 2 HCl.½H$_2$O | 8.1 |
| 243 | 2 maleate.½H$_2$O | 7.2 |
| 244 | — | 7.4 |
| 245 | 1 H$_2$O | 7.2 |
| 246 | 2 maleate | 7.1 |
| 248 | 2 maleate | 7.6 |
| 249 | 2 maleate | 7.5 |
| 250 | 2 HCl | 7.1 |
| 251 | 1 H$_2$O | 8.1 |
| 252 | 1 H$_2$O | 7.7 |
| 253 | 2 maleate | 7.2 |
| 254 | ½H$_2$O | 7.3 |
| 255 | 2 HCl | 7.1 |
| 265 | 2 HCl | 7.1 |
| 269 | 2 maleate | 7.0 |
| 271 | 1 maleate.1 H$_2$O | 7.4 |
| 273 | 2 HCl.3 H$_2$O | 8.5 |
| 274 | 2 HCl.1 H$_2$O | 7.9 |
| 275 | 2 HCl.5/2 H$_2$O | 8.4 |
| 277 | 2 HCl.1 H$_2$O | 8.0 |
| 279 | 2 HCl.1 H$_2$O | 8.7 |
| 281 | 2 HCl.½H$_2$O | 8.1 |
| 283 | 2 HCl.³⁄₂H$_2$O | 7.6 |
| 284 | 2 maleate.1 H$_2$O | 7.3 |
| 285 | 2 maleate.1 H$_2$O | 7.3 |
| 287 | 2 HCl.1 H$_2$O | 7.5 |
| 288 | 2 maleate.½H2O | 8.3 |
| 289 | 2 HCl | 8.5 |
| 291 | 2 HCl | 7.6 |
| 292 | 2 maleate | 7.8 |
| 293 | 2 maleate | 7.2 |
| 294 | 2 maleate | 7.9 |
| 295 | — | 7.2 |
| 297 | 2 HCl | 7.7 |
| 298 | 2 HCl | 7.8 |
| 299 | 2 HCl | 7.8 |
| 300 | 2 HCl | 7.5 |
| 301 | 2 HCl.⅓C$_3$H$_8$O | 7.8 |
| 302 | 2 HCl | 8.4 |
| 303 | 2 HCl | 8.3 |
| 304 | 2 maleate | 8.1 |
| 305 | 2 HCl.³⁄₂H$_2$O | 7.1 |
| 306 | 1 H$_2$O | 7.5 |
| 307 | 2 HCl | 7.8 |
| 308 | 2 HCl.³⁄₄H$_2$O | 7.9 |
| 312 | 2 HCl | 7.6 |
| 313 | 2 HCl | 7.8 |
| 315 | 2 maleate.1 H$_2$O | 8.3 |
| 320 | 2 HCl | 7.0 |

2. Characterization of the interactions between a test substance and the verapamil binding site of the L-type calcium channel.

2.1. Membrane Preparation

200–250 g male Sprague-Dawley rats are sacrificed by decapitation. Cerebral cortices are quickly dissected on ice and homogenized in a 20 mmol/l Tris-HCl (pH 7.4) buffer containing 250 mmol/l sucrose (buffer A). The homogenate is centrifuged at 30,000 g for 15 min at 4° C. The resulting crude membrane pellet is resuspended in a 50 mmol/l Tris-HCl (pH 7.4) buffer and incubated 15 min at 37° C. before being centrifuged at 30,000×g for 15 min at 4° C. After two more washes under the same conditions, the final pellet is resuspended in buffer A at a protein concentration ranging from 15 to 25 mg/ml and stored in liquid nitrogen.

2.2. Binding Experiments

Binding experiments are essentially performed according to Reynolds J. et al., J. Pharmacol. Exp. Ther. (1986), 237, 731–738. (1986) with slight modifications.

Membranes (120–175 µg/assay) are incubated at 25° C. for 60 min in 0.5 ml of a 50 mmol/l Tris-HCl buffer (pH 7.4) containing 2 mmol/l MgCl$_2$, 0.2 to 0.4×10–9 mol/l of [$^3$H]D888 (85 Ci/mmol; Amersham, Belgium) and 10 µmol/l of the test substance. The non specific binding (NSB) is defined as the residual binding observed in the presence 10 µM verapamil. Membrane-bound and -free radioligands are separated by rapid filtration through glass fiber filters (equivalent to Whatman GF/C or GF/B; VEL, Belgium) presoaked in 0.1% polyethyleneimine to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a β-counter.

2.3. Data Analysis

The inhibition of the radioligand specific binding is calculated as follows:

$$\% \text{ inhibition} = 100 - \left(\frac{B_I - B_{NS}}{B_O - B_{NS}} \times 100\right)$$

where $B_I$ and $B_O$ represent the binding observed in the presence and absence of the test substance respectively; and $B_{NS}$ is the non specific binding.

Data analysis is performed by a computerized non linear curve fitting method using a set of equations describing several binding models assuming competitive interactions between ligands (Weiland G. A. and P. B. Molinoff Life Science (1981), 29, 313–330; Molinoff P. et al. (1981) Life Sci., 29, 427–443).

2.4. Results

Table B below summarizes the results obtained with the compounds according to the invention.

TABLE B

Inhibition of [$^3$H]D888 binding to the verapamil binding site of the L-type calcium channel by 10 µmol/l of test subtances.

| Cpd No. | Free base /Salt | % inhibition* |
|---|---|---|
| 160 | 2 HCl | 0 |
| 229 | 2 HCl | 0 |
| 230 | 2 HCl.½H$_2$O | 0 |
| 231 | 2 HCl, 1 H$_2$O | 0 |
| 232 | 2 maleate | + |
| 233 | 2 HCl | 0 |
| 234 | ½maleate | 0 |
| 235 | 2 maleate | 0 |
| 236 | 2 maleate | 0 |
| 237 | 2 maleate | 0 |
| 239 | 2 HCl | 0 |
| 241 | 2 HCl.1 H$_2$O | + |
| 242 | 2 HCl.½H$_2$O | + |
| 243 | 2 maleate.½H$_2$O | 0 |
| 244 | −+ | |
| 245 | 1 H$_2$O | 0 |
| 246 | 2 maleate | + |
| 248 | 2 maleate | + |

TABLE B-continued

Inhibition of [$^3$H]D888 binding to the verapamil binding site of the L-type calcium channel by 10 µmol/l of test subtances.

| Cpd No. | Free base /Salt | % inhibition* |
|---|---|---|
| 249 | 2 maleate | + |
| 250 | 2 HCl | + |
| 251 | 1 H$_2$O | + |
| 252 | 1 H$_2$O | + |
| 253 | 2 maleate | 0 |
| 254 | ½H$_2$O | 0 |
| 255 | 2 HCl | 0 |
| 265 | 2 HCl | 0 |
| 269 | 2 maleate | 0 |
| 271 | 1 maleate.1 H$_2$O | + |
| 273 | 2 HCl.3 H$_2$O | 0 |
| 274 | 2 HCl.1 H$_2$O | 0 |
| 275 | 2 HCl.⅔H$_2$O | 0 |
| 277 | 2 HCl.1 H$_2$O | 0 |
| 279 | 2 HCl.1 H$_2$O | 0 |
| 281 | 2 HCl.½H$_2$O | + |
| 283 | 2 HCl.⅔H$_2$O | + |
| 285 | 2 maleate.1 H$_2$O | + |
| 287 | 2 HCl.1 H$_2$O | + |
| 291 | 2 HCl | 0 |
| 292 | 2 maleate | + |
| 295 | — | + |
| 297 | 2 HCl | + |
| 298 | 2 HCl | + |
| 299 | 2 HCl | + |
| 300 | 2 HCl | + |
| 301 | 2 HCl.⅓C$_3$H$_8$O | + |
| 302 | 2 HCl | + |
| 303 | 2 HCl | + |
| 304 | 2 maleate | + |
| 305 | 2 HCl.⅔H$_2$O | 0 |
| 306 | 1 H$_2$O | + |
| 307 | 2 HCl | + |
| 312 | 2 HCl | 0 |
| 313 | 2 HCl | 0 |
| 320 | 2 HCl | 0 |

*0: inhibition < 20%; +: inhibition comprised between 20 and 50%
Cpd = compound.

3. Effect of compound on isolated rat aorta contracted by 100 mM KCl.

Rat thoracic aorta depolarized by 100 mM KCl develops a contraction induced by an influx of Ca$^{2+}$ into the smooth muscle cell. An inhibition of this contraction could predict a Ca$^{2+}$ antagonist activity.

The method was adapted from Polster P. et al., J. Pharmacol. Exp. Ther. (1990), 255, 593: rings of thoracic aorta were prepared from male Wistar rats (250–400 g) and mounted under an optimal resting tension of 2 g in 10 ml organ baths containing modified Krebs' solution (NaCl 112 mM, NaHCO$_3$ 25 mM, KCl 5 mM, MgSO$_4$ 1.2 mM, CaCl$_2$ 2.5 mM, KH$_2$PO$_4$ 1 mM and glucose 11.5 mM, pH 7.4). The bathing solution was maintained at a temperature of 37° C. and gassed with 95% O2 and 5% CO$_2$. Isometric contractions were measured with a force transducer connected to an amplifier. A computer system was used to control data acquisition and fluid circulation through electrovalves. Drugs were manually injected into the bath.

Each ring was allowed to equilibrate for 60 min in the modified Krebs' solution. Control contractions were repeatedly induced by a depolarising medium (NaCl 17 mM, NaHCO$_3$ 25 mM, KCl 100 mM, MgSO$_4$ 1.2 mM, CaCl$_2$ 2.5 mM, KH$_2$PO$_4$ 1.2 mM et glucose 11.5 mM, pH 7.4). After obtaining two reproducible control contractions, a 3rd contraction was induced and the test compound was added to the bathing medium for 2 hours. Only preparation in which the contractions were matched were used. Each tissue received only one concentration of the test compound. Appropriate control experiments were conducted in order to test the effect of the solvant.

To normalize data, the change in tension due to the drug was compared to the change of tension due to the solvant and expressed as percentage of the induced relaxation of the initial contraction. Raw data were processed by a computer system and the pD'2 value was calculated following the method of Van Rossum J. M. et al., Arch. Int. Pharmacodyn. Ther. (1963), 143, 299.

Table C below summarizes the results obtained with the compounds according to the invention. This table shows that none of the tested compounds inhibited the contraction induced by 100 mM KCl on isolated rat aorta. These results suggest that a Ca$^{2+}$ antagonist activity is not to be taking into account for these compounds.

TABLE C

Effect of compound on isolated rat aorta contracted by 100 mM KCl

| Cpd No. | Free base/Salt | Result |
|---|---|---|
| 160 | 2 HCl | inactive à 10$^{-5}$ M |
| 229 | 2 HCl | inactive à 10$^{-5}$ M |
| 230 | 2 HCl.½ H$_2$O | inactive à 10$^{-5}$ M |
| 232 | 2 maleate | inactive à 10$^{-5}$ M |
| 233 | 2 HCl | inactive à 10$^{-5}$ M |
| 235 | 2 maleate | inactive à 10$^{-5}$ M |
| 236 | 2 maleate | inactive à 10$^{-5}$ M |
| 237 | 2 maleate | inactive à 10$^{-5}$ M |
| 242 | 2 HCl.½ H$_2$O | inactive à 10$^{-5}$ M |
| 243 | 2 maleate.½ H$_2$O | inactive à 10$^{-5}$ M |
| 265 | 2 HCl | inactive à 10$^{-5}$ M |
| 281 | 2 HCl.1/2 H$_2$O | inactive à 10$^{-5}$ M |
| 287 | 2 HCl.1 H$_2$O | inactive à 10$^{-5}$ M |
| 295 | — | inactive à 10$^{-5}$ M |
| 297 | 2 HCl | inactive à 10$^{-5}$ M |
| 298 | 2 HCl | inactive à 10$^{-5}$ M |
| 299 | 2 HCl | inactive à 10$^{-5}$ M |
| 300 | 2 HCl | inactive à 10$^{-5}$ M |
| 301 | 2 HCl.⅓ C$_3$H$_8$O | inactive à 10$^{-5}$ M |
| 303 | 2 HCl | inactive à 10$^{-5}$ M |
| 304 | 2 maleate | inactive à 10$^{-5}$ M |
| 312 | 2 HCl | inactive à 10$^{-5}$ M |

4. Effect of compound on isolated guinea pig ileum contracted by substance P.

Measuring the effect of compounds in isolated guinea pig ileum stimulated by substance P is a functional test relevant to determine potency of the compounds and nature of the NK$_1$ antagonism. The method was adapted from Meini S. et al., Neuropeptides (1995), 28, 99: segments of ileum were prepared from male Dunkin-Hartley guinea pig (300–600 g) and mounted under an optimal resting tension of 0.5 g in 10 ml organ baths containing modified Tyrode solution (NaCl 136.9 mM, NaHCO$_3$ 11.9 mM, KCl 2.7 mM, MgCl$_2$ 1.05 mM, CaCl$_2$ 1.8 mM, NaH$_2$PO$_4$ 0.42 mM and glucose 5.6 mM, atropine 5 µM, indomethacine 3 µM and chlorpheniramine 1 µM, pH 6.8). The bathing solution was maintained at a temperature of 37° C. and gassed with 95% O$_2$ and 5% CO$_2$. Isometric contractions were measured with a force transducer connected to an amplifier. A computer system was used to control data acquisition and fluid circulation through electrovalves. Drugs were manually injected into the bath.

Each segment was allowed to equilibrate for 60 min in the modified Tyrode solution. Control contractions were repeatedly induced by a 30 nM substance P. After obtaining reproducible control contractions, six cumulative concentration-response curves to substance P (0.01 nM to 1 µM) were constructed in the absence or presence of the test compound (incubation time: 30 min). Only preparation in which the control contractions were matched were used. Each tissue received four concentrations of the test compound. Appropriate control experiments were conducted in order to test the effect of the solvent.

Raw data were processed by a computer system and the $pD_2$, $pD'_2$ and/or $pA_2$ values were calculated following the method of Van Rossum J. M. et al., Arch. Int. Pharmacodyn. Ther. (1963), 143, 299 or Arunlakshana O. and Schild H. O., Br. J. Pharmacol. (1959), 14, 48.

What is claimed is:

1. An α-arylethylpiperazine of formula I'

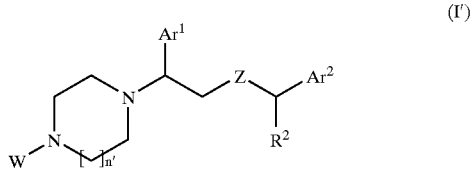

(I')

wherein

Z represents an oxygen atom;

n' represents 1;

$R^2$ represents a hydrogen atom or a methyl group;

W represents (i) a cyclohexyl group substituted by a COOH, or (ii) a group of formula $R^1$—$(CH_2)_n$—X—$(CH_2)_m$— in which $R^1$ represents a CN, $CONHSO_2$alkyl, COOH, COOalkyl, $SO_3H$, $PO(OH)_2$, a phenyl group mono-substituted by COOH, a tetrazole of the formula

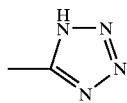

or a triazolone of formula

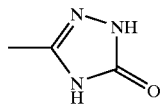

X represents a single bond, an oxygen atom or a methylene group;

m represents 1 or 2, provided that m is not 1 when X is an oxygen atom;

n represents 0, 1 or 2, $Ar^1$ represents phenyl, a mono-, di- or tri-substituted phenyl group in which the substituents are a halogen atom, an alkyl group, CN or $NO_2$;

$Ar^2$ represents a substituted aryl group of formula

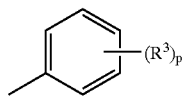

in which $R^3$ represents a halogen atom or a trifluoromethyl group;

p represents 1, 2 or 3;

the alkyl groups being linear or branched and having 1 to 4 atoms of carbon, or non-toxic pharmaceutically acceptable salt, individual optical isomer, or individual diastereoisomer thereof.

2. A pharmaceutical composition comprising a therapeutically effective amount of an α-arylethylpiperazine according to claim 1, or an individual enantiomer, diastereoisomer or non-toxic pharmaceutically acceptable salt thereof, and pharmaceutically acceptable solid or liquid excipient or carrier therefor.

3. The α-arylethylpiperazine according to claim 1 selected from the group consisting of:

[2-(4-{2-[1-(3,5-Bis-trifluoromethyl-phenyl)-ethoxy]-1-phenyl-ethyl}-piperazin-1yl) -ethoxy]-acetic acid;

(4-{2-[1-(3,5-Bis-trifluoromethyl-phenyl)-ethoxy]-1-phenyl-ethyl}-piperazin-1-yl -acetic acid;

4-{4-[2-(3,5-Bis-trifluoromethyl-benzyloxy)-1-phenyl-ethyl]-piperazin-1-yl}-cyclohexanecarboxylic acid;

6-{4-[2-(3,5-Bis-trifluoromethyl-benzyloxy)-1-phenyl-ethyl]-piperazin-1-yl}-hexanoic acid;

{4-[2-(3,5-Bis-trifluoromethyl-benzyloxy)-1-phenyl-ethyl]-piperazin-1-yl}-acetonitrile;

3-{4-[2-(3,5-Bis-trifluoromethyl-benzyloxy)-1-phenyl-ethyl]-piperazin-1-yl}-propane-1-sulfonic acid;

5-{4-[2-(3,5-Bis-trifluoromethyl-benzyloxy)-1-phenyl-ethyl]-piperazin-1-yl}-pentanoic acid;

(2-{4-[2-(3,5-Bis-trifluoromethyl-benzyloxy)-1-phenyl-ethyl]-piperazin-1-yl}-ethoxy)-acetic acid;

{4-[2-(3,5-Bis-trifluoromethyl-benzyloxy)-1-phenyl-ethyl]-piperazin-1-yl}-acetic acid;

{4-[2-(3,5-Bis-trifluoromethyl-benzyloxy)-1-(3,4,5-trifluoro-phenyl)-ethyl]-piperazin-1-yl}-acetic acid;

4-{4-[2-(3,5-Bis-trifluoromethyl-benzyloxy)-1-phenyl-ethyl]-piperazin-1-ylmethyl}-benzoic acid;

{4-[2-(3,5-Dibromo-benzyloxy)-1-phenyl-ethyl]-piperazin-1-yl}-acetic acid;

{4-[2-(3,5-Bis-trifluoromethyl-benzyloxy)-1-para-tolyl-ethyl]-piperazin-1-yl}-acetic acid;

(2-{4-[2-(3,5-Bis-trifluoromethyl-benzyloxy)-1-phenyl-ethyl]-piperazin-1-yl}-ethyl)-phosphonic acid;

{4-[2-(3,5-Bis-trifluoromethyl-benzyloxy)-1-(2,3-difluoro-phenyl)-ethyl]-piperazin-1-yl}-acetic acid;

{4-[2-(3,5-Bis-trifluoromethyl-benzyloxy)-1-(2-nitro-phenyl)-ethyl]-piperazin-1-yl}-acetic acid;

N-[(2-{4-[2-(3,5-Bis-trifluoromethyl-benzyloxy)-1-phenyl-ethyl]-piperazin-1-yl}-ethoxy)-acetyl]-methanesulfonamide;

{4-[2-(3,5-Dichloro-benzyloxy)-1-phenyl-ethyl]-piperazin-1-yl}-acetic acid;

{4-[2-(3,5-Bis-trifluoromethyl-benzyloxy)-1-(4-cyano-phenyl)-ethyl]-piperazin-1-yl}-acetic acid;

5-{4-[2-(3,5-Bis-trifluoromethyl-benzyloxy)-1-phenyl-ethyl]-piperazin-1-ylmethyl}-2,4-dihydro-[1,2,4]triazol-3-one;

1-[2-(3,5-Bis-trifluoromethyl-benzyloxy)-1-phenyl-ethyl]-4-[4-(1H-tetrazol-5-yl) -butyl]-piperazine;

1-[2-(3,5-Bis-trifluoromethyl-benzyloxy)-1-phenyl-ethyl]-4-[2-(1H-tetrazol-5-ylmethoxy)-ethyl]-piperazine;

1-[2-(3,5-Bis-trifluoromethyl-benzyloxy)-1-(4-fluoro-phenyl)-ethyl]-4-[4-(1H -tetrazol-5-yl)-butyl]-piperazine;

1-{2-[1-(3,5-Bis-trifluoromethyl-phenyl)-ethoxy]-1-phenyl-ethyl}-4-[4-(1H -tetrazol-5-yl)-butyl]-piperazine;

1-{2-[1-(3,5-Bis-trifluoromethyl-phenyl)-ethoxy]-1-phenyl-ethyl}-4-[5-(1H -tetrazol-5-yl)-pentyl]-piperazine;

(2-{4-[2-(3,5-Bis-trifluoromethyl-benzyloxy)-1-phenyl-ethyl]-piperazin-1-yl}-ethoxy)-acetic acid isobutyl ester;

3-{4-[2-(3,5-Bis-trifluoromethyl-benzyloxy)-1-phenyl-ethyl]-piperazin-1-ylmethyl}-benzoic acid; and 4-{4-[2-(3,5-Bis-trifluoromethyl-benzyloxy)-1-phenyl-ethyl]-piperazin-1-yl}-butyric acid;

or non-toxic pharmaceutically acceptable salt, individual optical isomer or individual diastereoisomer thereof.

4. A pharmaceutical composition comprising a therapeutically effective amount of an α-arylethylpiperazine according to claim 3, or an individual enantiomer, diastereoisomer or non-toxic pharmaceutically acceptable salt thereof, and pharmaceutically acceptable solid or liquid excipient or carrier therefor.

5. A method for the treatment of asthma and/or allergic rhinitis in a patient, which comprises administering to said patient, a therapeutically effective amount of α-arylethylpiperazine of the formula I'

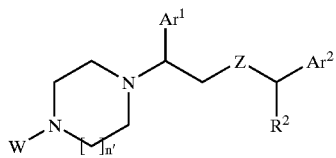
(I')

wherein
Z represents an oxygen atom;
n' represents 1;
R² represents a hydrogen atom or a methyl group;
W represents
  (i) a cyclohexyl group substituted by a COOH, or
  (ii) a group of formula R¹—(CH₂)ₙ—X—(CH₂)ₘ— in which
    R¹ represents a CN, CONHSO₂alkyl, COOH, COOalkyl, SO₃H, PO(OH)₂, a phenyl group mono-substituted by COOH, a tetrazole of the formula

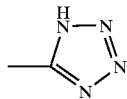

or a triazolone of formula

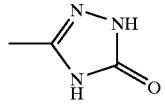

X represents a single bond, an oxygen atom or a methylene group;
m represents 1 or 2, provided that m is not 1 when X is an oxygen atom;
n represents 0, 1 or 2,
Ar¹ represents phenyl, a mono-, di- or tri-substituted phenyl group in which the substituents are selected from a halogen atom, an alkyl group, CN or NO₂;
Ar² represents a substituted aryl group of formula

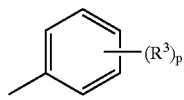

in which
R³ represents a halogen atom or a trifluoromethyl group;
p represents 1, 2 or 3;
the alkyl groups being linear or branched and having 1 to 4 atoms of carbon, or an individual enantiomer, diastereoisomer or non-toxic pharmaceutically acceptable salt thereof.

6. The method of claim 5 wherein the arylethylpiperazine of formula I' is selected from the group consisting of:
[2-(4-{2-[1-(3,5-Bis-trifluoromethyl-phenyl)-ethoxy]-1-phenyl-ethyl}-piperazin-1-yl)-ethoxy]-acetic acid;
(4-{2-[1-(3,5-Bis-trifluoromethyl-phenyl)-ethoxy]-1-phenyl-ethyl}-piperazin-1-yl)-acetic acid;
4-{4-[2-(3,5-Bis-trifluoromethyl-benzyloxy)-1-phenyl-ethyl]-piperazin-1-yl}-cyclohexanecarboxylic acid;
6-{4-[2-(3,5-Bis-trifluoromethyl-benzyloxy)-1-phenyl-ethyl]-piperazin-1-yl}-hexanoic acid;
{4-[2-(3,5-Bis-trifluoromethyl-benzyloxy)-1-phenyl-ethyl]-piperazin-1-yl}-acetonitrile;
3-{4-[2-(3,5-Bis-trifluoromethyl-benzyloxy)-1-phenyl-ethyl]-piperazin-1-yl}-propane-1-sulfonic acid;
5-{4-[2-(3,5-Bis-trifluoromethyl-benzyloxy)-1-phenyl-ethyl]-piperazin-1-yl}-pentanoic acid;
(2-{4-[2-(3,5-Bis-trifluoromethyl-benzyloxy)-1-phenyl-ethyl]piperazin-1yl}-ethoxy)-acetic acid;
{4-[2-(3,5-Bis-trifluoromethyl-benzyloxy)-1-phenyl-ethyl]-piperazin-1-yl}-acetic acid;
{4-[2-(3,5-Bis-trifluoromethyl-benzyloxy)-1-(3,4,5-trifluoro-phenyl)-ethyl]-piperazin-1-yl}-acetic acid;
4-{4-[2-(3,5-Bis-trifluoromethyl-benzyloxy)-1-phenyl-ethyl]-piperazin-1-ylmethyl}-benzoic acid;
{4-[2-(3,5-Dibromo-benzyloxy)-1-phenyl-ethyl]-piperazin-1-yl}-acetic acid;
{4-[2-(3,5-Bis-trifluoromethyl-benzyloxy)-1-para-tolyl-ethyl]-piperazin-1-yl}-acetic acid;
(2-{4-[2-(3,5-Bis-trifluoromethyl-benzyloxy)-1-phenyl-ethyl]-piperazin-1-yl}-ethyl)-phosphonic acid;
{4-[2-(3,5-Bis-trifluoromethyl-benzyloxy)-1-(2,3-difluoro-phenyl)-ethyl]-piperazin-1-yl}-acetic acid;
{4-[2-(3,5-Bis-trifluoromethyl-benzyloxy)-1-(2-nitro-phenyl)-ethyl]-piperazin-1-yl}-acetic acid;
N-[(2-{4-[2-(3,5-Bis-trifluoromethyl-benzyloxy)-1-phenyl-ethyl]-piperazin-1-yl}-ethoxy)-acetyl]-methanesulfonamide;
{4-[2-(3,5-Dichloro-benzyloxy)-1-phenyl-ethyl]-piperazin-1-yl}-acetic acid;
{4-[2-(3,5-Bis-trifluoromethyl-benzyloxy)-1-(4-cyano-phenyl)-ethyl]-piperazin-1-yl}-acetic acid;
5-{4-[2-(3,5-Bis-trifluoromethyl-benzyloxy)-1-phenyl-ethyl]-piperazin-1-ylmethyl}-2,4-dihydro-[1,2,4]triazol-3-one;
1-[2-(3,5-Bis-trifluoromethyl-benzyloxy)-1-phenyl-ethyl]-4-[4-(1H-tetrazol-5-yl) -butyl]-piperazine;
1-[2-(3,5-Bis-trifluoromethyl-benzyloxy)1-phenyl-ethyl]-4-[2-(1H-tetrazol-5-ylmethoxy)-ethyl]-piperazine;
1-[2-(3,5-Bis-trifluoromethyl-benzyloxy)-1-(4-fluoro-phenyl)-ethyl]-4-[4-(1H -tetrazol-5-yl)-butyl]-piperazine;
1-{2-[1-(3,5-Bis-trifluoromethyl-phenyl)-ethoxy]-1-phenyl-ethyl}-4-[4-(1H -tetrazol-5-yl)-butyl]-piperazine;
1-{2-[1-(3,5-Bis-trifluoromethyl-phenyl)-ethyl]-1phenyl-ethyl}-4-[5-(1H -tetrazol-5yl)-pentyl]-piperazine;
(2-{4-[2-(3,5-Bis-trifluoromethyl-benzyloxy)-1-phenyl-ethyl]-piperazin-1-yl}-ethoxy)-acetic acid isobutyl ester;
3-{4-[2-(3,5-Bis-trifluoromethyl-benzyloxy)-1-phenyl-ethyl]-piperazine-1-ylmethyl}-benzoic acid; and
4-{4-[2-(3,5-Bis-trifluoromethyl-benzyloxy)-1-phenyl-ethyl]-piperazine-1-yl}-butyric acid;
or non-toxic pharmaceutically acceptable salt, individual optical isomer or individual diastereoisomer thereof.

* * * * *